United States Patent [19]
Tankovich et al.

[11] Patent Number: 6,050,990
[45] Date of Patent: Apr. 18, 2000

[54] METHODS AND DEVICES FOR INHIBITING HAIR GROWTH AND RELATED SKIN TREATMENTS

[75] Inventors: Nikolai I. Tankovich, San Diego, Calif.; Kurt A. Dasse, Needham; David H. Fine, Lincoln, both of Mass.; Paul W. Fairchild, San Diego, Calif.; Zhong-Quan Zhao, San Diego, Calif.; Mike Lefebvre, San Diego, Calif.; John Lee, Jr., Ridgefield, Conn.; Jonathan L. Rolfe, North Easton, Mass.; Susan Murrell, River Edge, N.J.; Allen Hunter, II, San Diego, Calif.; Amanda J Reynolds, Richmond, United Kingdom; Vladimir G. Kolinko, San Diego, Calif.

[73] Assignee: ThermoLase Corporation, San Diego, Calif.

[21] Appl. No.: 08/984,892

[22] Filed: Dec. 4, 1997

Related U.S. Application Data

[60] Provisional application No. 60/052,718, Jul. 16, 1997, and provisional application No. 60/033,238, Dec. 5, 1996.

[51] Int. Cl.⁷ ................................................. A61B 17/36
[52] U.S. Cl. .................................................. 606/9; 606/16
[58] Field of Search ............................. 606/8–13, 15–17; 514/526

[56] References Cited

U.S. PATENT DOCUMENTS

| | | |
|---|---|---|
| 3,538,919 | 11/1970 | Mayer. |
| 3,693,623 | 9/1972 | Harte et al.. |

(List continued on next page.)

FOREIGN PATENT DOCUMENTS

| | | |
|---|---|---|
| B-57576/86 | 11/1986 | Australia. |
| 1208702 | 7/1986 | Canada. |
| 1041610 | 6/1994 | Canada. |
| 1071092A | 9/1991 | China. |
| 064967 | 4/1995 | European Pat. Off.. |
| 2267122 | 11/1975 | France. |
| 2590791 | 6/1987 | France. |
| 2595239 | 9/1987 | France. |

(List continued on next page.)

OTHER PUBLICATIONS

Androni, Porphyrins in Tumor Phototherapy, 143–155 (1984).

(List continued on next page.)

*Primary Examiner*—Linda C. M. Dvorak
*Assistant Examiner*—Roy Gibson
*Attorney, Agent, or Firm*—Fish & Richardson P.C.

[57] ABSTRACT

Methods of applying laser light to the skin, and apparatus therefor, include methods for removing hair, for synchronizing hair growth, for stimulating hair growth, for treating Herpes virus, for reducing sweat and body odor, for in situ formation of a chromophore in hair ducts, for reducing light loss at the skin surface, for grafting of hair stem cells, and for removing keloid or hypertrophic scars. The hair removal methods include controlling the proportions of photomechanical and photothermal damage by selection of laser parameters, chromophore particle size and/or pulse duration, with optional dynamic skin cooling. Additional hair removal methods include infiltrating a photoactivated drug into hair ducts and exposing the skin to sunlight or administering an anti-proliferative agent into hair ducts, for example, by encapsulating the anti-proliferative agent in a slow release vehicle. The methods of treating Herpes virus, reducing sweat or body odor, and removing keloid or hypertrophic scars include infiltrating a light-absorbing contaminant into hair ducts or other openings in the skin and illuminating the contaminated skin section. The methods for stimulating hair growth include grafting of cloned auto hair stem cells the hair ducts or administering methionine to a skin section to increase hair growth. Apparatus useful in performing these methods include devices for making a smooth optical boundary between skin and air or for dividing a light beam into a plurality of smaller light beams, and dressings for use before, during and after laser illumination.

9 Claims, 32 Drawing Sheets

U.S. PATENT DOCUMENTS

| | | |
|---|---|---|
| 3,769,963 | 11/1973 | Goldman et al. . |
| 3,794,028 | 2/1974 | Mueller et al. . |
| 3,821,510 | 6/1974 | Muncheryan . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,712,543 | 12/1987 | Baron . |
| 4,813,412 | 3/1989 | Yamazaki . |
| 4,919,664 | 4/1990 | Oliver . |
| 5,057,104 | 10/1991 | Chess . |
| 5,059,192 | 10/1991 | Zaias . |
| 5,217,455 | 6/1993 | Tan . |
| 5,226,907 | 7/1993 | Tankovich . |
| 5,236,950 | 8/1993 | Aoyama et al. . |
| 5,282,797 | 2/1994 | Chess . |
| 5,290,273 | 3/1994 | Tan . |
| 5,304,170 | 4/1994 | Green . |
| 5,360,447 | 11/1994 | Koop . |
| 5,401,503 | 3/1995 | Murayama . |
| 5,423,803 | 6/1995 | Tankovich . |
| 5,425,728 | 6/1995 | Tankovich . |
| 5,464,436 | 11/1995 | Smith . |
| 5,474,528 | 12/1995 | Messerol . |
| 5,486,172 | 1/1996 | Chess . |
| 5,519,534 | 5/1996 | Smith . |
| 5,556,783 | 9/1996 | Lavker . |
| 5,558,666 | 9/1996 | Dewey et al. . |
| 5,558,667 | 9/1996 | Yarborough . |
| 5,595,568 | 1/1997 | Anderson et al. . |
| 5,630,811 | 5/1997 | Miller . |
| 5,632,741 | 5/1997 | Zavislan et al. ............................ 606/9 |
| 5,647,866 | 7/1997 | Zaias . |
| 5,735,844 | 4/1998 | Anderson et al. ........................ 606/9 |
| 5,767,152 | 6/1998 | Nielsen et al. ......................... 514/526 |

FOREIGN PATENT DOCUMENTS

| | | |
|---|---|---|
| 2515697 | 10/1975 | Germany . |
| 3220962 | 12/1983 | Germany . |
| 63-249577 | 10/1988 | Japan . |
| 2157176A | 10/1985 | United Kingdom . |
| WO 80/02640 | 12/1980 | WIPO . |
| WO 86/02783 | 5/1986 | WIPO . |
| WO9011653 | 10/1990 | WIPO . |
| WO 91/04073 | 4/1991 | WIPO . |
| WO91/04073 | 4/1991 | WIPO . |
| WO 91/13653 | 9/1991 | WIPO . |
| WO91/13652 | 9/1991 | WIPO . |
| WO 93/21992 | 11/1993 | WIPO . |
| WO93/21841 | 11/1993 | WIPO . |

OTHER PUBLICATIONS

Anders et al., Conf. Laser 77 Optics Electronics 20–24 (Jun. 1997).

Coleman, A Visit to the Office of Dr. John Yarborough, J. Dermatol. Surg. Oncol., 20: 332–335, (1994).

Finkelstein et al., Epilation of Hair–Bearing Urethral Grafts Utilizing the Neodymium: YAG Surgical Laser, Lasers in Surgery and Medicine, 10: 189–193, (1990).

Kaufmann et al., Cutting and Skin Ablative Properties of Pulsed Mid–Infrared Laser Surgery, J. Dermatol. Surg. Oncol., 20: 112–118, (1994).

Dreno et al., The Benefit of Chilling In Argon–Laser Treatment of Port–Wine Stains, Plastic Reconstr. Surg. 75.1: 42–45, (1985).

NelsoN et al., Dynamic Epidural Cooling in Conjunction with Laser–Induced Photothermolysis of Port Wine Stain Blood Vessels, Lasers in Surgery and Medicine 19: 224–229, (1989).

Finkel et al., Pulsed Alexandrite Laser Technology for Noninvasive Hair Removal, J. Clin. Laser Med. & Surg. 15: 225–229 (1997).

Nanni et al., Optimizing Treatment Parameters for Hair Removal Using a Topical Carbon—Based Solution and 1064–nm Q–Switched Neodymium: Yag Laser Energy, Arch. Dermatol 133: 1546–1549, (1997).

K. L. Erbium Laser Assists Transdermal Drug Delivery Medical Laser Report, (Feb. 1997).

Chan et al., Effects of Compression on Soft Tissue Optical Properties, IEEE Journal of Special Topics in Quantam Electronics on Lasers in Medicine and Biology. 2(4): 943–950 (Dec. 1996).

PLUCKED HAIR FIBRE MORPHOLOGIES:

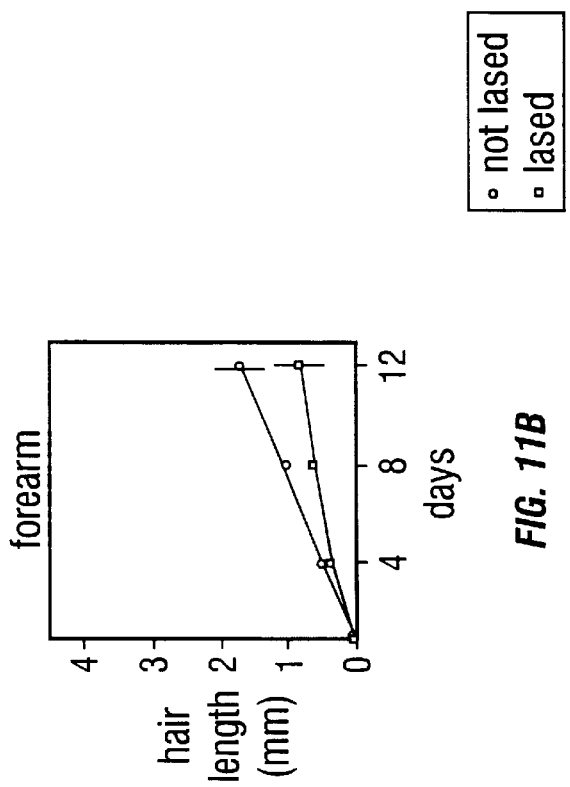
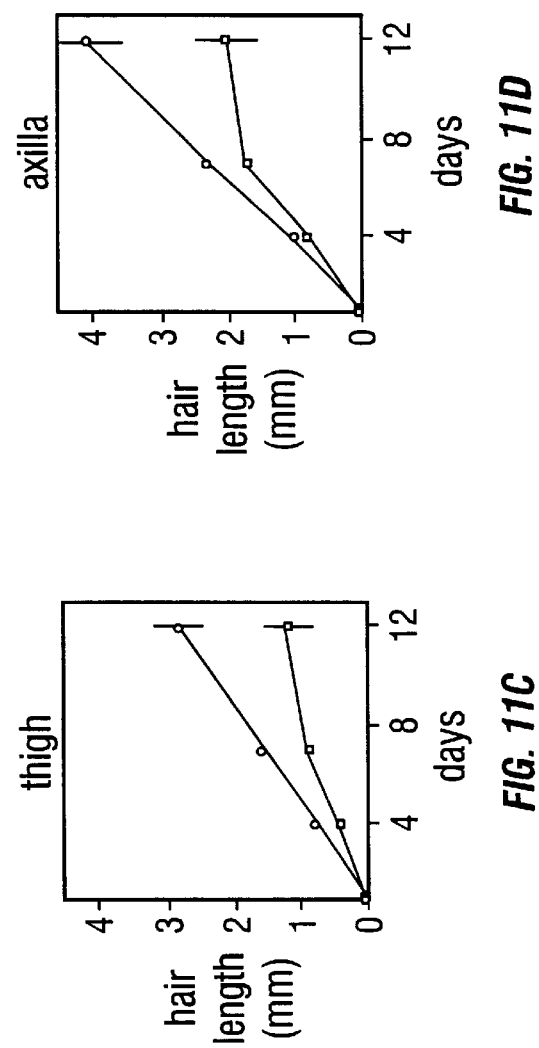
FIG. 11A  FIG. 11B  FIG. 11C  FIG. 11D

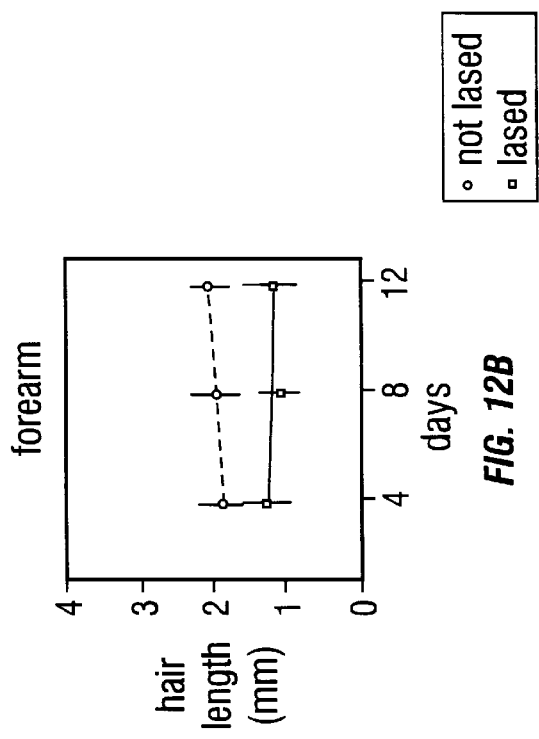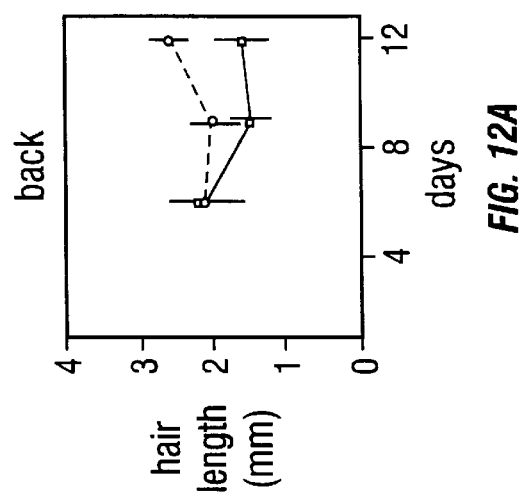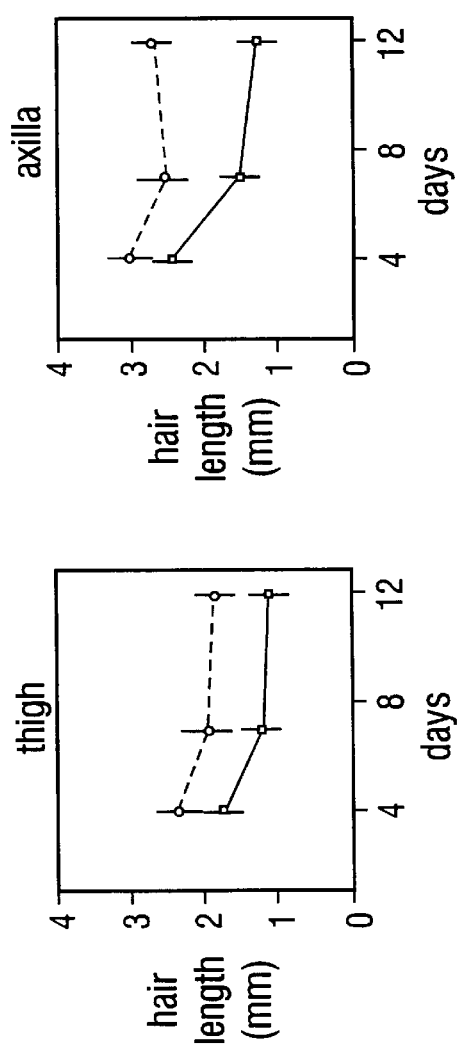

F: focal length of individual lens

D: diameter of individual lens

METHODS AND DEVICES FOR INHIBITING HAIR GROWTH AND RELATED SKIN TREATMENTS

CROSS-REFERENCE TO RELATED APPLICATIONS

This application is a continuation-in-part application of U.S. provisional application Ser. No. 60/052,718, filed on Jul. 16, 1997, and U.S. provisional application Ser. No. 60/033,238 filed on Dec. 5, 1996.

This application is related to co-pending U.S. patent applications Ser. No. 08/955,390 filed Oct. 21, 1997; Ser. No. 08/777,576, filed Dec. 31, 1996; Ser. No. 08/695,200, filed Aug. 1, 1996; Ser. No. 08/644,231, filed May 13, 1996 now U.S. Pat. No. 5,752,949; Ser. No. 08/492,283, filed Jun. 19, 1995 now U.S. Pat. No. 5,752,948; Ser. No. 08/489,358, filed Jun. 12, 1995 now U.S. Pat. No. 5,817,089; Ser. No. 08/489,352, filed Jun. 12, 1995 now U.S. Pat. No. 5,713,845; and to U.S. application Ser. No. 08/985,856, filed on even date with this application, and which is incorporated herein by reference.

TECHNICAL FIELD

This invention relates to devices and methods for hair removal and skin treatments.

BACKGROUND

The known techniques of hair removal include electrolysis and various laser hair removal techniques and skin treatments. Laser hair removal is described in United States patents to Weissman et al., U.S. Pat. No. 4,388,924; Sutton, U.S. Pat. No. 4,617,926; Mayer, U.S. Pat. No. 3,538,919; and Zaias, U.S. Pat. No. 5,059,192.

It is also known to effect long-term inhibition of hair growth by infiltrating a light-absorbing contaminant into hair ducts in a skin section prior to laser treatment. This technique is described in U.S. Pat. Nos. 5,226,907 and 5,425,728 to Tankovich. A contaminant applied topically can also be used to facilitate laser skin resurfacing. The contaminant is infiltrated beneath the surface layers of the stratum corneum, and then the skin surface bearing the contaminant is illuminated so as to remove the surface layers of the stratum corneum. This technique is described in U.S. Pat. No. 5,423,803 to Tankovich.

Accordingly, after noting the limitations of the prior art techniques, the inventors of the present application have devised new methods and devices used in long term prevention of hair growth and other beneficial skin treatments.

SUMMARY

One embodiment of the invention is a method for inducing hairs in a section of skin into synchronized hair growth by applying a shock to hair follicles in the section of skin.

Another embodiment of the invention is a method for increasing the gradient of energy loss with depth in skin to assist in forcing contaminant particles into spaces in hair ducts and other skin structures. Devices for dividing a beam of light directed to a skin surface into a plurality of substantially smaller beams are useful for exerting a net downward vector on contaminant particles within hair ducts or other skin structures in the practice of the invention.

Another embodiment of the invention is a method for infiltrating a contaminant into hair ducts on a section of skin wherein the section of skin is covered with an occlusive dressing, such as a hydrogel, for long enough to cause spreading of the contaminant into the occluded hair ducts.

Another embodiment of the invention is a hydrogel dressing wherein an active agent beneficial for soothing or protecting irritated or inflamed skin is incorporated in a hydrogel matrix.

Another embodiment of the invention is a composite hydrogel for covering a skin surface during laser treatments. The hydrogel is scrimless and comprises a film of thermoplastic hydrogel joined along one face with a layer of cross-linked hydrogel polymer and a photoindicator that changes appearance upon irradiation with a laser beam.

Another embodiment of the invention is a method for controlling the proportions of mechanical and thermal damage caused to tissue surrounding hair ducts during hair removal procedures. One portion of the particles in a contaminant is selected to be large enough to explode upon illumination, and a second portion of particle is selected to be small enough to heat up without explosion upon illumination. The mechanical damage is proportional to the portion of larger particles and the thermal damage is proportional to the smaller portion of particles in the contaminant.

Another embodiment of the invention is a method for providing any desired combination of photothermal and photomechanical damage to tissue surrounding hair ducts infiltrated with light absorbing particles. A skin section containing the hair ducts is illuminated with a combination of long and short pulses of light absorbed by the particles, wherein the long pulses avoid explosion of a selected portion of the particles, thereby causing photothermal damage, and the short pulses explode or vaporize another portion of the particles, thereby causing photomechanical damage.

In another embodiment of the invention, growth of unwanted hairs in hair ducts in a section of skin is obtained by topically applying a sunlight-activated photochemical associated with microcarrier particles to a section of skin, allowing the microcarrier particles to penetrate into hair ducts, and bathing the treated section of skin in sunlight.

Another embodiment of the invention is a method for inhibiting hair growth by applying an anti-proliferative agent to hair growth cells in a skin section so as to inhibit hair growth in the skin section.

In another embodiment of the invention, hair growth cells in hair ducts are contacted with a hair growth stimulating amount of methionine to stimulate hair growth in a section of skin.

Another embodiment of the invention is a method for preventing or treating outbreaks of a skin lesion due to reactivation of Herpes virus latent in hair ducts, wherein a contaminant is infiltrated into the hair ducts and the skin is illuminated by a light absorbed by the contaminant with consequent destruction of the Herpes virus in the hair ducts.

Another embodiment of the invention is a method for reducing production of sweat and/or odor in which a light-absorbing contaminant is infiltrated into spaces in hair ducts adjacent to or within sweat glands, and the skin is illuminated with a light so as to transfer heat and kinetic energy from the contaminant to the tissue surrounding the sweat glands, thereby devitalizing the sweat glands and reducing or eliminating production of sweat in the treated skin section.

Another embodiment of the invention is a method for tailoring the treatment regimen and energy level used during laser hair removal treatment to accommodate such factors as an individual's hair and skin color, the depth of hair follicles at the anatomic location of the site to be treated, and any previous history of hair removal treatment.

Another embodiment of the invention is an improvement in a method for laser assisted hair removal wherein skin is irradiated with an illumination beam with a square or circular shape no wider than about 8.0 mm at its widest point.

Another embodiment of the invention is a method for in situ formation within hair ducts of a metal oxide useful as a light absorbing chromophore during laser-assisted skin treatments.

Another embodiment of the invention is a method for reducing loss of light due to scattering and reflection of an incident light beam at a skin surface wherein the skin surface is covered with a transparent coating of liquid or a transparent device with a smooth upper surface for receiving an incident light beam. The covering has a refractive index slightly greater than or equal to the refractive index of skin to minimize loss of energy from the incident beam.

Another embodiment of the invention is a method for stimulating hair growth in which an individual's healthy undifferentiated papilla and/or bulge area stem cells are harvested, cloned, and inoculated interdermally into a section of skin to stimulate hair growth therein.

Another embodiment of the invention is a method for removal of hypertrophic or keloid scars wherein a scar is coated with a light absorbing contaminant and illuminated with short pulses of light preferentially absorbed by the contaminant for a time sufficient to selectively remove the scar.

Another embodiment of the invention is a method for inhibiting hair growth by filling hair ducts, from which hairs have optionally been removed, with a light guiding fluid, and, using a light well absorbed in blood chromophores, illuminating the section of skin containing the hair ducts so that at least a portion of the light is directed down the hair ducts by the fluid and absorbed in blood vessels that feed hair growth cells.

Another embodiment of the invention is a method for inhibiting hair growth by irradiating hair ducts infiltrated with light-absorbing contaminant particles, wherein the surface of a section of skin is precooled to about 10° C. to −10° C. prior to illumination, and a cooling flux is maintained on the surface of the skin section during a single laser pulse. The duration of the pulse is sufficient that tissue immediately surrounding the base of a hair follicle in the section of skin is destroyed by heat transferred from the irradiated contaminant. Meanwhile the cooling flux on the skin surface is sufficient that the temperature of tissue at a distance of about 1 to 2 hair follicle radii from the hair duct wall increases to no more than about 10° C. above body temperature during the pulse. At the conclusion of the pulse, the cooling flux is terminated, and the surface of the section of skin is allowed to return to body temperature before the three-step process is repeated.

Another embodiment of the invention is a method for activating or retarding hair growth wherein a contaminant containing metallic particles is applied to a skin section containing hair ducts, infiltrating at least some of the particles into follicles in the hair ducts, and applying to the skin section electromagnetic radiation having a frequency that is absorbed by the metallic particles. Radiation absorbed by the particles is transferred to surrounding follicular tissue in the form of heat. Depending on the phase of growth, thermal damage to the hair follicles can activate or retard hair growth.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 11 is a graph showing the average length of the hair above the skin surface at times zero to 12 weeks after laser treatment without waxing, wherein -●- represents the average length of the unlased hairs (controls) for the four subjects, and -■- represents the average length of the lased hairs for the four subjects.

FIG. 12 is a graph showing the results of measurements to determine the average length of hairs below the skin surface for the four subjects over the period from days 4 to 12 post lasing, wherein -●- represents the average length of the unlased hairs (controls) for the four subjects, and -■- represents the average length of the lased hairs for the four subjects. FIG. 12A is a graph showing the results on the backs of the subjects. FIG. 12B is a graph showing the results on the forearms of the subjects. FIG. 12C is a graph showing the results on the thighs of the subjects. FIG. 12D is a graph showing the results on the axilla of the subjects.

FIG. 20A schematically represents the transfer of photothermal energy to tissue surrounding a hair duct infiltrated with contaminant carbon particles with diameters in the 1.0 to 50 nanometer range.

FIG. 20B schematically represents the transfer of photomechanical energy to tissue surrounding a hair duct infiltrated with contaminant carbon particles with diameters of about 1.0 micron.

FIG. 20C schematically represents the combined transfer of photomechanical and photothermal energy to tissue surrounding a hair duct infiltrated with a combination of the contaminant carbon particles of FIGS. 20A and 20B.

FIG. 21A shows a multilamellar liposome; FIG. 21B shows an erythrocyte shadow encapsulating the photochemical; FIG. 21C shows a coacervate droplet containing the photochemical; FIG. 21D shows a latex sphere with monoclonal antibodies attached thereto; and FIG. 21E shows crystal particles with molecules of a photochemical bound thereto.

FIG. 32 is a graph showing the temperature increase in tissue surrounding a hair duct caused by laser irradiation, with a=radius of the hair follicle=25 $\mu$m; and R=the distance of the tissue from the center of the hair follicle. Solid line, R=a; dotted line, R=2a; dashed line, R=3a.

Like reference numbers and designations in the various drawings indicate like elements.

DETAILED DESCRIPTION

No. 1: A Method of Pretreatment to Synchronize Hair Growth Prior to Hair Removal Procedures Individual hairs in any given area of skin surface are not normally synchronized at a common point in the hair growth cycle. However, at any time some proportion of hairs in a skin section are in the anagen phase of the hair growth cycle. Hair stem cells and other follicular tissue are believed to be more susceptible to long term damage when they are activated, i.e., in the anagen phase of the hair growth cycle. However, during the mature anagen phase, the hair follicle is fully extended (to a depth of about 3.0 to 5.0 mm), and the distance to the bottom of the follicle from the skin surface is about twice that during the telogen phase of the hair growth cycle. This combination of circumstances makes laser-assisted hair removal difficult, particularly if the method of hair removal depends upon topical application of a substance, such as a contaminant, that is infiltrated throughout hair ducts to aid in the hair removal process.

Figure 1:
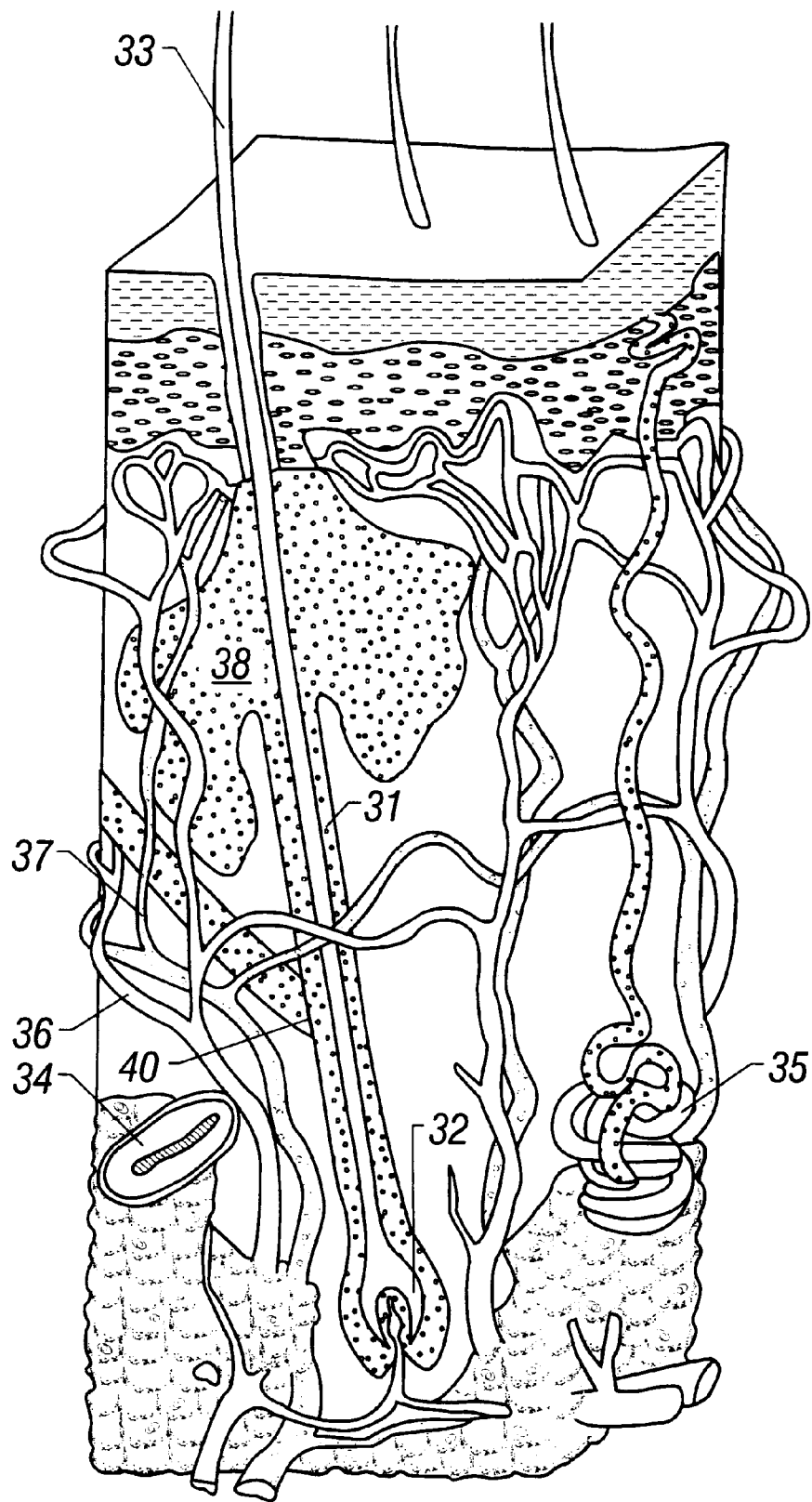
FIG. 1 is a schematic drawing of a section of human skin showing a cross section of one hair and associated skin structures.

This problem is overcome in one aspect of the invention by pretreating a skin section to be treated for hair removal so as to synchronize the hairs in the late telogen/early anagen phase. During this transition from the inactive to the active phases of the hair growth cycle, the hair follicle is still weak and shallow (at a depth of from 1.0 to 2.0 mm), yet the hair cells responsible for hair growth are just beginning to be activated and are, therefore, more susceptible to damage than at other phases of the hair growth cycle. FIG. 1 shows a section of human skin with a cross section of a hair shaft 33, a hair duct 31, a nerve ending 34, a sweat gland 35, a sebaceous gland 38, and arteries 36, veins 37 and papilla 32.

Figure 2:
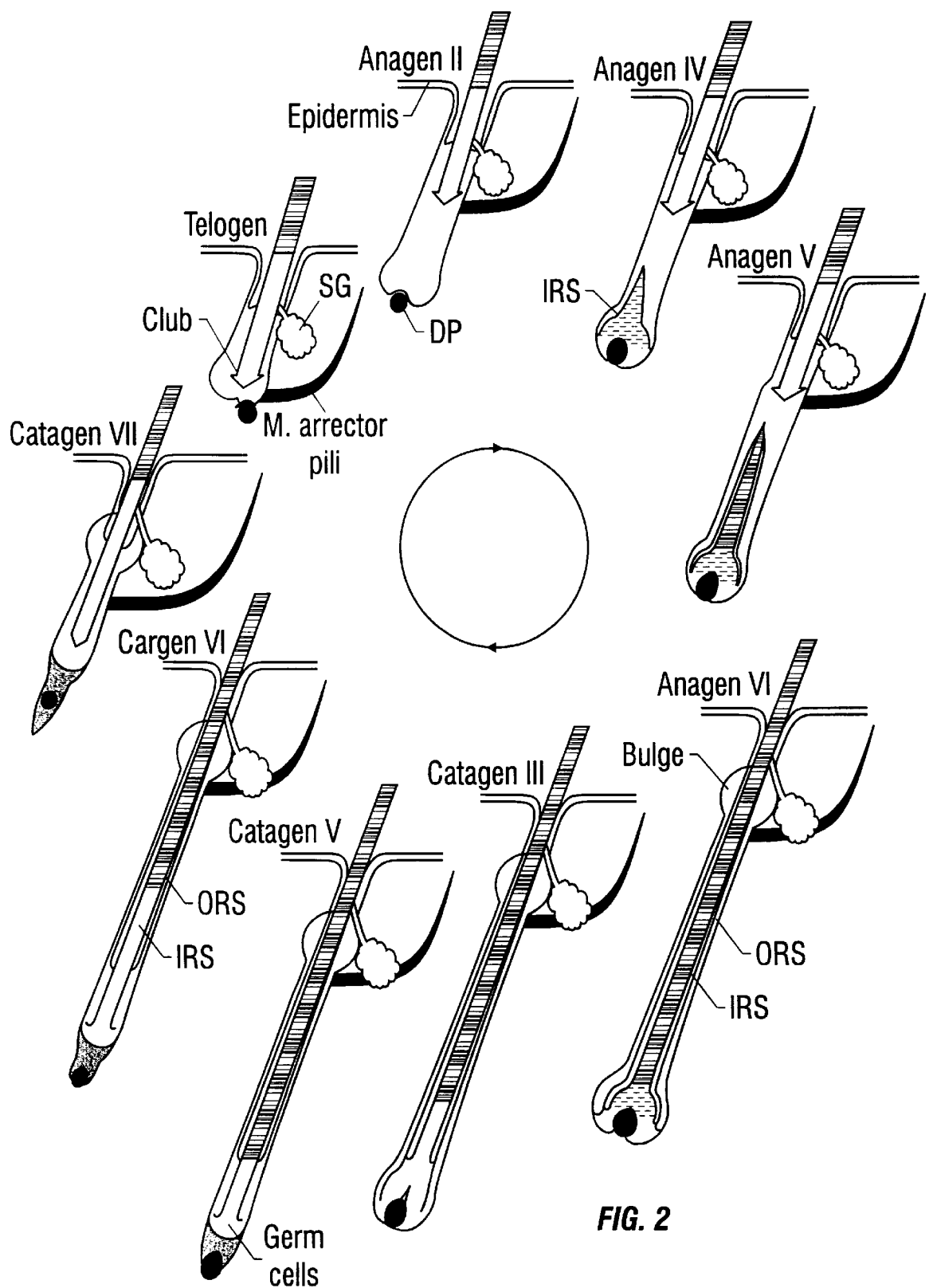
FIG. 2 is a drawing showing a hair passing through the nine stages of the hair growth cycle. SG=sebaceous gland; ORS=outer root sheath; IRS=inner root sheath; DP=papilla

This aspect of the invention provides a method for synchronizing the hair cycle of the hairs in a particular area of skin surface. There are nine phases or stages in the hair growth cycle: anagen II, IV, V and VI (growth phases), catagen III, V, VI and VII (regressing phases), and telogen (resting phase) as shown in FIG. 2. During the telogen phase, the follicle shrinks until the bottom of the follicle and the follicle papilla abut the bulge area. This process may be assisted by contraction of the hair root canal cells (similarly to smooth muscles cells) so as to drag the hair papilla to a position nearer the skin surface. Recent work has shown that stem cells located in the bulge area are responsible for hair regrowth during the anagen phase. At some point during telogen phase, the "normally slow cycle," stem cells of the bulge area are transiently activated, presumably by signals from the abutting follicular papilla. In response, the stem cells, which are responsible for hair regrowth, proliferate, shifting the hair into anagen phase. During the anagen phases, the follicle again extends to its full length, so that the bulge area of the hair duct is located about one-half way down the follicle just below the sebaceous gland. It is known to treat hair for hair removal during the anagen stage when the rapidly proliferating stem cells are easily damaged. However, at anagen stage the stem cells are located at a depth as great as 3.0 to 5.0 mm below the surface of the skin.

In one embodiment, the goal is to prepare a section of skin for hair removal and/or long-term inhibition of hair growth. It has been discovered that once the hairs are synchronized in the telogen/early anagen phase of the growth cycle, hair removal can be accomplished with increased efficiency by any known method. For example, one method includes irradiation of the synchronized follicles with light absorbed either by a naturally occurring chromophore in the hair duct, such as melanin, or by an externally applied light-absorbing contaminant infiltrated into hair follicles.

The hairs on a section of skin are synchronized in the late telogen/early anagen phase by irritating or slightly damaging the hair follicles in a section of skin so as to stimulate hairs in the skin section that are in a catagen or telogen phase to shift into anagen phase of the hair growth cycle. The irritation can be provided by mechanical, thermal, or chemical means. Any of these means will increase the flow of blood to the hair follicles. The only requirement is that the irritation or damage be sufficient to activate the natural repair response to slight damage or injury, but not sufficient to cause severe damage such as would cause hairs already in the anagen phase to be shifted to an inactive state.

For example, synchronous growth of human hair can be effected by application of a drug, such as Minoxidil, which increases flow of blood to the hair follicles, or application of Methionine (for example post waxing) to increase proliferation of papilla or matrix cells. Such drugs can be introduced into the hair root canal either by direct application or delivery in microcapsules.

Figure 35:
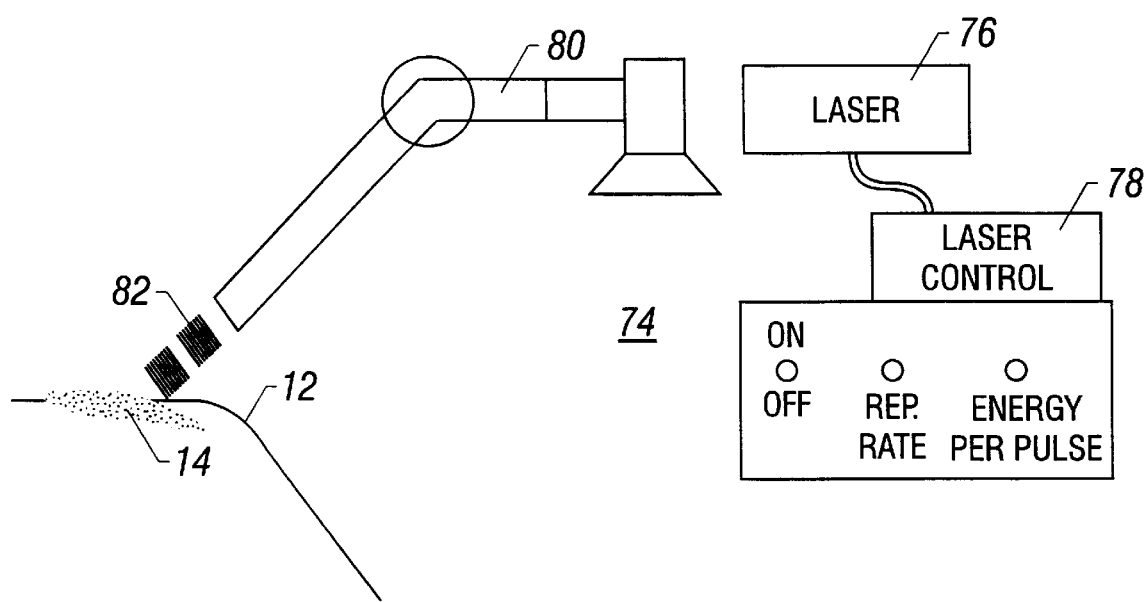
FIG. 35 is a schematic drawing showing a laser system including a laser control, an articulated arm for directing a laser beam, and a laser beam in spaced relation to a contaminant on a section of skin.

Alternatively, mild laser treatment of a skin section containing resting hair cells, or irradiation by a flash lamp, can be used to shock anagen phase hairs into telogen phase while stimulating the resting cells to transition into the anagen phase, thus synchronizing the hair cells in the growth cycle. In addition, waxing, plucking, or electrolysis of hair follicles can be used to provide the shock necessary to synchronize hair growth. The degree of irritation or mild injury administered is that sufficient to trigger the natural self-protective repair mechanism that shifts hairs to the telogen/early anagen phase without causing severe damage to the hair cells in the bulge area of the hair follicle. FIG. 35 shows a laser system 74 useful for illuminating a skin surface including a laser 76, a laser control 78, an articulated arm 80 for delivering a laser beam, and pulses of laser light 82 in spaced relation to a section of skin 12 having a contaminant 14 thereon.

Following application of the shock or irritant, a period of time is required for the phase shift to occur, for example a period of from about 3 to 25 days. It has been discovered by empirical tests that good results can generally be obtained by waiting for a period of about 7 to 21 days following administration of a shock or irritant for the hairs in a section of skin to substantially synchronize. Therefore, if the treatment to synchronize the hairs to telogen/early anagen phase growth is preparatory to administering a subsequent hair removal treatment, a period of about 7 to about 21 days should generally be allowed for the phase shift to occur before the subsequent hair removal treatment is undertaken.

Once hair growth is synchronized in late telogen/early anagen phase, the skin surface can be illuminated with short pulses of light at a frequency absorbed by a naturally occurring chromophore or externally infiltrated contaminant. For example, a ruby laser can be used to irradiate the melanin within shortened hair follicles. Methods of hair removal that depend for their effect upon the ability to infiltrate a light-absorbing contaminant deep into the hair follicle, such as those disclosed in U.S. Pat. Nos. 5,226,907 and 5,425,728, are enhanced by use of the invention. During the mature anagen period of the hair growth cycle when it is easiest to damage stem cells and other follicular tissue involved in hair growth, it is hardest to infiltrate the contaminant to the bottom of the hair follicle, and thereby ensure destruction of follicular tissue throughout the length of the hair duct. Synchronizing hair growth in the late telogen/early anagen phase greatly reduces the distance into a hair duct that a contaminant needs to be infiltrated.

When the hair removal treatment to be employed on the synchronized hairs utilizes an external contaminant infiltrated into the hair ducts, the pretreatment method can incorporate the following steps. First, a contaminant, i.e., one containing light absorbing chromophore particles, is gently applied to the skin section so that at least a portion of the contaminant enters the upper region of the hair follicles. For instance an oil or water-based suspension of carbon particles or other chromophore particles that absorb light in the near IR region of the spectrum, can be employed as the externally applied contaminant. Liposomes can also be used to deliver into the hair follicles any chromophore which has a good absorption at a laser wavelength that is appropriate for illumination of a skin section. Hair papilla and/or matrix cells can also be stained with a dye which has good absorption of light, using coherent or non-coherent light radiation. A mild concentration of a photosensitizer chemical (e.g., one that is activated by laser radiation to produce singlet oxygen) can also be administered to a skin section, allowed to become absorbed in hair growth cells, and then used to shock the hair follicles. Alternatively, a mild solution of a chemical that causes irritation to hair follicles upon contact can be administered to synchronously stimulate hair growth. For example levulenic acid applied to the skin surface so as to infiltrate into hair ducts in a concentration of about 0.002 to about 2 percent by volume will cause a mild irritation that will shock hair follicles.

The skin section can be cleaned using a non-irritating cleaner prior to application of the contaminant to remove oil and debris, such as lint and loose skin cells. For example, lint and cell debris can be removed from the skin section with any type of tape having a light adhesive, such as is used for lint removal from fabrics, and the like. Another example of a non-irritating cleaner is isopropyl alcohol. The skin section generally should not be vigorously brushed or rubbed during cleaning prior to administration of the contaminant because irritation will cause sebaceous glands in the hair ducts to exude a liquid wax that will obstruct entry of a contaminant.

As one example, the contaminant can be a suspension of carbon particles in the size range from about 0.2 to about 0.01 micron (carbon black) or in the size range up to about 1 micron. The carbon particles are suspended in or mixed with a light oil, such as light mineral oil, NF. Drakeol 13™ (PennDrake, Los Angeles, Calif.), is a preferred oil for this use.

When applied to the skin section prior to irradiation, at least a portion of the contaminant must enter the upper region of the hair follicles, i.e., the mouth of the hair follicles. Generally, merely applying the contaminant to the skin surface will cause the particles to infiltrate only about 20 microns into the hair follicles. Increased penetration of a contaminant containing oil may be obtained by allowing the contaminant to rest on the skin section for a period of time sufficient for the opening of the hair follicle to become enlarged before the next step is taken. This effect is thought to be due to the action of the light oil on the skin and hair follicles. Usually, allowing an oil-based contaminant to remain on a skin section for a period of about 15 minutes is sufficient to enlarge the openings of hair follicles to the fullest extent.

Next, to shock the hair follicles, the contaminated skin section is illuminated with one or two short pulses of light having a frequency highly absorbed by the contaminant particles. For example, if the contaminant contains carbon particles, a frequency is used that is well absorbed in carbon, but relatively transparent to skin, such as is provided by a Nd:YAG laser. Additional useful light sources are discussed in the Tankovich patents incorporated herein by reference.

In one embodiment of the invention, it is desirable to explode or fracture the contaminant particles in the hair ducts during illumination to drive them as far as possible into the depth of the hair follicles. In any event, it is necessary to irritate or mildly damage the follicular tissue, but only enough to trigger a natural repair mechanism in the follicles, causing any follicles in anagen phase to pass out of anagen phase into telogen phase. Short pulses of light having a low fluence in the range from about 1 to about 2.5 J/cm$^2$ can be used to avoid transferring substantial heat and/or kinetic energy from the chromophore particles to the hair follicles or surrounding tissue. Serious damage to the hair papilla should be avoided. Therefore, preferably no more energy is administered to the hair follicles during the pretreatment process than will raise the temperature of the follicle walls more than about 10° C. to about 20° C. above body temperature during the laser pulse.

During the rest period of about 7 to 21 days following administration of the shock, hair cells in anagen phase will cycle through telogen phase into early anagen phase, a point in the hair growth cycle referred to herein as "late telogen/early anagen phase." However, if too much heat is transferred to the hair follicles during the pretreatment, hair growth generally will not be synchronized.

After observing the rest period to allow synchronization of hair growth in the "late telogen/early anagen phase," a hair removal procedure can, in many cases, be undertaken with the expectation of an increased level of success. It has been discovered that when the hair growth cycle has been synchronized using the method of this invention, the percentage of hairs that are sufficiently devitalized to inhibit regrowth for an extended period of time (for example 3 to 6 weeks, or longer) is substantially increased.

Use of a contaminant for shocking the papillae is optional, and is omitted if the light absorbing chromophore to be illuminated during a hair removal procedure is naturally occurring, such as melanin in the hair ducts.

Sample process parameters useful when the pulses of light used in the skin pretreatment process of this invention are provided by a Nd:YAG laser and the contaminant comprises light mineral oil and carbon particles are as follows:

Wavelength about 1064 nm

Beam Shape: circle or square

Beam Size: about 8 mm diameter (circular) or 7×7 mm (square)

Fluence 1–2 J/cm$^2$

Pulse energy 0.5 J/pulse

In some cases it may be advantageous to repeat the pretreatment process from 1 to about 3 times before a procedure is attempted to illuminate the hairs with sufficient energy to cause hair removal and/or long term inhibition of hair growth. Alternatively, for particularly resistant sites, the pretreatment of this invention can be alternated with the laser hair removal treatment in fairly rapid succession. For instance, success has been obtained in the long-term inhibition of growth of a man's beard by three repetitions of the pretreatment/treatment cycle, spaced apart by a rest period of about 3 to about 5 days. The illumination at pretreatment was at 1.5 J/cm$^2$ to infiltrate the contaminant, and drive the follicles into telogen phase. The illumination for hair removal following the rest period was at 3.0 Jcm$^2$. In this embodiment of the invention, due to the short rest period, the contaminant introduced during each of the pretreatment procedures remained in place and was not replenished before the subsequent hair removal treatment, which followed immediately after the rest period was completed.

In yet another embodiment of the invention, the pretreatment method comprises the following steps. An oil-based contaminant containing a light-absorbing chromophore is applied as described above to the surface of a section of skin. The contaminant may be allowed to rest upon the skin for a period of time sufficient for the opening of the hair follicle to become enlarged, for example, about 15 minutes, before the next step is taken.

Next, a hair removal wax is applied over the oil-based contaminant on the skin surface and is allowed to dry. Any commercially available wax intended for hair removal can be used, for example Azulene™ or Ember™, both hard waxes, or Epillyss™, a soft wax. To adhere the wax to the skin surface, application of the wax commences from a location on the skin surface just outside the area covered with the oil-based contaminant. Adjacent strips of wax should overlap to form a covering that completely bridges the oily area and adheres to oil-free skin surface around the periphery. Once the wax has been allowed to thoroughly dry according to the manufacturer's instructions, the wax is stripped from the skin. Surprisingly, in the waxed area a significant proportion of the hairs will be removed from the hair follicles even though the wax was applied to water or oil-coated hairs. In addition, stripping the wax and extracting hairs from the hair follicles causes the light-absorbing particles to infiltrate throughout the hair follicles more completely. The stripping action also subjects the hair follicles to sufficient shock to synchronize hair growth after a rest period is observed, as described above. Following the rest period, hair removal procedures can be undertaken with the expectation of an increased level of efficiency.

This aspect of the invention having been fully described, it is further illustrated by the examples below. It will be understood, however, that the invention is not limited by the examples but is defined by the appended claims.

EXAMPLE 1

The following set of experiments was conducted to determine the period of time required after administration thereto of an irritant or shock for hair follicles to enter the late telogen/early anagen stage of the hair growth cycle. The data obtained indicates how long the rest period should be between administration of the shock and commencement of a hair removal procedure.

Figure 3:
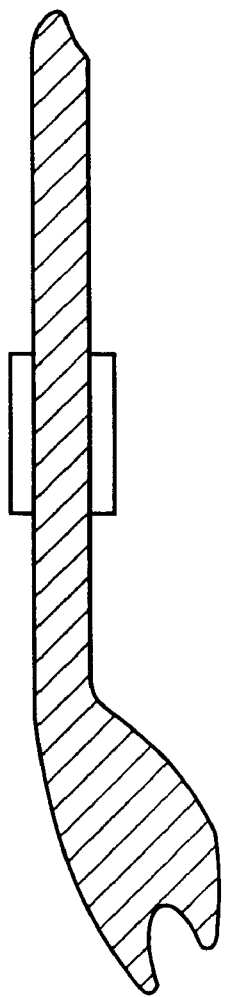
FIG. 3 shows the morphology of a plucked hair in anagen phase. The full hair matrix is shown as plucked from the end bulb. The lower portions of anagen hairs are soft and malleable, and may have a tendency to bend over after plucking so that they appear to be curved, or even hooked at their ends.
Figure 4:
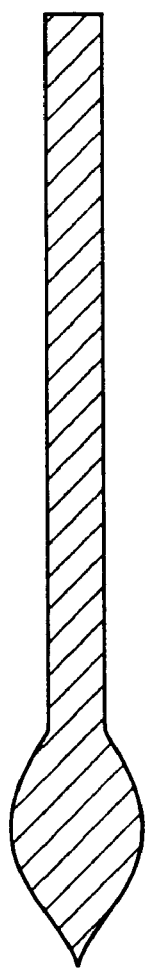
FIG. 4 shows the morphology of a plucked hair in telogen phase. The club-shaped tip at the bulb end is the distinguishing characteristic of a hair in the telogen phase.

The lower left forearm, wrist area, and hand of a human patient was selected as the location of the test sites. The untreated right hand and arm of the subject was used as a control. The locations on the subject's left hand and arm selected as test sites had been lased 2 months before this treatment, but 100% of the hairs had grown back. In addition, reference photographs of hairs in anagen and telogen phase were used for comparison with hairs plucked from the test sites. FIG. 3 shows the morphology of a plucked hair in anagen phase, with the full hair matrix shown as plucked from the end bulb. The lower portions of anagen hairs are soft and malleable, and may have a tendency to bend over after plucking so that they appear to be curved, or even hooked at their ends. FIG. 4 shows the morphology of a plucked hair in telogen phase. The club-shaped tip at the bulb end is the distinguishing characteristic of the telogen phase hair.

Figure 5:
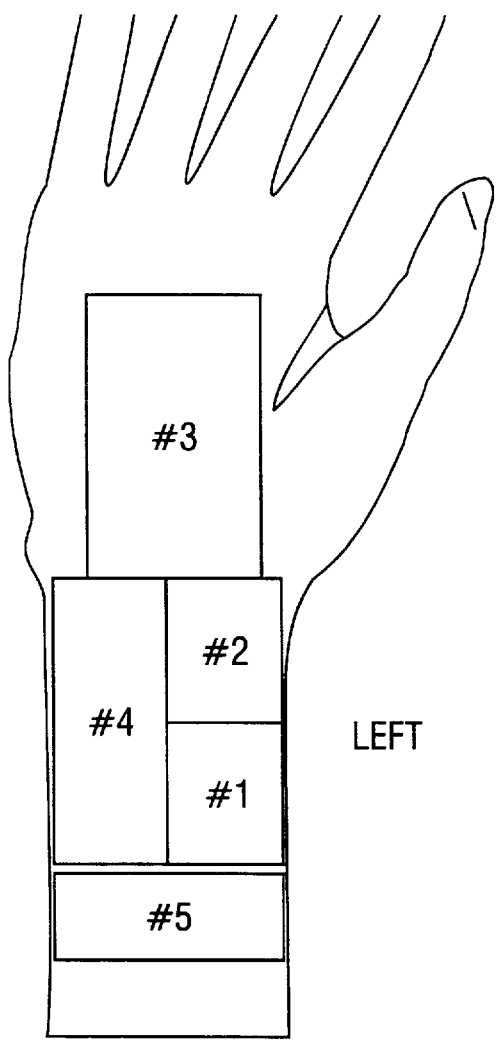
FIG. 5 shows the location of five sites (#'s 1–5) on the left hand of a human patient used as test sites to determine a phase shift in the hair growth cycle caused by laser illumination.

The test sites on the left hand, as shown in FIG. 5, were as follows:

| site # | Treatment protocol |
|---|---|
| 1 | Pluck hair, lase continuously with multiple passes 5 days after plucking |
| 2 | Pluck hair, lase continuously with multiple passes immediately after plucking |
| 3 | Pluck hair, no lasing |
| 4 | No plucking; lase continuously with multiple passes immediately after plucking, close shave hair after lasing |
| 5 | Close shave hair, no lasing |

Figure 6:
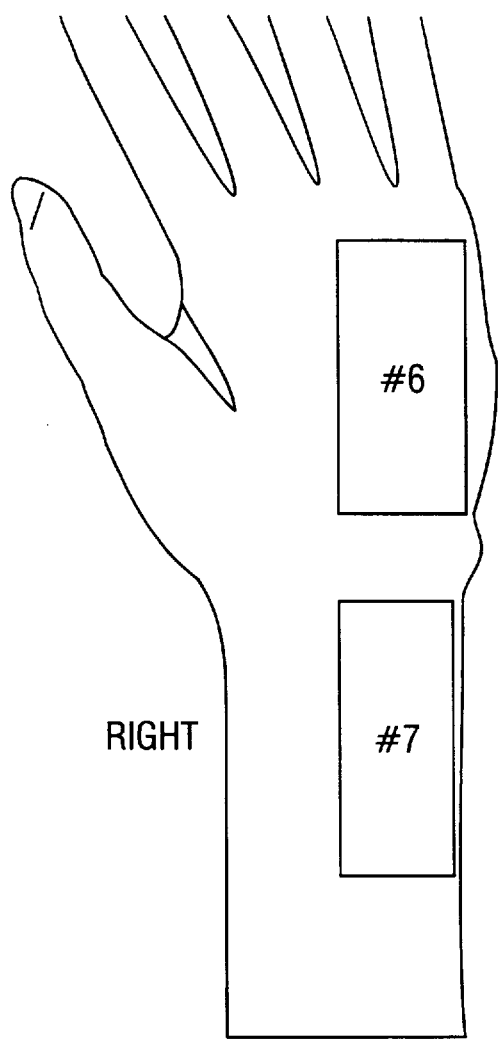
FIG. 6 shows the location of two sites (#'s 6–7) on the right hand of a human patient used as test sites to determine a phase shift in the hair growth cycle caused by laser illumination.

On the right hand, as shown in FIG. 6, the treated sites were as follows:

| site # | Treatment protocol |
|---|---|
| 6 | Close shave hair, no plucking |
| 7 | Close shave hair, no plucking |

For lasing, a Nd:YAG laser operating with a wavelength of 1.06 microns, repetition rate of 10 Hz, fluence of 3.0 J/cm$^2$ was used.

Eventually, all hairs above the skin surface in the test areas were plucked (#1–3) or shaved (#4–7). Sites # 5, 6, and 7 are controls for site #4, and site #3 is a control for sites #1 and 2. Records of hair regrowth were kept for all sites. The time for regrowth to reach a length of 3 mm was recorded. The hair was shaved as 3 mm of regrowth was exceeded. Records of hair density were also kept. Density was estimated by eye, by comparison with shaved and unshaved control areas on the right hand, which showed density and appearance at the beginning of the study. One-fourth of the hairs from each test site were plucked at each of weeks 1, 2, 4, and 6 post lasing for examination by microscope to determine the effect of laser induced modifications.

On day 8, hairs from site #7 were plucked for measuring. By comparison with the reference photograph of FIG. 3, the hair bulbs showed that the hairs were in anagen phase. By contrast, on day 8, hairs from site #4 were completely bleached and showed a tapering tip in the place of the hair bulb. The results of the tests at day 8 are shown in Table 1 below.

TABLE 1

| Site # | # of hairs | anagen | telogen | tapering | broken | mean length (mm) |
|---|---|---|---|---|---|---|
| 4 | 48 | 0 | 3 (6%) | 45 (94%) | 0 | 2.79 ± 0.25 |
| 7 | 27 | 24 (89%) | 2 (7%) | | 1 | 4.4 ± 0.4 |

Figure 7:
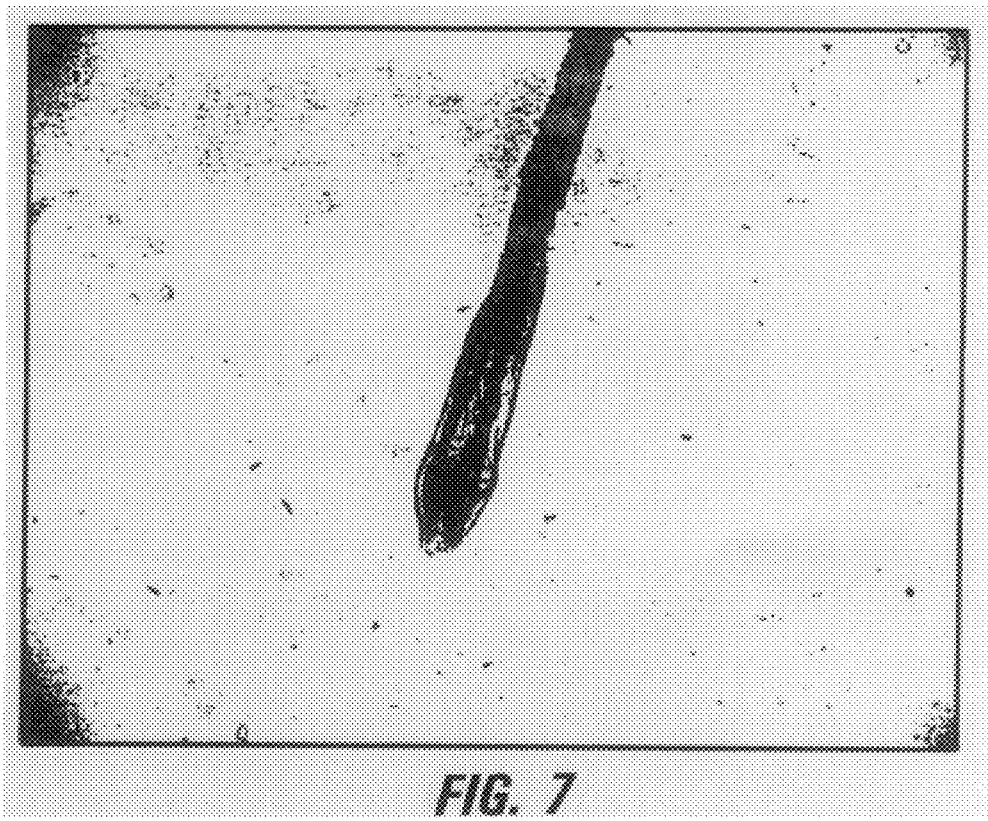
FIG. 7 shows a photograph of a hair in anagen phase from site #5 on day 8 post illumination.
Figure 8:
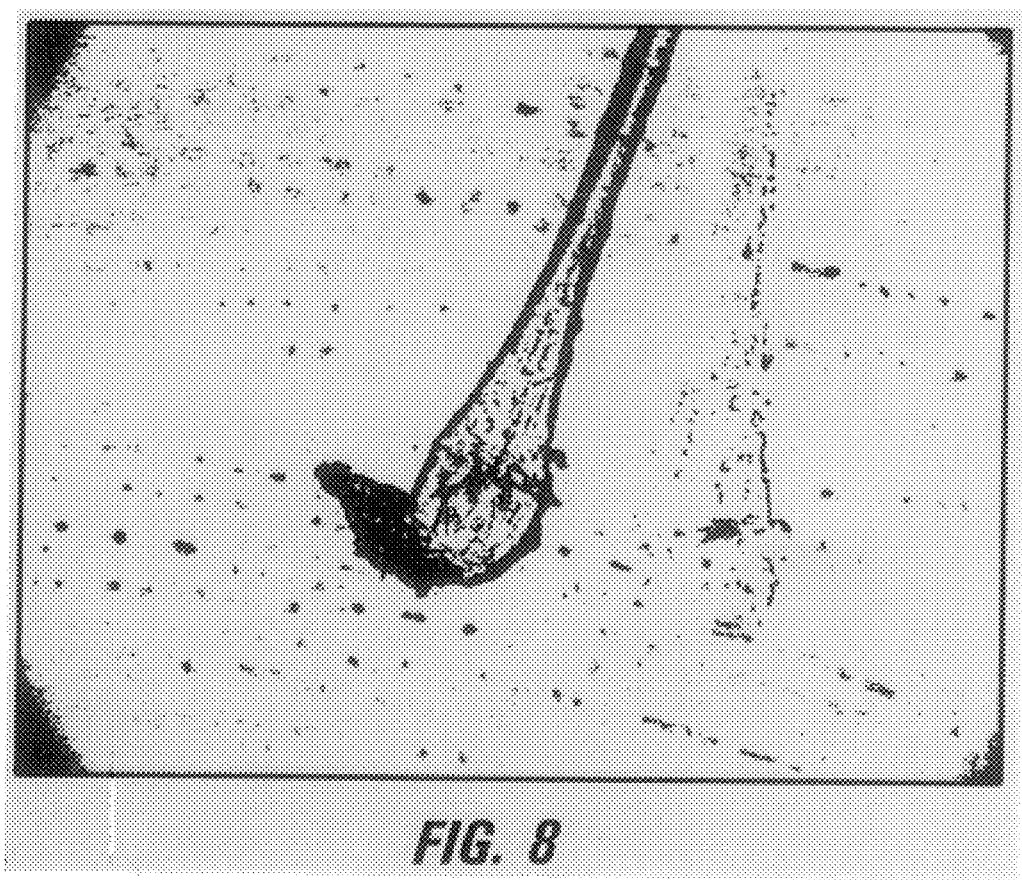
FIG. 8 shows a photograph of a hair in telogen phase from site #5.

FIG. 7 shows a photograph of a hair from site #5 on day 8. The lower portion (the bulb) is pigmented (dark brown) and the shape is straight, indicating that the hair is in anagen phase. By comparison, another hair from site #5 shown in FIG. 8 is transparent, indicating a lack of pigment (lack of melanin) and the bulb has a club shape. These characteristics indicate the hair is in telogen phase.

On day 14, hairs from site #4 would slide easily out of the follicle when pulled. The tip of the shaft was normally pigmented (pigmentation had recovered as compared to the rest of the shaft), but the tip was about 50% smaller than the rest of the shaft. Of the 18 hairs plucked from each site on day 14, the average length of the whole plucked hair was as follows:

| | |
|---|---|
| Site #4 | 2.5 ± 0.4 mm |
| Site #7 | 5.4 ± 0.6 mm |

On day 18, follow-up studies of hairs from sites #4 and #7 were conducted by microscopic examination and measurement of plucked hair shafts, with the results shown in Table 2 below:

TABLE 2

| Site # | # of hairs | anagen | telogen | tapering | broken | mean length (mm) |
|---|---|---|---|---|---|---|
| 4 | 13 | 0 | 1 | 12 | 0 | 7.1 ± 0.3 |
| 7 | 17 | 15 | 1 | 1 | 0 | 2.5 ± 0.35 |

Figure 10:
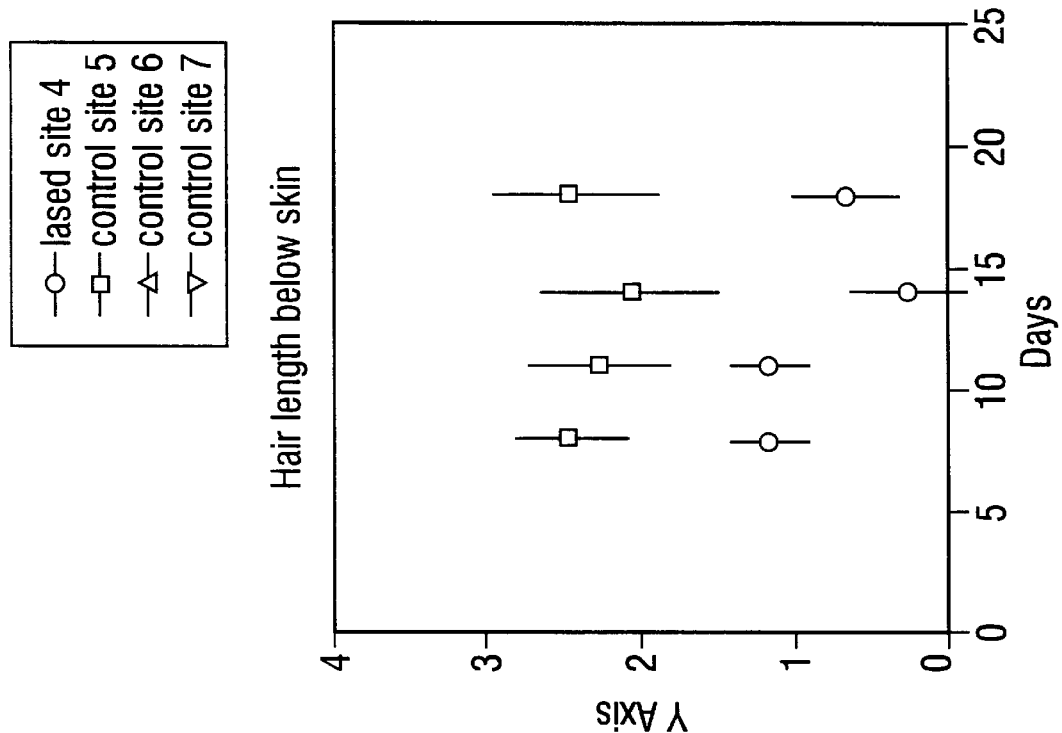
FIG. 10 is a graph showing the length of hair below the skin surface at control site #5 (-■-), and lased site #4 (-●-).
Figure 9:
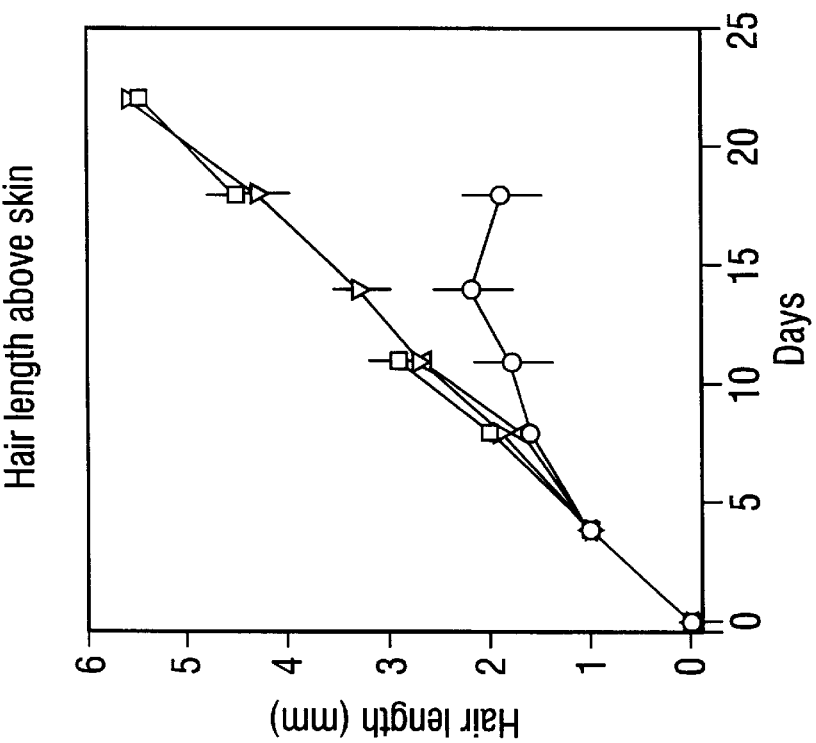
FIG. 9 is a graph showing the length of hair above the skin surface at site # 4 (-●-), site #5 (-■-), site #6 (-▲-), and site #7 (-▼-).

The hairs from sites 4–7 were also measured to determine the length of the hairs above the skin and the length of the hairs below the skin. The results of these studies are shown in FIGS. 9 and 10. The length of the hairs above the surface from lased site #4 clearly showed inhibition of hair growth as compared with the length of hairs from control sites. From these studies it was determined that 18 days after lasing, the hair bulbs for hairs in site #4 were less than 1 mm below the surface of the skin, while the hair bulbs of hairs from the control site were at a depth of about 2.5 mm beneath the surface of the skin. Thus, the hair ducts of the treated site had contracted as a result of being shocked. This data confirms that the lasing was sufficient to cause hairs at site #4 to pass into telogen phase.

Discussion of Results

On the laser treated sites, hair kept growing above the skin surface at the same rate as on the untreated (control) site during the first 4–8 days after treatment. Growth of hairs on the laser treated sites slowed down, then stopped, and the hairs fell out within the next 1–2 weeks. By contrast, the hairs on the control site continued to grow, obtaining a length that increased linearly with time.

Anagen and transition stage hairs on the laser treated site showed significant morphological changes (tapering at the hair bulb end) as early as the 4th day after treatment. This phenomenon continued until the hairs fell out. By contrast, telogen hairs remained unaffected by laser treatment and continued to follow a normal growth cycle.

When hairs that showed modifications after laser treatment were plucked, they were found to be half as long below the skin surface as were the normal untreated hairs (controls). Hairs that were not plucked showed bleaching down to the root, and then 1–2 weeks later started to recover pigmentation at the tapering end. Slim pigmented "tails" could be seen at the recovering end, yet the hairs never returned to normalcy and never resumed a normal growth cycle.

About three weeks after lasing, hairs started growing back in significantly reduced number in the laser-treated site. About 20% regrowth was observed 38 days after laser treatment. No telogen hairs were found on the laser treated sites 38 days post lasing, suggesting that telogen hairs were unaffected by laser treatment and synchronously cycled into active growing anagen hairs.

Black material in the upper portion of the hair follicles under the stratum corneum became visible on the laser treated sites about 2 weeks after treatment and remained visible without any signs of hair growth in the follicles. The dots of black material did not disappear after extensive lasing at 1.06 microns wavelength and 3.0 J/cm$^2$ fluence.

EXAMPLE 2

The procedures of Example 1 were repeated using four human subjects, except that four different sites were used for each subject: back, forearm, thigh and axilla. Control, unlased sites were also utilized at each of the four locations for each subject. FIG. 11 is a graph showing the average length of the hair above the skin surface at times zero to 12 weeks after laser treatment without waxing, wherein -●- represents the average length of the unlased hairs (controls) for the four subjects, and -570 - represents the average length of the lased hairs for the four subjects. The inhibition of hair growth caused by the mild laser treatment to shock the hairs was greatest on the back, thigh and axilla. Growth of hairs on the forearm was least affected.

Figures 13, 14:
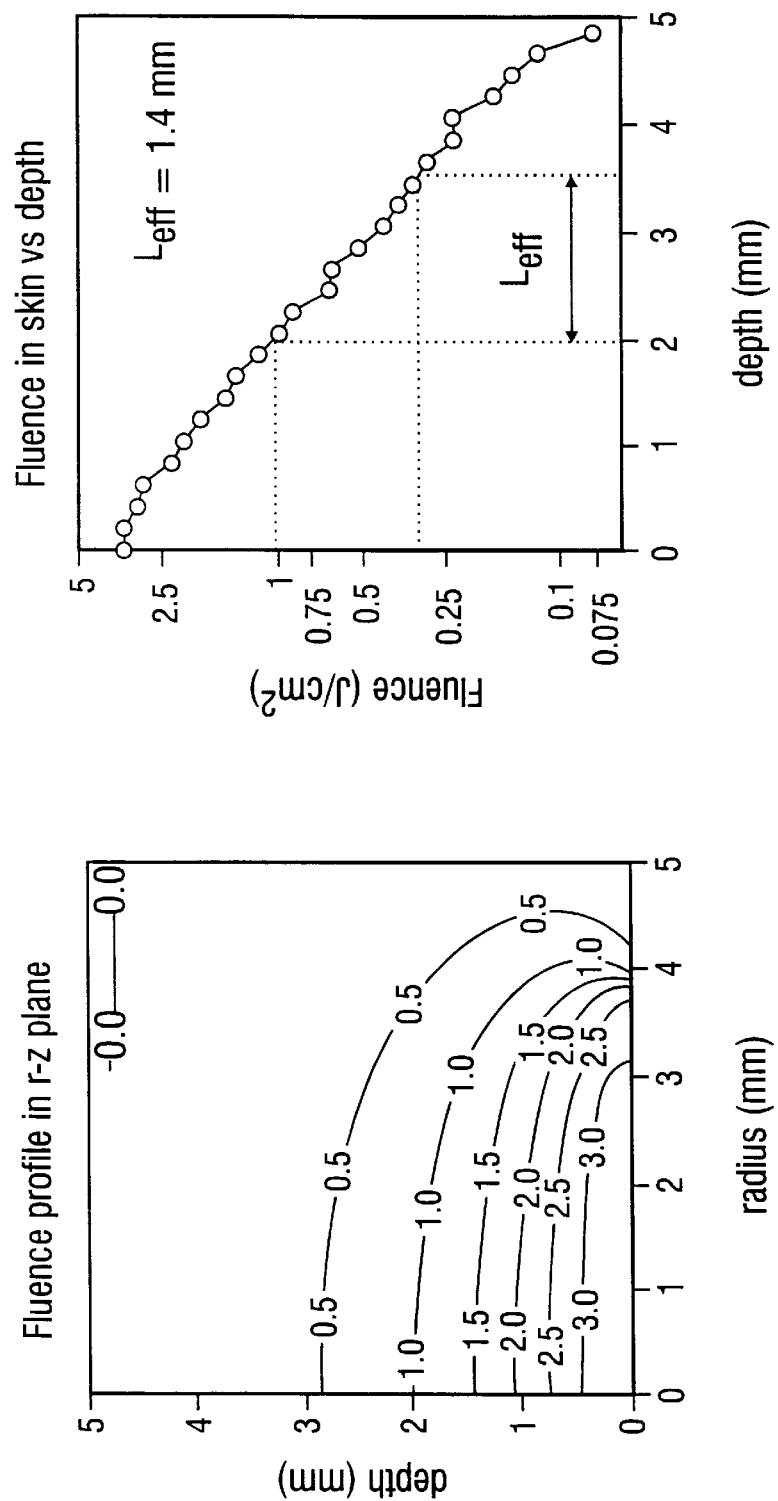
FIG. 13 is a graph showing the cross sectional profiles of fluence rates of 3.0, 2.5, 2.0, 1.5, 1.0 and 0.5 J/cm$^2$ in the r-z plane for fluence in an incident 7mm square beam of 1 J/cm$^2$ using energy per pulse of 0.5 J.
FIG. 14 is a graph showing fluence in skin at depths from zero to 5 mm for laser light having the same parameters as in FIG. 13. Fluence is shown on the y axis using an exponential log scale. $L_{eff}$ is shown to be equal to about 1.4 mm.

FIG. 14 is a graph showing the results of measurements over the period from days 4 to 12 post lasing to determine the average length of hairs below the skin surface for the four subjects wherein -●- represents the average length of the unlased hairs (controls) for the four subjects, and -■- represents the average length of the lased hairs for the four subjects. These results show that the shortening of the hair duct (as occurs during telogen phase) had begun as early as four days post lasing.

EXAMPLE 3

Monte Carlo simulation studies were conducted using known methods to calculate the actual fluence profile in human skin or flesh when the skin surface is illuminated with a Nd:YAG laser having a wavelength of 1.06 microns, with fluence in the incident beam of 1 J/cm$^2$, and energy per pulse of 0.5 J.

Optical and geometrical properties at the wavelength value of 1.06 $\mu$m are summarized in Table 3 below:

TABLE 3

Optical Properties for skin model

|  | $\mu_a$ | $\mu_s$ | g | n | depth (mm) |
|---|---|---|---|---|---|
| Epidermis | 2 | 300 | 0.85 | 1.4 | 0.065 |
| Dermis | 1 | 100 | 0.85 | 1.4 | Infinite |

The effective penetration depth ($L_{eff}$) of light into tissue is estimated in general light diffusion theory as follows:

$$L_{eff} = [3\mu_a\mu_s(1-g)]^{-\frac{1}{2}}$$

Utilizing the data from the Table 3, the calculated penetration depth ($L_{eff}$) in dermis is about 1.5 mm.

In the model, a collimated laser beam is incident on the skin at a right angle to its surface. The skin model consists of two domains, which imitate the properties of the epidermis and dermis. The epidermis is considered as an infinite slab 65 $\mu$m wide. The dermis is considered as a semi-infinite domain having a common plain interface with the epidermis and extending infinitely along the interface.

Simulation Method

Propagation of light in skin was simulated by the Monte-Carlo (M-C) method, in which absorption and scattering phenomena in highly light scattering media has been properly accounted, as well as refraction and reflection of light at the interfaces. Software utilizing known mathematical formulae was used to make the calculations.

In simulation, the tissue was divided into a 3D array of small (0.2 mm on a side) cubic volume elements, the amount of light energy absorbed inside each element was estimated, and the local energy fluence rates were retrieved to enable a 3D representation of the radiation level within the tissue. In this way, fluence rates in both vertical (radius-depth or r-z) and horizontal (x-y) cross-sections were estimated and displayed in contour plots. In all simulations, the origin was on the skin surface in the center of symmetry of the incident beam. Depth was measured from the epidermis-air interface into the tissue.

For economy of time, the simulation procedure was divided into two stages. The first stage included M-C simulation of fluences in a selected cross section with a 0.2×0.2 mm² (pixel) incident beam and a fluence rate in the beam of 1 J/cm². At the second stage, a desirable beam shape was approximated with square beam pixels, and then fluences were added up to calculate ultimate fluence rate for each particular beam profile and cross section.

For different skin models or reflector conditions, a new M-C simulation with pixel beams was performed. Results of simulations obtained by the two stage method has been shown to be identical to those generated with conventional M-C, other conditions being equal.

Cross sectional profiles of fluence rates in the r-z plane of 3.0, 2.5, 2.0, 1.5, 1.0 and 0.5 J/cm² were plotted for fluence in the incident beam of 1 J/cm² using a 7 mm diameter round beam with energy per pulse of 0.5 J. A plot of these fluence profiles is shown in FIG. 13.

FIG. 14 shows a plot of fluence in skin at depths from zero to 5 mm for laser light having the same parameters as in FIG. 13. Fluence is shown on the y axis using an exponential log scale. $L_{eff}$ is shown to be equal to about of 1.4 mm.

The methods of this invention provide several advantages. When the papilla is in a position proximate the skin surface, it is more easily reached by light energy administered to to the skin surface, and thus is more susceptible to damage at low fluence, i.e., in the range from about 3–5 J/cm². Because stem cells are more susceptible to long term damage when they are activated, increasing the percentage of the hairs in late telogen/early anagen phase increases the number of hairs in any given section of skin that are sufficiently damaged by such techniques to effect long term inhibition of hair growth. Thus, by utilizing the pretreatment method of this invention, the energy required to effect permanent hair removal is minimized because the distance below the surface of the skin to which light energy must penetrate during a hair removal treatment is minimized, and the percentage of hairs for which the future growth is significantly inhibited can be increased. Both goals are attained while minimizing undesirable damage (burning) of surrounding tissue.

No. 2: Methods and Devices for Infiltrating Contaminant in Laser-Assisted Hair Removal Many hair removal procedures involve application of a contaminant containing light-absorbing particles to the surface of a section of skin for the purpose of inhibiting the growth cycle of hairs in the skin section, or for long term inhibition of hair growth in a skin section. The skin section and hair ducts therein containing the contaminant are illuminated by a beam of light at a wavelength absorbed by the contaminant for the purpose of (1) driving particles in the contaminant into the lower region of hair ducts (propulsion phase) and (2) causing the particles to heat up (thermal phase). Heat is thereby delivered preferentially to hair growth cells at the base of the hair ducts. However, it is difficult to produce a net downwards vector on a particle sufficient to drive it into the depths of the hair duct because light incident upon a skin surface is randomly scattered and absorbed during passage through the epidermis and dermis of the skin. In addition, sebaceous glands in hair ducts tend to exude a sticky wax-like substance that impedes movement of chromophore particles into the base of the hair ducts.

In addition, the skin structures that are targets of various laser treatments are found at different depths in skin. It is known to vary the wavelength of the laser beam to control the depth to which a laser beam penetrates into skin so as to direct laser energy only so deeply into skin as is necessary to affect the skin structure that is the target of a laser-assisted skin treatment. Further methods of controlling the depth of penetration of a laser beam into skin would be advantageous.

One aspect of the invention solves this problem by providing an improved method for infiltrating light-absorbing chromophore particles into hair ducts using laser illumination. In one aspect of the invention, a mask is interposed between the light source and the skin section to be treated, and receives an incident large laser beam, but transmits a plurality of small laser beams spaced so as to prevent merging of the beams in the skin surface. These small beams are used to create an energy profile with depth in skin that is useful for creating a net downward force on illuminated chromophore particles in hair ducts to drive the particles into the depths of the hair ducts. In another aspect of the invention, an array of lenses is substituted for the mask to transform an incident large laser beam into a plurality of small beams spaced so as to prevent merger of the small beams.

A beam of light incident upon a skin surface is progressively attenuated with increasing depth due to absorption and scattering of photons. The gradient in skin of energy attenuation depends upon the beam size. The gradient of energy attenuation is relatively flat if the beam of light is relatively large (i.e. 7 to 8 mm in diameter). Photons that penetrate skin without absorption (i.e., such as those provided by a Nd:YAG laser) tend to be randomly scattered during passage. Due to the random scattering effect, photons tend to strike a particle of contaminant in a hair duct or other skin structures from all directions. In the case of a relatively large beam, a particle is bombarded with photons of comparable energy on all sides, making it difficult to create a net downward vector on an illuminated particle of contaminant, even if some parts of the particle are exploded by the light energy.

It has now been discovered that a small beam of light having a spot size in the range from about 0.5 to 1.0 mm in diameter is attenuated more rapidly with depth than one of larger diameter (e.g., 8 mm in diameter). Thus, the size of the light beam controls the depth at which follicles and other skin structures are affected by a light beam. For more shallow effect, the beam spot size is decreased. As shown in FIG. 15B, the gradient of energy attenuation in skin is correspondingly steeper for small beams, with the steepness of the energy gradient progressively increasing as the beam spot size decreases. Therefore, either a single small beam producing a spot size in the range from about 0.5 to 1.0 mm in diameter or a plurality of small beams of light of such size establish in skin a steep light energy gradient having rapid attenuation with depth.

Figure 15A:
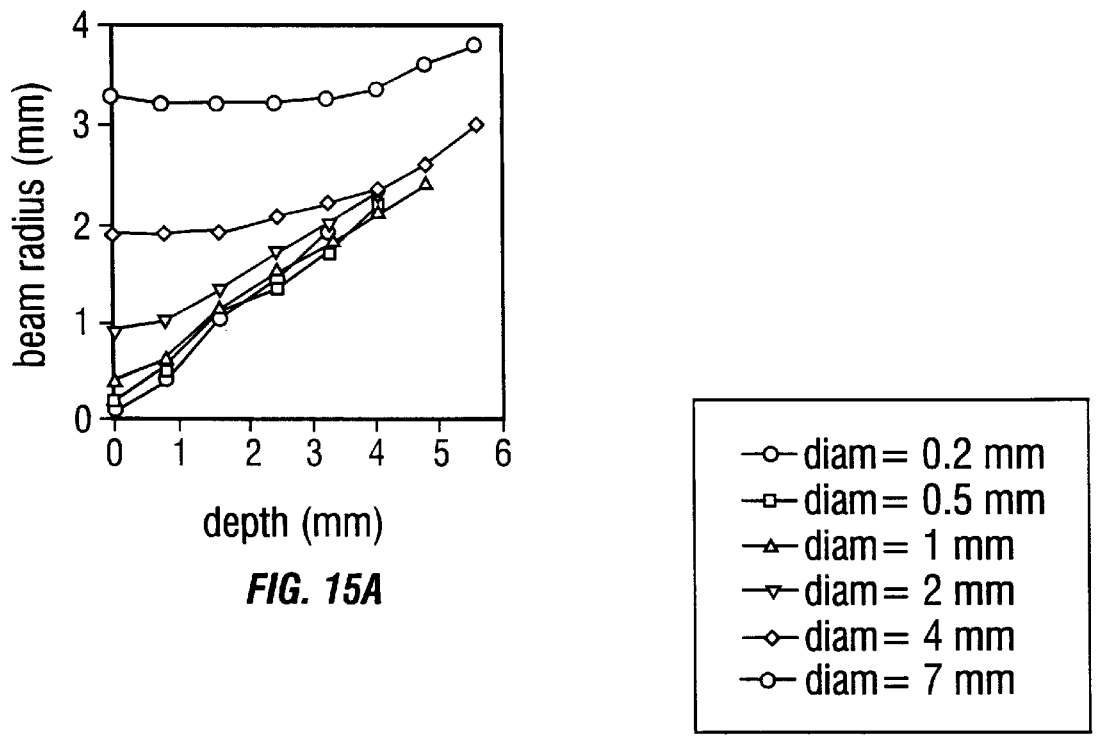
FIG. 15A is a graph showing the broadening of laser beams with fluence of 1 J/cm² of different diameter in skin with depth. -○- at bottom=diameter of 0.2 mm; -□-= diameter of 0.5 mm; -Δ-=diameter of 1 mm; -▲-=diameter of 2 mm; -◇-=diameter of 4 mm; -○- at top=diameter of 7 mm.
Figure 15B:
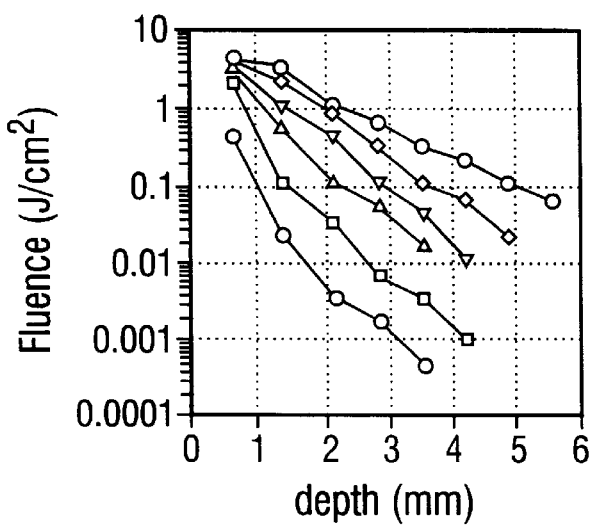
FIG. 15B is a graph showing fluence levels in the center of laser beams at skin depth for beams of different incident diameters. The incident beam has a fluence of 1 J/cm². The symbols are as in FIG. 15A.

It has also been discovered that small beams of light in this size range spread out with depth more rapidly than larger beams (FIG. 15A). Therefore, if a plurality of small beams are used simultaneously to create a steep energy gradient within skin, the small beams must be spaced apart a sufficient distance to prevent the small beams from merging beneath the skin surface and taking on the characteristics of a large composite beam. Accordingly, the plurality of small beams are usually spaced at a distance that approximates the effect of an infinite distance, for example about 0.5 to 1.0 mm between the circumference of the beam spots.

Due to the large energy gradient of attenuation established by a single small beam (or by a plurality of small beams of light having the above-described spot diameter and spacing), a photon from such a small beam imparts greater heat energy to the top region of a chromophore particle in a hair duct than a photon from the same beam that strikes the particle at a lower region. The difference in energy between photons striking the top and bottom of a particle infiltrated into skin or into a hair duct is larger, the larger the size of the particle. A photon may strike the top region of a 1 micron particle with sufficient energy to cause a small explosion, but a photon from the same small beam of light, or a photon scattered from a nearby beam of light, that strikes the bottom of the same particle may have lost sufficient additional energy in traveling through skin an extra micron in depth to be incapable of causing an explosion at the point of impact. When this effect is multiplied by a plurality of photons striking each of the chromophore particles in a hair duct, a net downward force is exerted on the particles. This net downward force is useful for driving the contaminant particle into the depth of the hair duct during laser-assisted hair removal procedures.

In view of these considerations, in one aspect of the invention a single small beam of light is rapidly scanned over the section of skin to be treated. For example a single beam having a spot diameter of 0.5 to 1 mm in diameter with a fluence of about 2.5 J/cm², with pulse energy of about 20 mJ per pulse, a pulse repetition of about 600 pulses per second, and a minimum pulse duration of about 10 ns could be used to exert sufficient force on graphite particles in hair ducts to drive a portion of the particles into the base of hair ducts. Once the particles are spread into the base of the hair ducts, the laser parameters can be adjusted to those recognized in the art as suitable for heating up the particles so as to transfer heat to tissue surrounding the hair ducts. When a single small beam is used during the propulsion phase, a different laser to provide a beam diameter of about 7 to 8 mm is generally used during the heating phase of the hair removal process.

Alternatively, to avoid having to switch lasers between the propulsion phase and the heating phase, a device can be interposed between the light source and the skin section to be treated that will transform a single large beam (e.g., one of 7 to 8 mm in diameter or a 7 mm square beam) into a plurality of small beams having the size and spacing disclosed herein. One such devise is a light-blocking mask having an opaque body with many light-transmissive, small cylindrical apertures, each with a diameter of from about 0.5 to 1.0 mm, with a distance of about 0.5 to 1.0 mm between the circumferences of the cylinders. For convenience, the mask can be adapted for attachment directly to the distal end of a laser wand.

The body of the masque is opaque and can be in any convenient overall size and shape, such as a round or square thin plate, so long as it has one surface that is adapted for contacting a skin surface. Generally the body of the mask is at least 10 times less in thickness as in overall size to prevent the sides of the cylindrical apertures from shading the skin surface as the light passes through the apertures. The apertures in the body are generally oriented perpendicularly to the contact surface of the mask. For convenience in use, the contact surface of the mask generally has an area of about 0.5 to several centimeters square and is generally smooth enough to pass over the skin surface without abrading it. The contact surface of the mask may be planar or may conform to the shape of a body part, and may be rigid or somewhat flexible.

The mask body can be made of any opaque material that will not be destroyed by laser irradiation having the energy characteristics with which the mask is to be used. Generally, the mask body is heat resistant and will not undergo a chemical reaction caused by the laser. The mask body should produce a minimum of specular reflection to avoid an undesirable effect on the laser, such as might be created if light is reflected back into the laser cavity. For example the surface receiving incident light can be roughened to reflect light in all directions. In one embodiment, the body of the mask is formed of a sheet of fluorescent paper (such as is used for aligning optics containing infra red radiation) with pinholes as apertures.

Figure 16A:
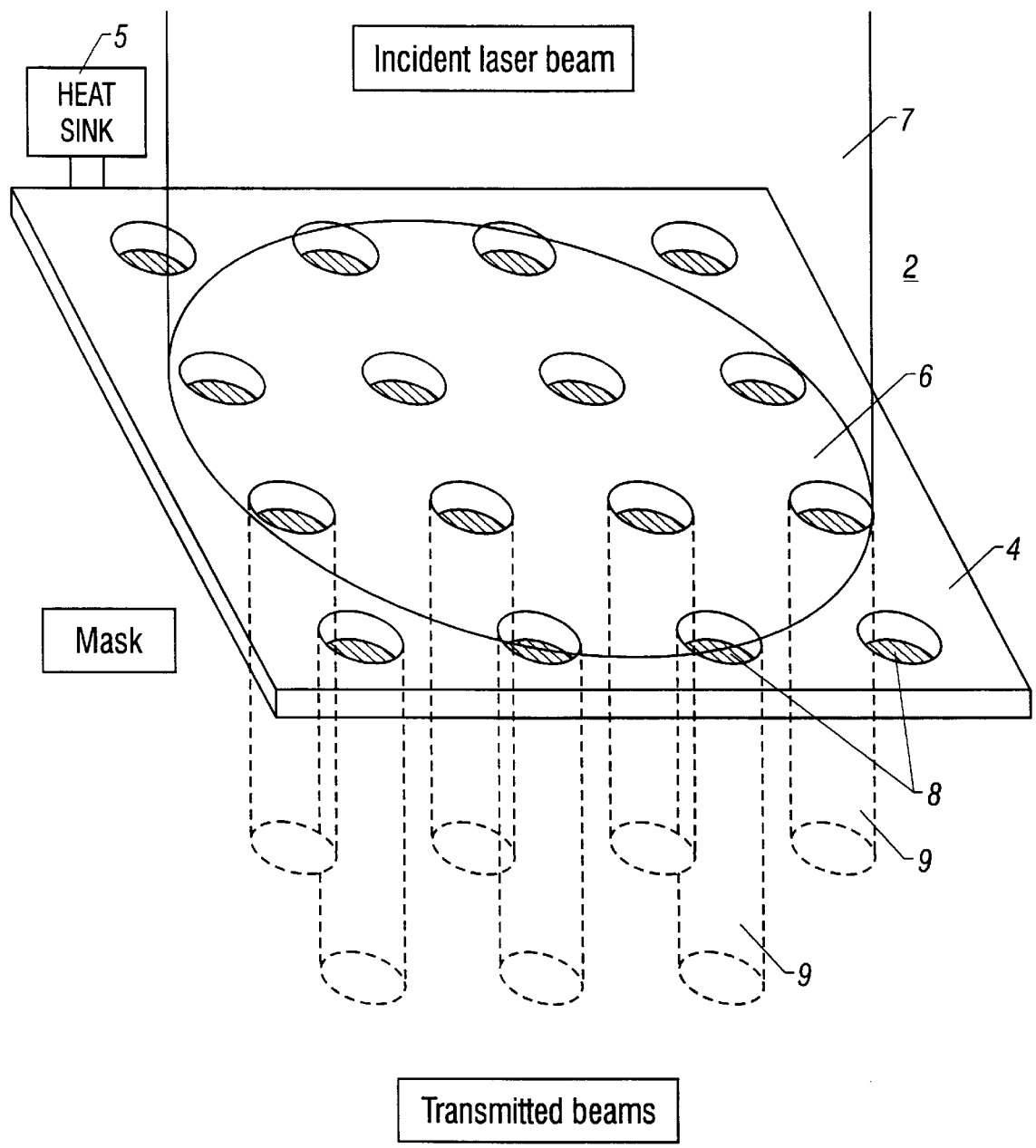
FIG. 16A is a drawing showing a mask that receives a large incident laser beam and transmits a plurality of small laser beams for infiltrating contaminant particles into hair ducts.

FIG. 16A is a drawing showing a mask 2 with a body 4 having contact area 6 and pinhole apertures 8. Incident light beam 8 is transformed by the mask into a plurality of smaller light beams 9. Attached to the mask is heat sink system 5.

In use, light from a light source, such as a laser, passes through the apertures in the mask and is directed to a skin surface and hair follicles through the small apertures in the mask, which have a diameter in the range from about 0.5 mm to 1 mm and are spaced apart at a distance of about 0.5 mm to 1 mm as measured between the edges of the apertures. The size of the apertures and their spacing or density in the body of the mask are selected to create from the large light beam a plurality of small beams. For example, a mask for use with a Nd:YAG laser having a wavelength of about 1064 nm and a beam size of about 8 mm contains round apertures with an internal diameter of about 0.4 to about 0.8 mm and an average spacing between edges of the apertures of about 0.5 to 1.0 mm.

Since the mask screens out a substantial portion of the light energy produced by the light source, several passes of the masked light source over a section of skin are required to deliver the same amount of light as does an unmasked light source. A simple calculation can be used to determine the number of passes of light delivered through a mask having apertures of any given diameter and density are required to approximate the energy delivery of a single pulse of unmasked light. The following sample calculation shows the light delivery of a mask having apertures with a diameter of 0.6 mm and a density of 60 apertures/cm$^2$:

Diameter of a hair follicle=0.1 mm;

Diameter of mask aperture=approximately 0.6 mm

Effective area S covered by a single aperture=3.14 (aperture dia.+follicle dia)$^2$ Area covered by a mask with 60 apertures/cm$^2$ after 5 passes=5×60×S=1.15 cm$^2$ By this calculation, 5 passes of a laser beam of 8 mm in diameter delivered through a mask having an aperture density of 60 apertures/cm$^2$ delivers to a single hair duct approximately the same energy as one unmasked pulse.

Therefore, several pulses delivered through the mask are required to delivery laser energy equivalent to 1 to 2 pulses of unmasked light. Generally, about 5 or 6 pulses are delivered to each section of skin treated, with the mask being shifted slightly at random between the pulses to even out the amount of illumination. In general, whatever the diameter and density of the apertures in the mask, the number of lasing passes with the mask in place is selected to deliver roughly the same amount of energy per hair duct or other target skin structure as would be received from unmasked light.

In one embodiment, the body of the mask is adapted to absorb heat from the surface of the skin during its illumination. The body of the mask can absorb some quantity of heat from the skin surface, depending upon the heat capacity of the material from which it is made. The capacity of the mask body to absorb heat can be enhanced by having one or more passageways or conduits there through in which a cooling medium is circulated to absorb heat from the skin surface. For example, at least one conduit for the cooling medium can be located around the periphery of the body of the mask in a portion of the body that does not contain the apertures. In addition, as shown in FIG. 15, any known type of heat sink system 5 can be attached to body 4 of the mask, including those provided by thermoelectric cooling, passive heat sinks, convection cooling, such as provided by fans, conduction cooling, prechilling, and the like.

When used as described herein, the mask provides the advantage of increasing the net downward force vector on light-absorbing particles in the hair ducts caused by light photons delivered through apertures in the mask. The mask also decreases the depth of penetration through skin of an incident light beam and therefore, is useful in any skin treatment in which a shallow penetration of light is required.

Figure 16B:
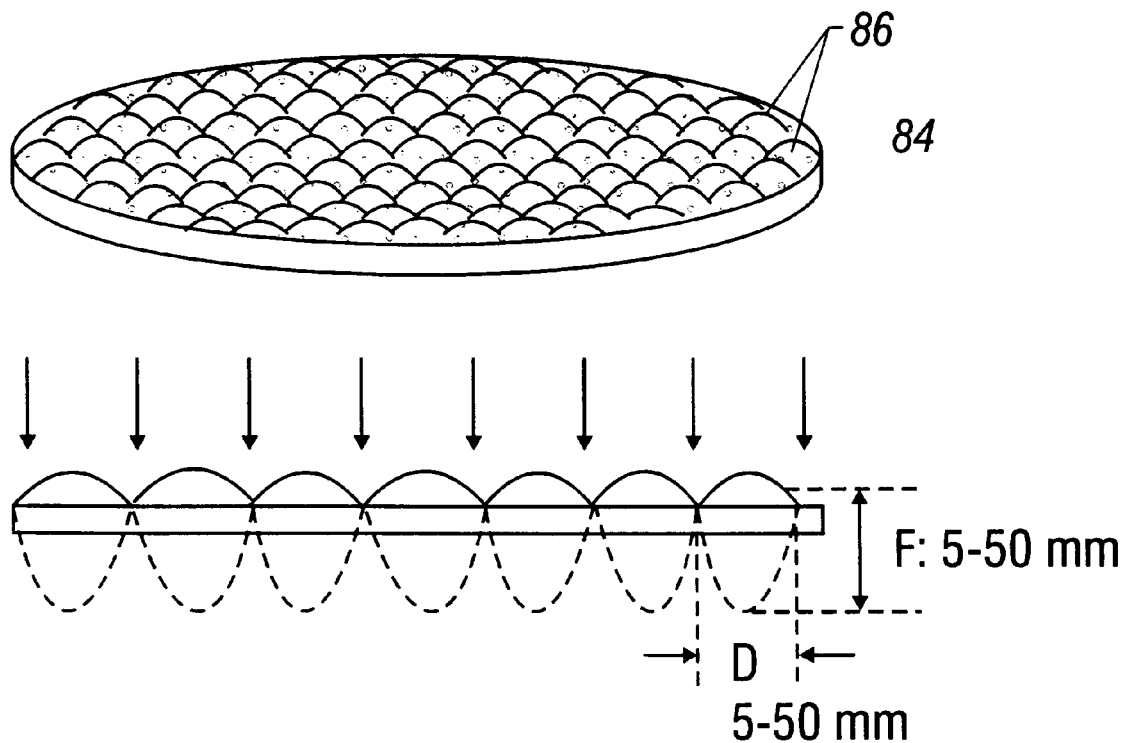
FIG. 16B is a drawing showing an array of lenses that receives a large incident laser beam and transmits a plurality of small laser beams for infiltrating contaminant particles into hair ducts.

In another aspect of the invention, an array of lenses (FIG. 16B) is substituted for the mask to transform an incident large laser beam into a plurality of small beams having the above described spot size and spaced at an interval to prevent merger of the small beams. The array includes a plurality of lenses, each having a focal length of about 5 mm to about 50 mm and a diameter of about 5 mm to about 50 mm. Although the array can have any overall shape, in one embodiment the lenses in the array are disposed to receive an 8 mm diameter incident beam and transform it into a plurality of beams having a spot size of about 0.5 mm to about 1.0 mm. As shown in FIG. 16B the array 84 is arranged circularly, with each lens 86 being semispherical in shape. The array can be either flat or curved. In use, the lenses can be disposed in either direction relative to a skin surface.

The mask or the array is adapted for attachment to a laser wand or laser arm for delivering the small beams to the skin surface during treatment by laser irradiation. Although these devices are described with reference to the advantages of creating a steep energy gradient within skin to facilitate creation of a net downward vector on particles infiltrated at some depth within skin structures, such devices can also be used to create a plurality of small beams to facilitate shallow illumination of a skin surface for any purpose, such as might be useful in a method of laser skin peeling or to affect sebaceous glands.

No. 3: A Method for Infiltrating a Contaminant into Hair Follicles Using an Occlusive Dressing Hair removal procedures are known in which a contaminant is applied to the skin surface and caused to infiltrate into hair ducts for subsequent irradiation by a light source. To effect hair removal, the light absorbing contaminant (usually containing light-absorbing particles) must be driven to a depth in the hair duct that will allow transfer of heat and mechanical energy from the particles directly to tissue surrounding the hair duct that effects hair growth, Le., the stem cells located in the bulge area and the dermal papilla of the hair duct. Generally, however, massage of the contaminant onto the skin surface causes the contaminant to infiltrate the hair ducts only for about 20 microns, yet the portion of the hair duct that contains the stem cells and/or dermal papillae is located at a depth of from about 2 to 6 mm, depending upon the location on the body where inhibition of hair growth is desired, i.e., the beard, leg, or upper lip.

The present method provides a procedure by which a contaminant, once applied to a skin surface so as to introduce the contaminant into the top region of the hair follicle, can be induced to infiltrate more deeply into the hair follicles to be treated. In the present invention, after application of the contaminant to the skin surface, but prior to illumination, the pores and infiltrated hair ducts in the skin section are occluded for a period of time ranging from several minutes to several hours, whereby further infiltration of the contaminant into the hair ducts is caused.

Figure 17:
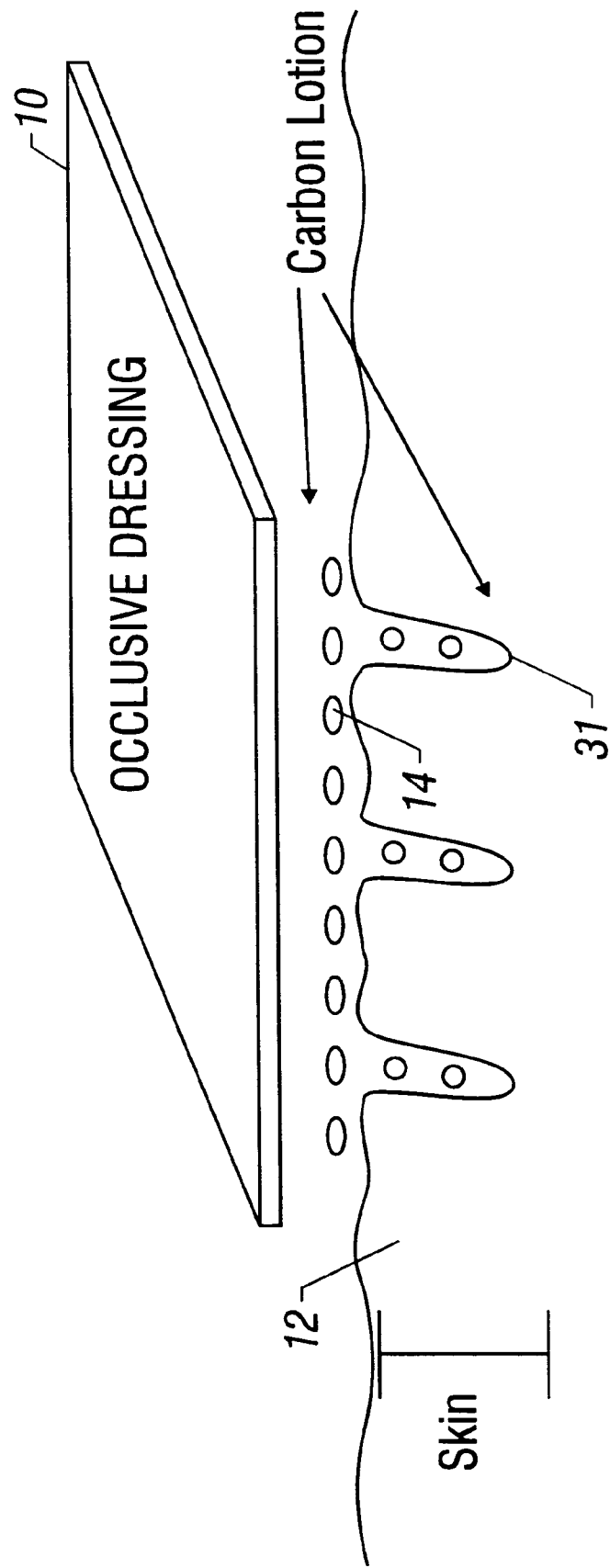
FIG. 17 is a drawing showing an occlusive dressing covering a section of skin to which a lotion containing carbon particles has been applied and infiltrated into hair ducts.

The invention is described with reference to FIG. 17, which shows occlusive dressing 10 covering a section of skin 12 to which a contaminant 14 containing particles has been applied and infiltrated into hair ducts 31. It has been discovered that when an occlusive covering is applied to a contaminated skin section for an extended period of time, contaminant in the upper region of the hair ducts is drawn into the lower portion of the hair ducts as shown in FIG. 18. Therefore, occluding the contaminated hair ducts with a covering facilitates loading of particles in the contaminant into the lower regions of the hair ducts. This discovery provides an alternative method for spreading a contaminant, such as one containing light absorbing particles, deep into the hair follicles prior to illumination so that, during illumination of the skin section, the heated particles will transfer energy to the portion of the hair cells surrounding the lower region of the hair follicle that are responsible for hair growth, particularly those in the bulge area.

Any air and water-tight covering can be used as an occlusive dressing. For instance, any type of known liquid that can be painted or sprayed onto the skin to form an occlusive covering can be used. In addition, an occlusive bandage or dressing that provides an adhesive seal at the skin surface around the perimeter of the covered area can also be used. For example, the occlusive dressing sold under the trade name Tegaderm™ bandage can be used to occlude the contaminated skin section.

Allowing the occlusive covering to remain on the contaminated skin surface for an extended period of time is sufficient to induce infiltration of the contaminant into the lower regions of the hair follicles. The period of time required will vary, depending upon the depth of the hair follicles to be treated. Once this goal has been accomplished, the occlusive covering can be removed from the skin surface, and the skin surface is ready to be illuminated to cause injury to or destruction of the cells surrounding the hair ducts that promote hair growth.

Generally, the covering is allowed to stay in place for a period of time ranging from several minutes to several hours, for example about 15 minutes, whereby infiltration of the contaminant into the lower regions of the hair follicles is induced. Infiltration is optionally further enhanced by application of a surface-wetting agent to the skin surface. A surface wetting agent will facilitate wicking of the contaminant, including any chromophore particles contained therein, into the hair ducts while the pores and hair ducts in the skin surface are occluded, i.e., while sealed with a water-barrier forming substance, or covered with an impermeable patch or bandage. The surface wetting agent can be added to the contaminant, or contained within or upon the occlusive dressing. All that is required is that the surface-wetting agent is present at the mouth of the occluded follicles during the period of time that the occlusive covering is in place.

After removal of the occlusive covering, the skin surface can be illuminated to shock or cause injury or destruction of the cells surrounding the hair ducts that promote the growth of hairs. Any of the methods of illumination that utilize a light absorbing contaminant in conjunction with a light source, such as a laser with a wavelength of light highly absorbed by the contaminant can be employed during the illumination phase. Examples of such methods and procedures, and of the most useful types of contaminants and lasers, are described in full in U.S. Pat. Nos. 5,226,907 and 5,425,728, which are incorporated herein by reference, each in its entirety.

For example, laser illumination to inhibit hair growth can be accomplished by infiltrating a contaminant containing carbon particles in the size range from about 0.01 micron to about 1 micron into hair ducts on a section of skin and then illuminating the skin surface with light from a Nd:YAG laser. Generally the temperature of the contaminant is raised to 70° C. to 80° C. for about 0.1 second by this method. Energy transferred from the heated contaminant in the hair ducts to skin tissue surrounding the hair ducts provides long term inhibition of hair growth in the hair ducts. Since the wavelength produced by a Nd:YAG laser penetrates skin with a minimum of absorption and scattering therein, overheating of surface skin tissue is avoided.

In another embodiment of the invention, the occlusive covering comprises a flat, flexible supporting scrim covered on one or both sides with a hydrogel. The scrim is generally a plastic lattice or cloth netting upon which the hydrogel is placed. The hydrogel is a three-dimensional polymeric network that can solvate a large quantity of water without dissolving. The copolymer can contain both hydrophilic and hydrophobic components. The hydrophilic monomers used are generally N-vinyl-2-pyrrolidone (VP), 2-hydroxyethyl methacrylate (HEMA), and 2 acryloylamido-2-methylpropanesulfonic acid (AMPS). Copolymerization with other hydrophobic monomers is generally carried out in the presence of crosslinking agents, such as divinyl benzene (DVB) and ethylene glycol dimethacrylate (EDMA). Examples of commercially available hydrogel-containing products suitable for use as an occlusive covering are as follows:

| Product | Hydrogel Polymer | Supporting Scrim |
| --- | --- | --- |
| Second Skin ® | Poly (ethylene Oxide) | polyethylene (PE) nonwoven scrim (Mfg. Spenco) interlayer with peelable polyethylene backing |
| CuraGel | HEMA:PEG:N═C—O | nonwoven cotton gauze on-elastomer (Mfg. Kendall) substrate with PE backing |
| TTL Medical | HEMA:PEG:N═C—O | isolated nonwoven fibers. On elastomer (semi-occlusive urethane dressing) substrate with PE backing |

Hydrogels are composed mostly of water, for example greater than 80% by weight, immobilized in a matrix of a hydrophilic crosslinked polymer. One of the unique characteristics of hydrogels is that, due to crosslinking of the polymer system, they do not dissolve in the water they hold. The result is "trapped water" held by solvation to the hydrophilic portions of the hydrogel. To take advantage of these characteristics, when a hydrogel is used as the occlusive covering in the practice of this invention, it is usually not removed prior to lasing. Therefore, preferred hydrogels are those which provide optimal optical transmissivity and form a minimum of toxic products during lasing. Urethane gels may contain unreacted isocyanates, which have a distinct odor, and present a possibility that potentially hazardous pyrolites can be formed upon lasing, such as is formed by cleavage of common aromatic isocyanates. Consequently, the "urethane" type of HEMA:Poly(Ethylene Glycol):isocyanate hydrogel is useful, but poly (ethylene oxide) hydrogels are preferred if the hydrogel is to remain in place during lasing. Such PE hydrogels contain no hydrogen atoms and cannot form toxic by-products.

One of the advantages of leaving the hydrogel in place during lasing is to contain the contaminant and drive the contaminant downwards within the hair ducts. FIGS. 18A–18F illustrate how these advantages are achieved. If the occlusive dressing is removed, force vectors generated during lasing may spill the contaminant out of the hair follicle (shown in FIG. 18C).

Figure 18A:
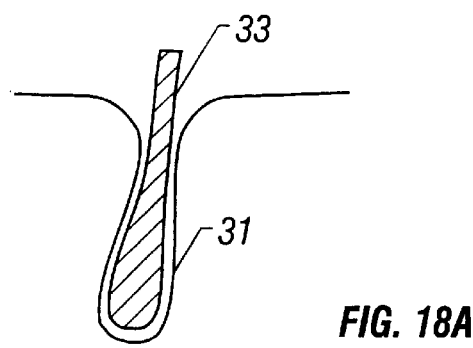
FIG. 18A is a schematic drawing showing a hair within a hair follicle.
Figure 18B:
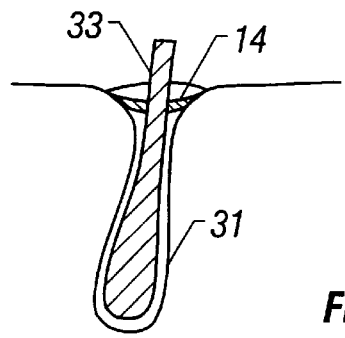
FIG. 18B is a schematic drawing showing a contaminant lotion applied to the opening of the hair follicle of FIG. 18A.
Figure 18C:
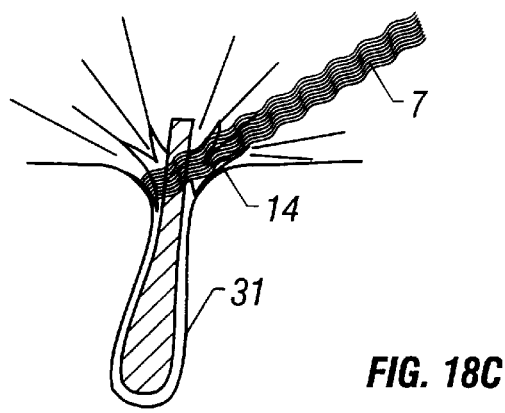
FIG. 18C is a schematic drawing illustrating that during laser irradiation, some forces are not directed into the follicle. Certain inertial and fluid effects prevent delivery of the contaminant into the bottom of the hair follicle.
Figure 18D:
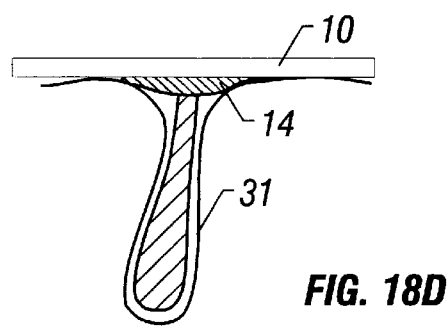
FIG. 18D is a schematic drawing showing the embodiment wherein a hydrogel barrier is applied over a contaminant layer.
Figure 18E:
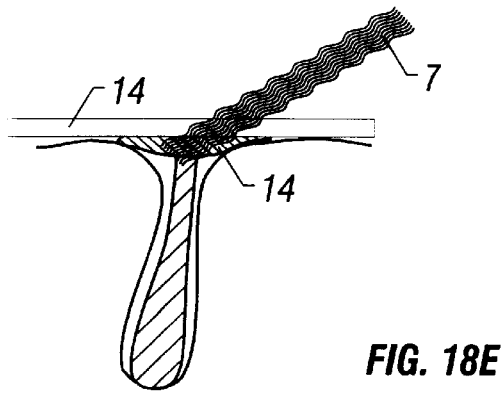
FIG. 18E is a schematic drawing showing that, upon illumination, the hydrogel layer confines the pressures and shock so that the contaminant is directed into the hair duct around the hair.
Figure 18F:
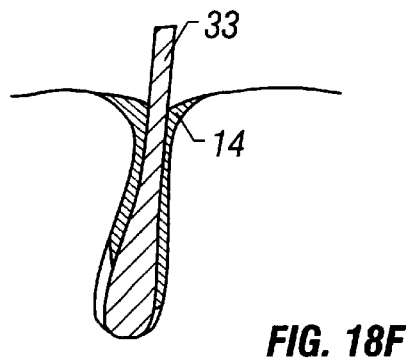
FIG. 18F is a schematic drawing showing the contaminant delivered deep into the hair duct surrounding the hair.

During lasing a short pulse of energy vaporizes some of the contaminant, and a puff of smoke and fragments is produced, which fly off the skin surface as smoke or particles. In the present invention, the hydrogel serves as a blast barrier, to confine the smoke and fragments so formed. A particle or fragment in a hair duct is forced downward into the hair ducts (FIG. 18D). In addition, a portion of the water in the hydrogel evaporates, providing an additional instantaneous overpressure, shock, and acceleration to aid in propelling the chromophore into the depth of the follicle. Steam so created may instantaneously lift the hydrogel from the skin surface, but unvaporized water remaining in the hydrogel rapidly cools the laser-induced steam back to water, causing the hydrogel to "slap" against the skin surface. This "slap" may help propel the contaminant into hair follicles. Because the water content of the hydrogel is not compressible, it acts like a solid to the extent that it confines the force vectors of an exploding contaminant particle much in the same way that a sheet of plastic or glass placed over the skin surface prior to lasing would do (shown in FIG. 18E). Therefore, the hydrogel directs the energy of the ablation or explosion downward, helping to force the contaminant into the depths of the hair ducts (FIG. 18F).

The water in the hydrogel, which has a high specific heat, can absorb heat generated during lasing. As the hydrogel lies atop the skin to be treated, its heat absorbing properties afford a unique means for preventing overheating of dermal tissue during laser hair removal techniques of all types. Further, it has been discovered that the hydrogel can be precooled or even frozen prior to application to the skin surface to provide an extra measure of cooling to the dermal tissue prior to the lasing phases of any hair removal procedures. A hydrogel dressing can be used to cool the skin surface whether the cooled or frozen occlusive dressing is removed during lasing or not. Studies have shown that light is satisfactorily transmitted through a hydrogel dressing when the hydrogel remains in place during lasing.

No. 4: A Soothing Topical Hydrogel Dressing

Many patients experience some discomfort for a day or two following laser skin treatments, such as treatments for skin rejuvenation or to inhibit growth of hair. There are many types of prior art bandages and skin patches that can be applied to skin surfaces and which release active agents useful for reducing minor irritation, inflammation and pain. One such device disclosed in U.S. Pat. No. 5,474,528 is a hydrogel skin patch that releases a photoactivated pharmaceutical agent to skin when illuminated with light, for example during laser therapy. However, it would be useful to have a hydrogel composition for application to skin that releases active agents for soothing and comforting irritated and inflamed skin without recourse to light energy. Such a composition would be particularly useful after laser therapy to reduce and/or alleviate irritations and inflammations.

The present invention is a soothing dressing for irritated skin comprising a cross-linked polymeric hydrogel matrix into which has been infused a hydrating agent, such as water, and an active agent useful for eliminating or alleviating a skin irritation, sensitivity or reddening. The hydrogel matrix can be made of any species of the wide classes of hydrogels, including but not limited to, polymers of acrylates, ethylene oxides of various molecular weights, vinylpyrrolidones, natural chitins, lectins, and various copolymers thereof. In one embodiment of the invention, the hydrogel matrix includes a sufficient amount of an adhesive hydrogel that the hydrogel dressing will self-adhere when applied to skin. U.S. Pat. No. 5,143,071 to Keusch et al. cites an extensive list and description of prior art adhesive hydrogels that adhere to skin surface with an intimate physical contact. Generally, the polymeric hydrogel will contain up to 84 percent by weight of water when fully hydrated. For example, the hydrogel can contain from about 60 percent to about 84 percent by weight of water, or from about 40 percent to about 60 percent by weight of water or other hydrating substance, such as an active agent in an aqueous solution.

The hydrogel dressing may further comprise a scrim with a hydrogel lining one or both sides of the scrim. The scrim is generally a plastic lattice or cloth netting for supporting the hydrogel, as described in Section No. 3 above. It is also contemplated that the hydrogel dressing can comprise two or more hydrogel layers bonded together along their faces, such as is described in Section No. 3. Such a scrimless composite hydrogel is more flexible than those with internal scrims and better suited to conform to body contours.

The hydrogel further comprises one or more of any type of active agent that would be beneficial for soothing and/or protecting reddened, irritated or inflamed skin. For example, the active agent can be an over-the-counter drug or folk remedy that serves as a mild antiseptic, an anti-inflammatory agent, or a topical anesthetic. Examples of useful active agents include benzocaine, hydrocortisone or hydrocortisone diacetate, aloe vera extract (available in freeze-dried form), and vitamin E. Rose oil is an example of a naturally soothing oil with a pleasant fragrance that can be added to the hydrogel as a perfume. Water soluble active agents are dissolved into water and the solution is used to hydrate the hydrogel. Oily active agents can be emulsified and the emulsion can be dispersed into an aqueous component for use in hydrating the hydrogel.

The soothing action of the active agents is greatly enhanced by effective delivery of the agents from the aqueous medium. Introduction of the active agent from the hydrogel into hydrated skin tissue, or through the hydrated stratum corneum, can be by diffusion, by absorption, or by any other mechanism constituting chemical permeation or penetration of the hydrated skin or stratum corneum. It is well established in the literature of chemical transport through skin that hydration can enhance the chemical transparency, transmissiveness, passage, or transport of pharmaceuticals through the stratum corneum. A review of the subject of enhanced transport of chemical agents across the stratum corneum in hydrated skin is found in Ghosh et al., *Pharmaceutical Tech.,* April 1993, which is incorporated herein by reference.

When hydrated, the hydrogel dressing forms a thin relatively transparent layer on the skin surface. If the hydrogel layer that is placed against the skin is one of the mildly adhesive tacky hydrogels disclosed above, the hydrogel dressing is self-adhering and is relatively unobtrusive on the skin. This type of self adhesive hydrogel dressing is much less noticeable from a few feet away than a reddened mask of irritated skin. A tacky hydrogel will adhere to skin so that the dressing will continue to release the active agents over a period of many hours, for example about 8 to about 24 hours. Alternatively, any suitable adhesive known in the art can be used to affix the hydrogel dressing to a skin section to be treated so that it will remain in place until it is removed by the patient, or falls apart in the shower or by wear and tear. However, care should be taken that as much as possible of the outer surface of the hydrogel dressing is not covered by the adhesive, but is exposed to the ambient air during the time the dressing is worn by the patient. With this precaution, the hydrogel dressing will administer the soothing active agent(s) to the skin to be treated over an extended period of time in slow release as the water in the hydrated hydrogel slowly evaporates due to contact with ambient air and the body heat of the patient. Natural evaporation of water from the hydrogel dressing, which can be re-wet from time to time, provides an additional cooling and soothing effect to irritated skin.

The hydrogel dressing of this invention provides an improved slow release vehicle for administration of soothing active agents to a skin surface without application of light to the dressing. The dressing is less obtrusive visually than standard gauze and tape dressings, and is specifically designed to be used following cosmetic laser skin treatments, such as treatments for hair removal or skin rejuvenation.

No. 5: Exposure-Indicating Hydrogel Composite for Laser Applications

During application of a laser to a skin or tissue surface, certain cell particles and pathogens contained in the treated tissue, such as viral particles, may become air-borne. In addition, some degree of smoke and/or odor may be produced. It is known to cover the tissue to be lased with a transparent film or hydrogel to reduce the level of air-borne skin products that may put the laser operator at risk. However, such coverings obscure the treatment site so that it is difficult to see and keep track of which areas have been treated and which have not.

The present invention provides a scrim-less hydrogel with an exposure-indicating layer for covering a surface area to be treated by laser. Hydrogels, being mostly water, are fragile and have little tear strength. In certain hydrogels, a supporting scrim, which is usually a plastic lattice or cloth netting, provides a structure upon which the hydrogel is placed, along one or both sides. The supporting structure within these prior art hydrogel compositions absorbs some energy from the laser. More importantly, the interior scrim limits the elastic modulus of the hydrogel and, hence, its ability to conform well to the contours of a body upon which it is placed for use as a covering.

In the present invention, the supporting interior scrim is eliminated to reduce laser energy absorbed by the composite hydrogel, for example, when laser energy is administered to a skin or tissue surface covered by the composition to reduce air-borne particles and/or to aid in propulsion of a contaminant into hair ducts. Rather than having an interior scrim, the composite hydrogel of the present invention contains at least two hydrogel layers firmly attached or bonded together along their faces. The attachment can be of any type that forms a substantially transparent bond between the two hydrogel layers, for example by lamination. It is preferred that the bond between the hydrogel layers have an absorbence coefficient of no more than about 1% to about 5%, or an optical transmission of from about 95% to about 99%.

Figure 19A:
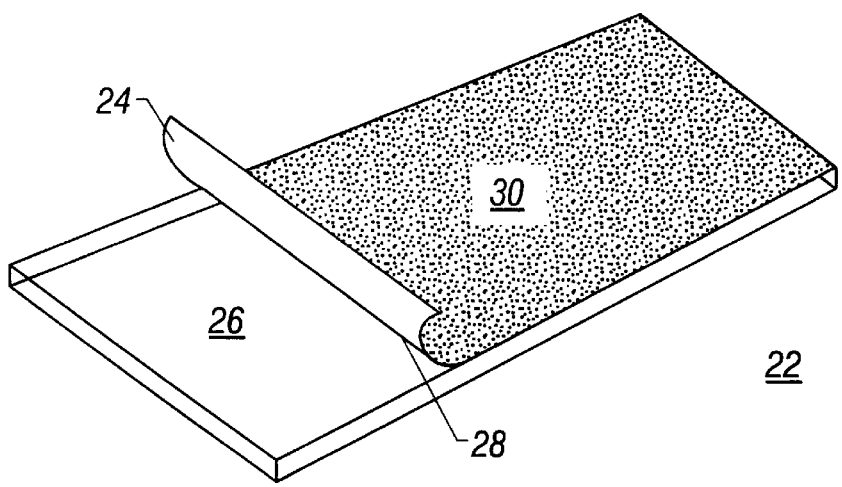
FIG. 19A is a schematic drawing of the composite hydrogel showing film 24, layer 26, and coating 30 of an indicator material in an open work pattern.

The composite hydrogel is described with reference to FIG. 19A as follows. The hydrogel composite 22 comprises at least two hydrogel layers. One of the two layers is a film 24 of a thermoplastic or solution-cast hydrogel polymer with fewer hydrophile sites in its architecture than is used for the material which comprises the bulk of the laminate, the hydrogel layer. The hydrogel film is selected to allow a maximum water uptake or swelling of about 15% to about 25% by weight. The composition of the thermoplastic hydrogel film is selected to provide tear strength to the composite hydrogel sufficient to withstand application of the composite to a contoured body surface while maximizing the elastic modulus of the composition. The second of the two layers is a layer 26 of crosslinked polymeric hydrogel. Such crosslinked polymeric hydrogels will typically hydrate and swell to a water content of about 75 percent to about 95 percent by weight of water. One face of the thermoplastic hydrogel film and of the polymeric hydrogel layer are permanently attached or bonded together so as to minimize the light absorbence at the bond 28.

The thermoplastic hydrogel layer is referred to as a "film" while the cross-linked polymeric hydrogel is referred to as a "layer" to indicate the relative thickness of the two layers. Generally the film is no greater in thickness than is required to hold the composite hydrogel together during use. Excess thickness in the thermoplastic hydrogel will impair the flexibility of the composite and its ability to conform readily to contoured body surfaces. Generally, the total thickness of the composite hydrogel is in the range from about 2 mm to to about 5 mm.

To indicate the track of the laser beam over the surface of the hydrogel composite during use, in one embodiment shown in FIG. 19 the exterior surface of the thermoplastic hydrogel film (i.e., the one not attached to the layer of crosslinked polymeric hydrogel) has a coating 30 of an indicator material. The coating can be partial, for example in a discontinuous or openwork pattern. Alternatively, the coating can be eliminated if the hydrogel film incorporates an indicator material such as a photoactivated dye or chemical. The indicator material is selected to change color upon illumination with at least one frequency of light, such as is provided by a laser. For use with any known laser, the indicator material is selected to change appearance, for example, change color, when subjected to the light of the laser to be used.

The indicator material and its pattern of coating should be selected to perform its indicator function while absorbing a minimal amount of light energy. For example, the coating of indicator material can be a partially metallized surface, such as is formed by vacuum evaporation of aluminum or other metal space. It has been found that vapor-deposited metal films, for example of aluminum or vacuum-coated bismuth, change appearance when illuminated by infrared such as is provided by a Nd:YAG laser at a wavelength of about 1 micron.

Figure 19B:
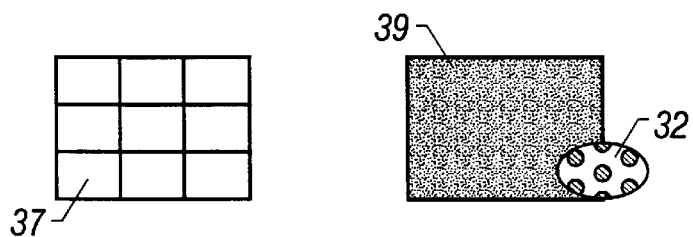
FIG. 19B is a drawing showing samples of open work patterns for the coating of indicator material in dots 32, intersecting lines 37 and cross-hatched lines 39.

The indicator material can also be a photoresponsive pigment, such as iron oxide, rhodamine red, or phthalocyanine blue, printed over the exterior surface of the thermoplastic hydrogel layer in an open-work pattern, such as a pattern of dots 32, intersecting lines 37, or cross-hatched lines 39, as shown in FIG. 19B. Certain pigments, such as Monastral Blue™ (phthalocyanine) and bismuth trioxide will react to infrared light. Monastral Blue™ pigment also changes appearance when illuminated by light in the visible region, for example under the red light of a ruby laser. Bismuth trioxide or bismuth subcarbonate, rather than being "bleached" by the laser energy, are reduced to the metal by the light, resulting in a darkening of the lased area. This phenomenon can be beneficial for blocking exposure of the lased area of skin upon subsequent passes of the laser, if desired.

To minimize the laser absorption of the open-work pattern, it can be printed in a half-tone, for example a fine half-tone. Generally the ratio of the surface area covered by the indicator material to that not covered by the indicator material (e.g. the open spaces between the dots) is in the range from about 1:5 to about 1:10. It is preferred that the area not covered by the indicator material be about 90%, or more, to allow visualization of the laser-affected areas while minimizing attenuation of the therapeutic radiation. The object is to deposit only enough indicator material on the surface of the hydrogel film to be visible to an operator, but not enough to substantially reduce the therapeutic radiation reaching the patient.

Examples of crosslinked polymeric hydrogels and thermoplastic hydrogels suitable for use in making the thin film 24 of the composite hydrogel include elastomeric polymers, such as polyurethane, having hydrophilic sites in the polymer molecule of polyethylene glycol and a molecular weight of less than about 1,000 units, for example from about 400 to about 600 units. The supporting film does not imbibe as much water as hydrogel layer 26, but retains its ability to transport water to the air, allowing some evaporative cooling and oxygen transfer to take place. Examples of hydrogels suitable for making layer 26 of the composite hydrogel include any of the commercial classes of hydrogels, such as the urethane type having hydrophilic sites comprising polyethylene oxide and a molecular weight of from about 1,000 to about 2,000 units. Alternatively, any of the common commercial classes of hydrogels can be used for layer 26, such as a hydroxyethyl methacrylate or a electron-beam crosslinked high-water content polyethylene oxide hydrogel, such as is sold by Thermedics, Inc., Woburn, Mass. Generally the hydrogel used for making layer 26 is capable of imbibing greater than about 80% by weight of water. Because of supporting film 24, certain tear-resistant polyethylene oxide types of hydrogel that have not been cross-linked by an electron beam have been used in prototypes of these laminates. Due to the high water content of layer 26, the composite hydrogel is flexible and readily conforms to body contours.

The water imbibed by the hydrogel composite can optionally contain an active agent for alleviating pain, reducing irradiation, etc. During use, laser irradiation will aid in releasing the soothing active agent to the skin surface. Examples of active agents useful for soothing skin are described in Section No. 3 of this application.

Methods of making hydrogel compositions are known in the art and are not repeated herein. One skilled in the art can readily modify existing methods to fabricate the exposure-indicating hydrogel composite of this invention. For example, in one embodiment, the composite hydrogel is obtained by a method comprising the following steps. A film is extruded of one or a combination of thermoplastic hydrogel polymers that typically hydrate and swell to contain a water content of about 15% to about 25% by weight of water. The extruded film is laminated to a preformed layer of a crosslinked polymeric hydrogel that will hydrate and swell to contain a water content of about 75% to about 95% by weight of water. The remaining free surface of the thermoplastic hydrogel film is coated in an open work pattern with an indicator material that changes appearance upon laser irradiation, but absorbs a minimal amount of light energy. If the indicator material is a metallic substance, such as aluminum, the coating can be applied using a technique of vacuum evaporation. If the indicator material is a photoresponsive pigment, such as iron oxide, rhodamine red, or phthalocyanine blue, the coating can be printed in an openwork pattern, such as a pattern of dots or intersecting lines. One skilled in the art will be able to select an indicator material that is activated by the light of the particular laser wavelength desired for use in a skin treatment process. All that is required is that the indicator material change appearance when illuminated by a laser with the particular wavelength of light selected for use without being completely photo-ablated from the surface of the composite hydrogel.

In use, the exposure-indicating hydrogel composites of this invention are hydrated and placed over a skin surface for laser treatment, with the free surface of the crosslinked polymeric hydrogel layer against the surface of the skin. The surface of the composite with the coating of indicator material does not contact the skin surface, but faces away, so that the indicator material can be readily seen by a laser operator. A light beam to be applied to a skin surface is transmitted through the hydrogel composite to a skin surface with which it is in contact. As the light of the light beam strikes the indicator material, the track of the beam causes a photoactivated change of appearance in the indicator material. As a result, an operator can readily determine exactly which areas of the skin or other tissue covered by the hydrogel composite have been treated by the light beam. The hydrogel composites are particularly well suited for use as an occlusive dressing in the methods described in Section No. 3 above, in which the occlusive dressing aids in propulsion of chromophore particles into hair ducts and other skin structures.

When hydrated and placed over a skin surface prior to treatment with a light beam, the exposure-indicating hydrogel composites described herein cool the skin surface by evaporation of water from the hydrogel, and prevent generation of air-borne particles of tissue. In addition, they absorb less light energy and conform more readily to body contours than do hydrogels that contain an interior scrim. Due to a photoactivated appearance change caused by the laser in the indicator coating, such as a color change, these compositions offer the additional advantage of recording the track of the laser over the skin surface to aid the laser operator in keeping track of which areas have been treated, and which have not. In methods of hair removal or skin rejuvenation, these composite hydrogels can also be used to aid in the propulsion of chromophore particles into hair ducts for use in inhibiting hair growth, or beneath surface skin cells to be removed in skin peeling operations.

No. 6: A Method for Controlling Thermal and Mechanical Damage During Laser Hair Removal by Selecting Chromophore Particle Size Hair removal techniques are known that rely upon the transfer of heat energy to hair follicles to inhibit hair growth. By raising the temperature of tissue surrounding the hair ducts and maintaining it at the elevated temperature for a sufficient period of time, the target tissue is destroyed, e.g., by thermal coagulation of the hair follicle and of tiny blood vessels that nourish the follicle.

In laser treatments to inhibit hair growth, it is known to infiltrate a contaminant containing light-absorbing chromophore particles into hair ducts, and then illuminate the skin surface containing the contaminant-filled hair ducts with short pulses of light at a wavelength absorbed by the contaminant. Chromophore particles absorb short pulses of high energy light and either explode, releasing the energy in the thermal and mechanical forms, or do not explode and transfer the absorbed energy in the form of heat to surrounding tissues by thermal conduction. It would be advantageous to control the delivery of mechanical and/or thermal damage to the tissue surrounding hair ducts with the goal of inhibiting future growth of unwanted hair while avoiding significant damage to the surface of the skin.

Whether pulses of light having a given pulse duration and fluence will cause a chromophore particle to explode or heat up depends upon the size of the particle. In one embodiment of the invention, the chromophore particle size is selected to preferentially induce either thermal or mechanical damage to the tissue surrounding hair ducts into which a contaminant containing chromophore particles is infiltrated for use in a hair removal procedure. In other embodiments, the particles in the contaminant have two different sizes or a bimodal size distribution with the portion of larger particles determining the proportion of mechanical damage desired and the portion of smaller particles determining the proportion of thermal damage desired.

The practical upper limit on the size of chromophore particles used for infiltration into hair ducts to effect hair removal is the diameter of a hair duct, which is from about 70 μm to about 1 micron for human hairs. If a hair duct contains a hair, even smaller particles are generally used. Another practical consideration that affects the size of particles used in hair removal techniques is the prohibitively high cost of manufacturing uniformly sized particles in the submicron size range, such as uniformly sized carbon particles. Generally, for this reason, particles in this size range are obtained by grinding larger particles. The result is particles having a range of sizes, rather than uniformly sized particles. Even if the particles are uniform in diameter, due to their small size, they tend to clump together in aggregates. For example, the fullerene molecule ($C_{60}$) has the shape of a soccer ball with a calculated diameter of about 0.7 nm, but aggregates of $C_{60}$ reach 200 μm in size. Therefore, chromophore particles used in hair removal generally have a wide size distribution, generally in the range from about 0.01 μm to about 1 μm.

Carbon in the forms of graphite, carbon black, and fullerene is an excellent photon absorber and is available in particles having a wide range of sizes. Fullerene is available in particles or aggregates ranging in size from about 0.7 nm to 200 μm in size. Particles of carbon black range from about 10 nm to 500 nm in diameter, depending on the method of production. Graphite can be ground to form particles having a wide size distribution with an average size down to one micron. Particles can also be powder, or even pure carbon dust in one extreme. Any of these micro-particles of carbon can be loaded into hair follicles, whose diameter for human hairs is in the range from about 100 μm to 10 microns.

A contaminant with a bimodal size distribution is readily obtained by mixing together two groups of particles with different modal distributions, one relatively larger, and one relatively smaller.

In general, light absorbing chromophore particles of a relatively larger size will vaporize or explode when illuminated with at least one short pulse of light at sufficiently high power and a sufficiently short pulse duration. A consequence of vaporization is the shattering of the particle, with propulsion of the fragments into the depths of the hair follicle and into the surrounding cells. While vaporization of the contaminant particles is highly desirable for forcing the contaminant particles into the bottom of hair ducts, the most significant damage particles of this size can impart to tissue is cellular damage resulting from direct photomechanical disruption of the cellular membrane and other cellular structures. When the exploding particles are confined within a hair duct, the membranes of cells adjacent to the exploding chromophore are disrupted by the shock wave and by the exploded fragments of the particle bombarding the surrounding cells. The photomechanical effect of utilizing the larger size particles can be enhanced by using pulses in the nanosecond range of duration, for example about 1 to about 20 nanoseconds.

Other factors that influence whether a chromophore particle will explode or merely heat up when irradiated with short pulses of light of given pulse duration, frequency and fluence, are the physical properties of the particular chromophore used, such as its latent heat of vaporization and photon absorption coefficient. The photon absorption coefficient of graphite when irradiated with light having a wavelength of 1064 nm is estimated to be from about $1 \times 10^5$ cm$^{-1}$ to $2 \times 10^4$ cm$^{-1}$ (T. Barrett, *Absorption of Light by Small Spherical Particles in a Liquid*, ThermoTrex Corporation and T. Barrett, *Handbook of Carbon, Graphite, Diamond and Fullerenes*, Noyes Publications, Park Ridge, N.J., 1993). The corresponding depths to which the light will penetrate in a carbon particle before its energy has been absorbed, (i.e., the light penetration depth in carbon corresponding to the above range of photon absorption coefficients) is from about 0.1 μm to about 0.5 μm, respectively.

The present invention is illustrated with reference to particles of carbon, but other chromophore particles that absorb light and do not form toxic byproducts when pyrolyzed in hair ducts can also be used, and their use is specifically contemplated to be within the scope of this invention. One skilled in the art will appreciate that, if the heat of vaporization and absorption coefficient of a chromophore is known, thermodynamic principles can be used as illustrated herein to calculate what size range of particles will vaporize, and what size range will heat up and transfer heat to surrounding tissue without the loss of energy associated with vaporization of the particles.

The invention is more particularly described with reference to carbon particles as follows. In a hair follicle, carbon particles with an average diameter of approximately 1.0 micron will vaporize when illuminated via a Nd:YAG laser having a light beam with an energy density of about 2.5 J/cm$^2$, and a pulse duration of about 10 nanoseconds. These explosions translate mechanical energy to kinetic energy in the form of a shockwave, which causes both heat and motion. It has been discovered that the shockwave caused by exploding chromophore particles contributes substantially to the damage to the skin tissue that feeds growing hair follicles. Thus, an important aspect of the present invention is selection of chromophores having a particle size that will readily explode under the type of illumination provided, i.e., the energy density of individual pulses and the length of the pulse duration.

By contrast, relatively smaller particles of chromophore illuminated by pulses of light at the same power and pulse duration will tend not to explode, but will rapidly release the heat they absorb to a surrounding medium by thermal conduction. When the relatively smaller particles are confined within a hair duct, heat is rapidly conducted from the heated particles to the surrounding skin tissue, thereby causing thermal damage to such tissue. The thermal effects of illuminating the smaller particles may be increased by prolonging the pulse duration of the laser to the microsecond or millisecond range. For instance carbon particles with an average diameter in the range from about 1 to 50 nanometers will transfer absorbed heat to a surrounding medium such as skin tissue, substantially without explosion or vaporization when illuminated under the same conditions that explode 1 micron particles (i.e., a Nd:YAG laser with a fluence of about 2.5 J/cm$^2$ and a pulse duration of about 10 ns).

Figure 20C:
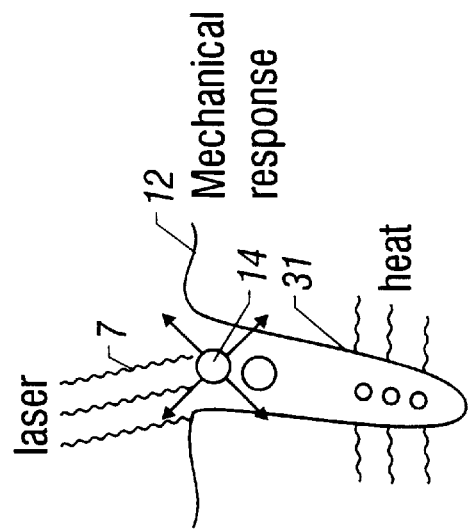
FIGS. 20A–C illustrate the hair removal method using large and small particles in the contaminant. →=photomechanical response; ⌇=photothermal response.
Figure 20B:
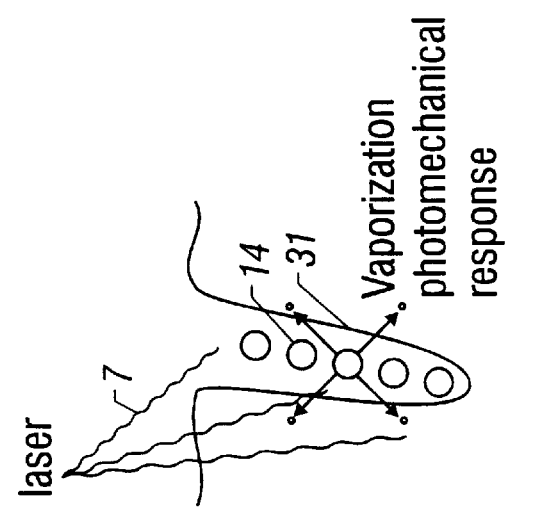
Figure 20A:
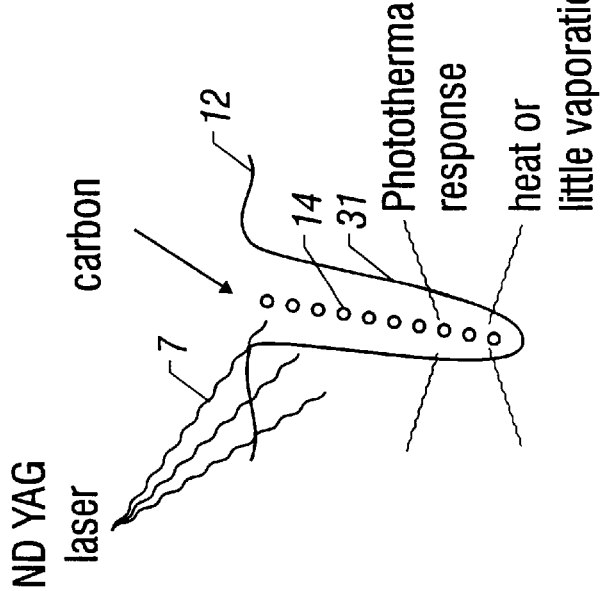
Figure 21A:
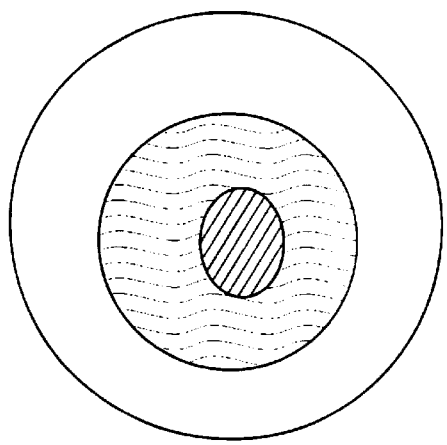
FIGS. 21A–E are drawings illustrating various types of microcarrier particles for delivering a sunlight-activated photochemical to hair ducts.
Figure 21C:
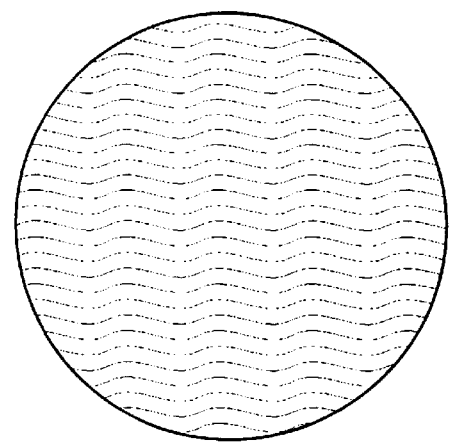
Figure 21B:
Figure 21D:
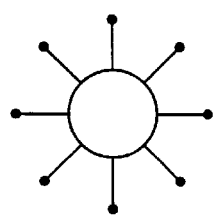
Figure 21E:
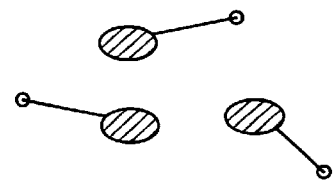

FIGS. 20A–C illustrate these concepts schematically. FIG. 20A schematically represents the transfer of photothermal energy to tissue surrounding a hair follicle 31 infiltrated with contaminant 14 containing carbon particles with diameters in the 1.0 to 50 nanometer range and illuminated by Nd:YAG laser light beam 7. FIG. 20B schematically represents the transfer of photomechanical energy to tissue surrounding a hair follicle 31 infiltrated with contaminant 14 containing carbon particles with diameters of about 1.0 micron and illuminated by Nd:YAG laser light beam 7. FIG. 20C schematically represents the combined transfer of photomechanical and photothermal energy to tissue surrounding a hair follicle 31 infiltrated with a combination of the contaminant carbon particles of FIGS. 20A and 20B.

Due to the extraordinary amount of energy that is consumed in transforming solid particles to a gaseous state, vaporization of particles consumes a large portion of the energy delivered to the particles. By comparison, heating the particles is very energy efficient. For example, about 7,686 J per gram will heat graphite from 0° C. to 3700° C., its vaporization temperature, but about 10 times as much energy is required to vaporize graphite, or about 65,000 J per gram. Therefore, much more powerful light pulses are needed to vaporize graphite and utilize photomechanical damage than is required for a purely thermal effect.

Vaporization of the chromophore particles is particularly useful for generating a force to propel the particles and their fragments deep into hair ducts and the walls of hair follicles. Once propelled into the vicinity of hair papillae, continued explosion of the particles by the pulses of light will produce shock waves and rapidly propel fragments so as to cause damage to hair growth cells responsible for the production of hair shafts. The damage inflicted on hair growth cells by these photomechanical effects may extend hundreds of microns into the walls of follicles.

In one embodiment of the laser hair removal method, vaporization of the carbon particles is required to generate a force propelling the particles and their fragments deep into hair ducts and the walls of hair follicles. Once located in the vicinity of the hair papilla and the structures responsible for production of the hair shaft (hair growth cells), the particles can be exploded again and again by the laser pulses to produce shock waves and rapidly moving fragments that will damage surrounding tissue. The damage to surrounding tissue by these photomechanical effects may extend hundreds of microns into the walls of the follicles. The acoustic shock waves being transmitted at the speed of sound will propagate substantially deeper and faster than the thermal damage at the short 10 ns pulse duration. Once shattered by explosion, large particles and aggregates will end up as a collection of much smaller fragments, which will absorb light energy and transfer heat into tissue without much mechanical damage.

In order to thermally devitalize cells in tissue surrounding a hair follicle, the tissue needs to be maintained at a high temperature for a period of time that varies with the temperature. The higher the temperature, the shorter the period required. For example, at 45° C., the required duration is about a couple of hours. However, it takes only about 0.1 second to damage skin cells at 70° C., and only about 1 millisecond at 80° C. The temperature to which a chromophore particle will be raised by any given pulse duration and laser fluence as well as the amount of heat it will deliver to surrounding tissue depends upon the thermodynamic properties of the chromophore, and the size of the chromophore particle irradiated.

The combination of mechanical and thermal energy transferred from the particles to the skin tissue sought to be destroyed is a very effective technique for achieving long term inhibition of the growth of hairs in hair ducts. Simultaneous photothermal and photomechanical damage to hair follicles is obtained by infiltrating into hair follicles a contaminant that contains a mixture of two particle sizes. For example, a contaminant containing a mixture of carbon particles having a diameter of about 1 nm to about 50 nm, for example about 10 nm, and carbon particles having a diameter of about 3000 nm to about 500 nm, for example about 1000 nm, can be used to induce simultaneous mechanical and thermal damage to skin tissue surrounding hair ducts.

The contaminant can further include a liquid, such as an oil, surfactant, or water-based lotion. In all mixtures and/or suspensions of chromophore particles in a suitable liquid, as well as solutions in which the carbon, or other chromophore, particles are dissolved in a solvent, the liquid acts as a heat sink for a vaporized particle, and causes the vaporized particle to condense back into the solid phase with the release of its heat of sublimation. For example, at a dilution of less than 1% by volume of 1 micron sized carbon particles in oil, the particles may shatter and vaporize to gaseous carbon, as well as emit smaller carbon particles. The oil is correspondingly heated, and transfers its heat to nearby cells. Therefore, an oil-containing contaminant with concentrations of carbon particles less than about 20% by volume (such as 2, 0.2 or even 0.02 volume %) increases the proportion of photothermal damage to the skin cells surrounding hair ducts, at the expense of photomechanical damage that would otherwise be caused by the particles alone. Also, rapidly moving solid carbon particles tend to be slowed down by the oil, thus lessening or preventing mechanical damage. Therefore, the proportion of mechanical to thermal damage caused in the hair follicles can also be controlled by varying the overall concentration or amount of the chromophore particles in the contaminant. For any given chromophore particle size and laser pulse width, there will be an optimum concentration of the light-absorbing chromophore in the mixture. Too much chromophore content (e.g., carbon particles) will act as a heat sink as well as block the passage of photons. Too little chromophore content will not absorb enough light, and will not heat up enough to effectively damage adjacent cells.

In the case of a contaminant having chromophore particles with a substantial range of sizes (as is obtained by grinding large particles to obtain smaller particles), the proportion of photomechanical to photothermal damage caused to the skin cells surrounding the hair ducts by the particles infiltrated therein can be controlled by controlling the size distribution of the particles and/or the average size of the particles. In general, decreasing the average size of the particles, decreases the proportion of photomechanical to photothermal damage, and increasing the average size of the particles increases the proportion of photomechanical to photothermal damage. Similarly, when the distribution of particles having a range of sizes is skewed towards the relatively larger particles, a larger proportion of mechanical damage will be obtained than when the distribution is skewed towards the relatively smaller particles.

In one embodiment of the invention, the particles infiltrated into hair ducts have a varied major dimension selected so that a combination of photomechanical and photothermal damage can be simultaneously administered to skin tissue adjacent to the hair duct, even when the pulse duration and the fluence of the pulses of light are held constant. It is generally desirable that no more than about 20 to about 5 percent of the energy delivered by the light source should be expended in vaporization of particles. Therefore, in one embodiment of the invention, wherein carbon is the chromophore, from about 10 to about 30 percent by weight of the particles have a major dimension in the size range from about 3000 nm to 500 nm, and the balance of the particles have a major dimension in the size range from about 500 nm to 100 nm. Similarly, by proper selection of the proportion of the particles that fall into the smaller and the larger size ranges, the proportion of photomechanical to photothermal damage caused upon illumination of the particles at any fixed fluence can be controlled.

The hair removal procedure may also be divided into two or more phases, including a first phase during which the contaminant is irradiated so as to explode the particles to drive them into the depths of the hair follicles, (i.e., the propulsion phase) and a second phase during which the contaminant is irradiated so as to raise the temperature of the tissue immediately surrounding the hair follicles to cause sufficient damage to inhibit future hair growth (i.e., the thermal phase). Such a procedure is described in co-pending U.S. Pat. application Ser. No. 08/644,231, filed May 13, 1996, which is incorporated herein in its entirety. For use in a multi-phase hair removal procedure of this type, during the first phase a majority of the carbon particles have an average diameter in the range from about 1 to about 60 nanometers, for example, about 10 nm, to maximize the proportion of photothermal damage effected. Then, during the second phase of the illumination, to maximize the proportion of photomechanical damage caused by illumination of the particles, the majority of the particles have an average diameter in the range from about 3000 nm to 500 nm, for example about 1000 nm. These size ranges are particularly preferred when the chromophore particles are carbon and the illumination is by pulses of light about 10 nanoseconds in duration with a wavelength of about 1.06 micron. One skilled in the art will be able to adjust the size ranges to correspond to alternative chromophores, wavelengths of light, and pulse length using thermodynamic calculations.

The present invention provides improvements in known methods of laser hair removal procedures. It allows the practitioner to control the thermal and/or mechanical damage administered to hair follicles either simultaneously or in sequential phases, by selection of the size of particles in a contaminant infiltrated into hair ducts. The practitioner is afforded increased control over the difficult task of forcing chromophore particles into the depths of hair ducts using laser light. The invention also affords the practitioner improved control over the amount of heat that is administered to the tissue in and surrounding the hair follicles during lasing. As a result of these improvements, the risk of unwanted damage to skin tissue is lessened, while the techniques of inhibiting hair growth are improved.

No. 7: A Method for Controlling Photomechanical Versus Photothermal Damage During Laser Hair Removal by Selecting Pulse Duration The use of a laser to induce hair follicle damage via irradiation of a carbon chromophore (e.g., carbon particles) has been previously described. The purpose of this invention is to employ modulation of and/or combinations of laser pulse durations to control administration of photomechanical and/or photothermal damage to the hair cells via an exogenous chromophore infiltrated into hair ducts.

The effect of particle size in controlling whether photomechanical or photothermal damage is administered to hair follicles by means of chromophore particles infiltrated therein is disclosed in Section No. 6 above. It is also possible to achieve a combination of mechanical and thermal damage to tissue surrounding hair ducts by using a relatively homogeneous size of particles, in conjunction with a combination of relatively long and short pulses of light. In general, short pulses of light tend to explode a chromophore particle, thus causing photomechanical damage. Pulses having a pulse width longer than the thermal relaxation time of a particle tend to heat up a particle without explosion so that heat is transferred to a surrounding medium. The surrounding medium is skin tissue surrounding a hair duct and/or a liquid medium in which the particle is dissolved or suspended. Thus, photothermal damage is caused to tissues adjacent to chromophore particles radiated by relatively long pulses of light. The combination of long and short pulses can be an alternating pattern of long and short pulses, a succession of short pulses followed by a succession of long pulses, or vice versa, or the long and short pulses can be administered simultaneously. In the latter case, it may be convenient to utilize two lasers simultaneously.

As used herein, the terms "long" and "short" are relative terms and must be defined with reference to the type and size of the chromophore particles illuminated. This principle is illustrated herein with reference to carbon particles and light pulses provided by a Nd:YAG laser with pulse frequency of about 10 Hz and fluence of about 2 to about 3 J/cm$^2$. Under these conditions, a "short" pulse duration (of a Nd:YAG laser) will be from about 10 ns to about 30 ns, while a "long" pulse duration will be from about 100 $\mu$s to about 100 ms. Preferably the carbon particles are suspended in an oil or water medium. Irradiation of the carbon with a "short" pulse will: a) break up aggregates of carbon particles, b) induce shattering of the larger (>50 nm) particles into smaller particles, c) drive particles deeper into the hair shaft due to the explosive force of the shattering of particles, and d) cause vaporization of the carbon to induce photomechanical tissue damage. A "long" pulse, on the other hand, will lead to heating of the smaller carbon particles, and the heat will be transferred (e.g., via an oil medium) to the surrounding tissue to induce photothermal damage, but will substantially avoid exploding or vaporizing the particles.

One option for producing both photothermal and photomechanical damage to the follicular tissue is to alternate short and long pulse durations when illuminating chromophore particles infiltrated into hair ducts. Alternating the pulse duration between short and long pulses will serve to break up any aggregates of carbon particles, and will cause both photomechanical and photothermal damage to tissue surrounding hair ducts into which the particles have been infiltrated.

The following examples model a zero-order estimation of the laser parameters suitable for administering any desired combination of photomechanical and photothermal thermal damage to hair follicles without burning skin, coagulating blood vessels in the dermal matrix, or destroying the skin pigment (i.e. melanin) located at the interface of epidermis and dermis.

EXAMPLE 4

Short vs. Long Pulse Lasers

The laser pulse energy and duration give rise respectively to the amount and rate of energy absorbed in light-absorbing chromophores respectively. For a given energy, the shorter the pulse duration, the higher the temperature rise in the light-absorbing medium. The absorbed energy is confined well inside the light absorbing chromophore at the end of a short duration pulse. Conversely, much of the heat may be dissipated into the surrounding medium if the pulse duration is very long. As a zero-order approximation, the energy dissipation distance in a given period of time can be written as:

$$x = \sqrt{\alpha \tau} \quad (1)$$

where x in cm is the energy dissipation distance; $\tau$ in seconds is the duration of energy dissipation; $\alpha$ in cm$^2$/sec is the thermal diffusivity, which is determined by the mathematic expression $\alpha = K/pc$ in which K is in J cm$^{-1}$s$^{-1}$ °C$^{-1}$, p is in g/cm$^3$, and c is in Jg$^{-1}$ °C$^{-1}$, represent the thermal conductivity, density, and thermal capacity, respectively. Table 4 lists the energy dissipation distances in graphite, mineral oil, and skin during a period of 10 ns (typical Q-switched Nd:YAG laser pulse duration), 100 μs (typical duration of non-Q-switched or free running Nd:YAG laser), and 100 ms (the duration between pulses of a 10 HZ laser). Table 4 shows that for a 1 μm graphite particle suspended in mineral oil or a 1 μm melanosome in skin, the absorbed energy is confined well inside the particle at the end of a 10 "short" ns pulse, but dissipates a significant distance from the particle during a "long" 100 μs pulse.

TABLE 4

The energy dissipation distance X (μm) in graphite, mineral oil, & skin during period τ

| τ | $X_{GRAPHITE}$ | $X_{OIL}$ | $X_{SKIN}$ |
|---|---|---|---|
| 10 ns | 0.16 | 0.03 | 0.03 |
| 100 μs | 16.3 | 2.82 | 3.23 |
| 100 ms | 515 | 89.1 | 102 |

Note:
the thermal diffusivities (cm$^2$s$^{-1}$) used in the calculation for graphite, mineral oil, and skin are 0.027, 7.94 × 10$^{-4}$, and 0.001, respectively Neglecting the energy loss due to dissipation, the instantaneous temperature rise in a light absorbing medium at the end of a 10 ns laser illumination can be expressed as $$\Delta T = \frac{\mu_a \phi}{\rho c} \quad (2)$$

where $\mu_a$ in cm$^{-1}$ is the absorption coefficient; and $\phi$ in J/cm$^2$ is the laser fluence. Because of the high absorption coefficient of graphite, its instantaneous temperature rise is over 1000° C. even at a 0.1 J/cm$^2$ laser fluence. The vaporization temperature of graphite (about 3700° C.) is reached at about 0.3 J/cm$^2$. For purposes of thermal coagulation of the hair follicle, vaporization of light absorbers should be avoided. It takes about 7,686 J per gram to heat graphite from 0° C. to 3700° C., but it needs about 9 to 10 times more energy to vaporize graphite (about 65,000J per gram). It is estimated that only about 5% of the energy needed to vaporize graphite is converted into kinetic energy of the vapor. Thus, about 95% of the laser energy cannot be used to raise the temperature of the tissue to be thermally damaged. Therefore, a Q-switched short pulse laser is not a good choice in terms of thermal damage of tissue. For graphite particles whose size is small enough so that the energy dissipation is significant even during a 10 ns pulse duration, vaporization of these particles can be prevented as was demonstrated for the situation of 1 nm and 10 nm graphite particles suspended in mineral oil. However, this scenario is hard to be implemented in practice because small particles tend to group together. For example, while a single $C_{60}$ fullerene is only about 1 nm in diameter, the aggregates of $C_{60}$ fullerene can be as large as 300 μm across. Furthermore, longer pulse duration is required in order to prevent burning of the skin, damaging blood vessels, destroying the skin pigmentation, i.e., the melanosomes.

For pulse durations longer than 100 μs, the energy deposited in a light absorbing chromophore can spread out significantly and thus reduce the peak temperature rise of the chromophore. As shown in Table 4, during a 100 μs period, the energy spreads out about 16 μm in graphite and about 3 μm in mineral oil. With respect to the photon penetration depth of about 0.1 μm in graphite at 1064 nm, the absorbed energy dissipates very far away from the source. For 1 μm graphite particles suspended in mineral oil, the temperature rise of the particle at the end of 100 μs illumination period with 1 J/cm$^2$ fluence is about 450° C. At the same fluence, the instantaneous temperature rise without energy dissipation would be over 10,000° C. if vaporization did not take place. A long pulse laser is clearly the choice to effect thermal damage of hair follicles. Even a 100 μs pulse is not long enough for some situations, as demonstrated below.

EXAMPLE 5

Thermal "Heating" of Hair Follicle with Long Pulse Laser

The temperature rise in the light absorbing chromophore and the surrounding medium can be obtained by solving the heat conduction equation:

$$K\nabla^2 T + S = \rho c \frac{\partial T}{\partial \tau} \quad (3)$$

where the first term is the energy flow rate into a unit volume due to a temperature gradient with K representing thermal conductivity; the second term represents the energy production rate per unit volume by heat source; and the term on the right side of the equation represents the energy associated with the temperature change per unit volume per unit time. With boundary and initial conditions given, the above equation can be solved to give the temporal and spatial distribution of temperature.

For the case of a hair follicle filled with light absorbing chromophores, analytical expressions of the temperature inside the hair follicle and in the surrounding tissue can be obtained with the following approximations (H. S. Carslaw et al, *Conduction of Heat in Solids,* Oxford University Press, N.Y., 1995, p 347):

The hair follicle is considered as an infinitely long cylinder.

The light absorbing medium inside the follicle and the surrounding tissue are different uniform substances, but with the same initial temperature $T_0$.

There is a constant heat production S per unit time per unit volume at t>0 inside the cylinder.

The temperature rise during heating and thermal relaxation after heating are related by:

$$\Delta T(r, t) = \begin{cases} \Delta T1(r, t) & 0 \le t < \tau_p \\ \Delta T1(r, t) - \Delta T1(r, t - \tau_p) & t \ge \tau_p \end{cases} \quad (4)$$

where ΔT1(r, t) and ΔT(r, t) represent the temperature change during and after the heating phase, respectively; $\tau_p$ is the duration of heating; and r and t denote the radial coordinate and time, respectively. The thermal conductivities and diffusivities of the two media inside and outside the cylinder need to be known in order to calculate the temperature change for hair follicles filled with a topically applied contaminant comprising micron size graphite particles suspended in mineral oil with a mass ratio of 20%. These quantities in the contaminant are determined by the properties of graphite, mineral oil, and their volumetric ratio, using known procedures.

For heating of a graphite suspension in mineral oil with laser pulse longer than 100 μs, it is possible to heat up the lotion fairly uniformly because of the energy dissipation from graphite particles to mineral oil. Assuming a constant laser fluence reaching a hair follicle and absorption in the follicles of all the photons striking it, the heat production per unit volume per unit time is determined by formula 1.5 as follows:

$$S = 2\frac{\phi}{a\tau_p} \quad (5)$$

where S (Jcm$^{-3}$ $^{s-1}$) is the heat production per unit volume per unit time; φ(J/cm$^2$) is the laser fluence striking the hair follicle; a (cm) represents the radius of the hair follicle; and τ$_p$ (sec) denotes the pulse duration.

With the treatments discussed above, the temperature distribution T(r,t) for the case of a hair follicle filled with graphite/oil contaminant are calculated for different laser fluences and pulse durations. Immediately after the laser pulse, the energy is localized well inside the hair follicle, but the temperature of the lotion is well below the vaporization temperature of graphite (about 3700° C.). By 10 ms after irradiation, the hair follicle is appreciably thermally relaxed. To demonstrate the pulse duration effect, the laser fluence is kept at 3 J/cm$^2$, but the pulse duration is stretched from 100 μs to 10 ms. For pulse durations from 100 μs to 10 ms, the temperature rise of the tissue between the wall of a follicle and a distance one follicle radius away from the wall is over 50° C. for a period of a few milliseconds. The corresponding absolute temperature is over 80° C. after adding on the base body temperature (about 37° C.).

Tissue is damaged if kept at 80° C. for a period of about 1 ms. Thus, the tissue as far as one hair follicle radius away from the hair duct wall is thermally damaged, with transfer of sufficient heat to prevent hair growth from the follicle for a long period. When the same amount of energy is delivered in a pulse of 100 ms, the temperature rise of the tissue one follicle radius away from the follicle wall is not enough to thermally damage the tissue. However when the fluence is raised from 3 J/cm$^2$ to 6 J/cm$^2$ for the 100 ms pulse, the temperature rise in the tissue between the wall of a follicle and one follicle radius away from the wall is over 30° C. for a period of about 0.1. The corresponding absolute temperature distribution is about 70° C. for a period of about 0.1 second, which is high enough to cause thermal damage of the tissue. By these studies it is discovered that when the pulse duration gets longer, the absorbed energy is more uniformly distributed over the tissue. By the time a pulse duration as long as 1 sec is reached, selective thermal damage of the tissue immediately surrounding a hair follicle is almost impossible. Thus, from the point of view of selectively damaging the tissue near a hair follicle, a shorter pulse is preferred. However, as a general rule, the shorter the pulse duration, the greater the danger of causing undesirable destruction of skin.

The invention thus provides improvements in known methods of laser hair removal procedures. It allows the practitioner to control the thermal and/or mechanical damage administered to hair follicles either simultaneously or in sequential phases, by selection of the size of particles in a contaminant infiltrated into hair ducts. The invention provides to the practitioner increased control over the difficult task of forcing chromophore particles into the depths of hair ducts using laser light. The invention also affords the practitioner improved control over the amount of heat that is administered to the tissue in and surrounding the hair follicles during lasing. As a result of these improvements, the risk of unwanted damage to skin tissue is lessened, while the techniques of inhibiting hair growth are improved.

No. 8: A Method for Sunlight-Assisted Hair Removal

Methods of hair removal are known in which a photochemical is infiltrated into hair ducts and then exposed to light having a wavelength absorbed by the contaminant. Upon illumination, the photochemical produces a chemical species that destroys skin tissue in and around the infiltrated hair ducts. For example, Japanese patent No. 63-249577 discloses methods of hair removal that utilize porphyrin and chlorin derivatives, which release singlet oxygen upon irradiation by a frequency-matched light. However, known methods are time consuming and are generally administered in a salon or clinic, making them expensive.

The present invention overcomes some of the difficulties of the art by utilizing sunlight as the light source in a method for long term inhibition of hair growth. This method of inhibiting hair growth can be practiced without any specialized equipment or skills. In this invention, the photochemical is a prodrug that is activated by sunlight to create a chemical species toxic to cells in and surrounding hair ducts that cause hair growth, but is safe for topical application to the surface of skin. Non-limiting examples of sunlight-activated prodrugs that can be used in the practice of this invention are photophrine II, amino levulenic acid, beta carotene and tetracycline.

The sunlight-activated photochemicals are administered at a relatively high dosage, for example about 2% by weight of a aqueous solution. However, it should be noted that a substantially more dilute concentration (for example, one ten times less concentrated that what is used to cause hair removal) will not cause hair removal, but will cause a slight inflammation in the hair follicles sufficient to stimulate hair growth.

In the method of the invention, the sunlight-activated photochemical is applied to the skin surface in an area in which it is desired to inhibit hair growth. Gentle massage is used to infiltrate a portion of the photochemical into hair ducts in the section of skin treated. Due to the extremely high metabolic rate of hair growth cells, the sunlight activated prodrug is preferentially and rapidly absorbed within hair ducts and into cells and adjacent tissue structures that generate hair growth. Such cells include hair papilla cells, stem cells, keratinocytes, and endothelial blood vessels. Absorption of the photochemical into other, more slowly growing cells, is at a substantially slower rate. In addition, the stratum corneum layer in skin acts as a protective barrier to prevent significant absorption of the photochemical through the skin surface.

A period of time must be allowed for the photochemical to be absorbed by and concentrated in the target hair growth cells. Generally, a period of about 1 to about 7 hours is sufficient time to allow normal biological processes to assist in absorption of the photochemical in the fast-growing target cells. The rest period for any particular photochemical can be determined empirically by one skilled in the art. After this rest period, the contaminated skin section is exposed to direct sunlight for a period of time sufficient to activate the prodrug, thereby causing damage to the hair growth cells. Generally, the time of exposure will be from about three to about four hours, but may in some cases be as little as 20 minutes.

Therefore, in one embodiment of the invention, the sunlight-activated photochemical is applied to the skin surface before retiring to bed, and the next morning the area of skin so treated is exposed to direct sunlight by taking a sun bath or going to the beach for a period of several hours. By timing the illumination in this manner, the hair-producing cells in the follicle, as well as the tissue immediately surrounding the follicle that feed the hair, are damaged by photochemical activation of the prodrug photosensitizer, but without substantial damage to other tissue.

Figure 22:
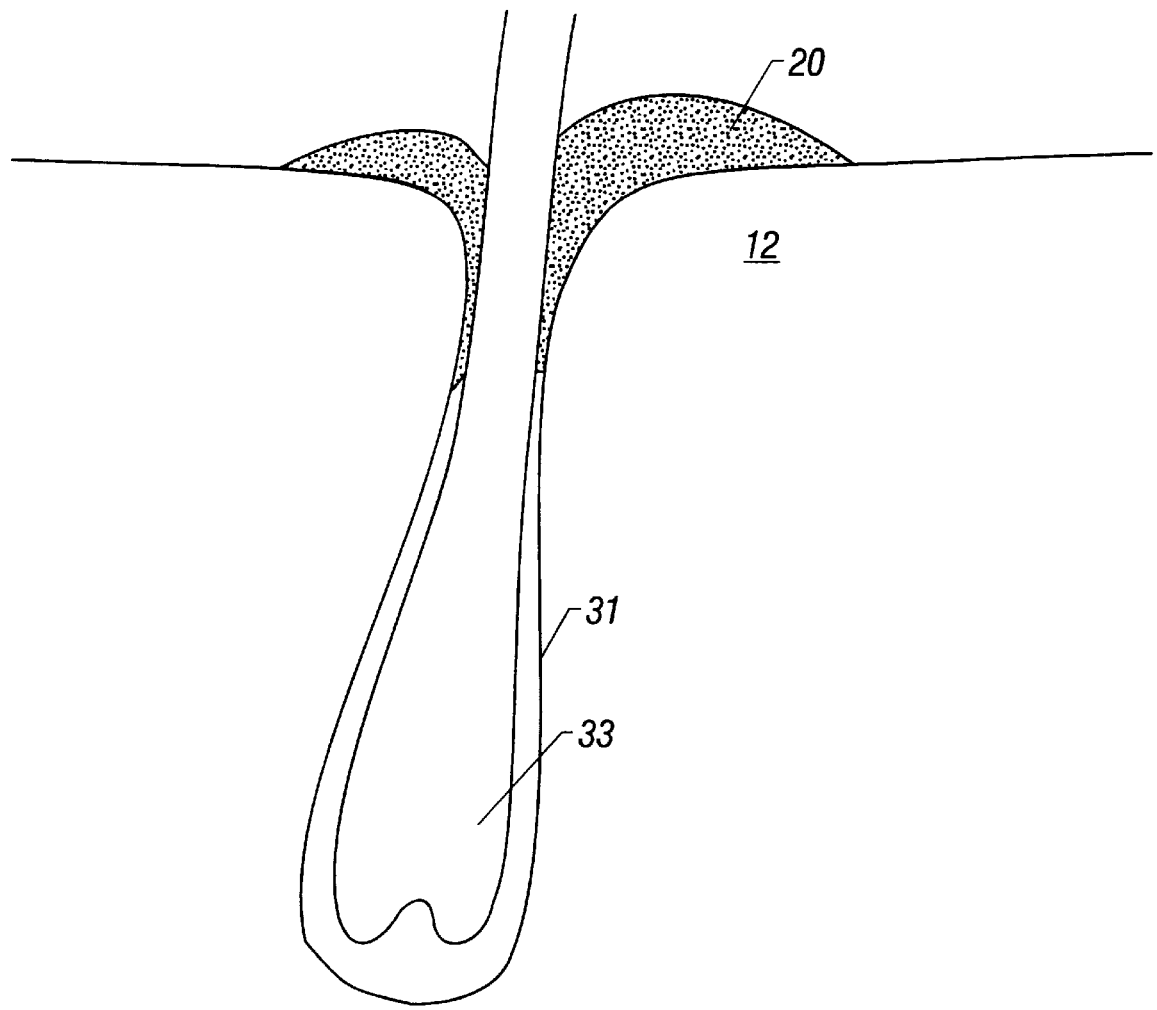
FIG. 22 is a schematic drawing showing penetration into hair ducts of microcarriers having a photochemical associated therewith.
Figure 23:
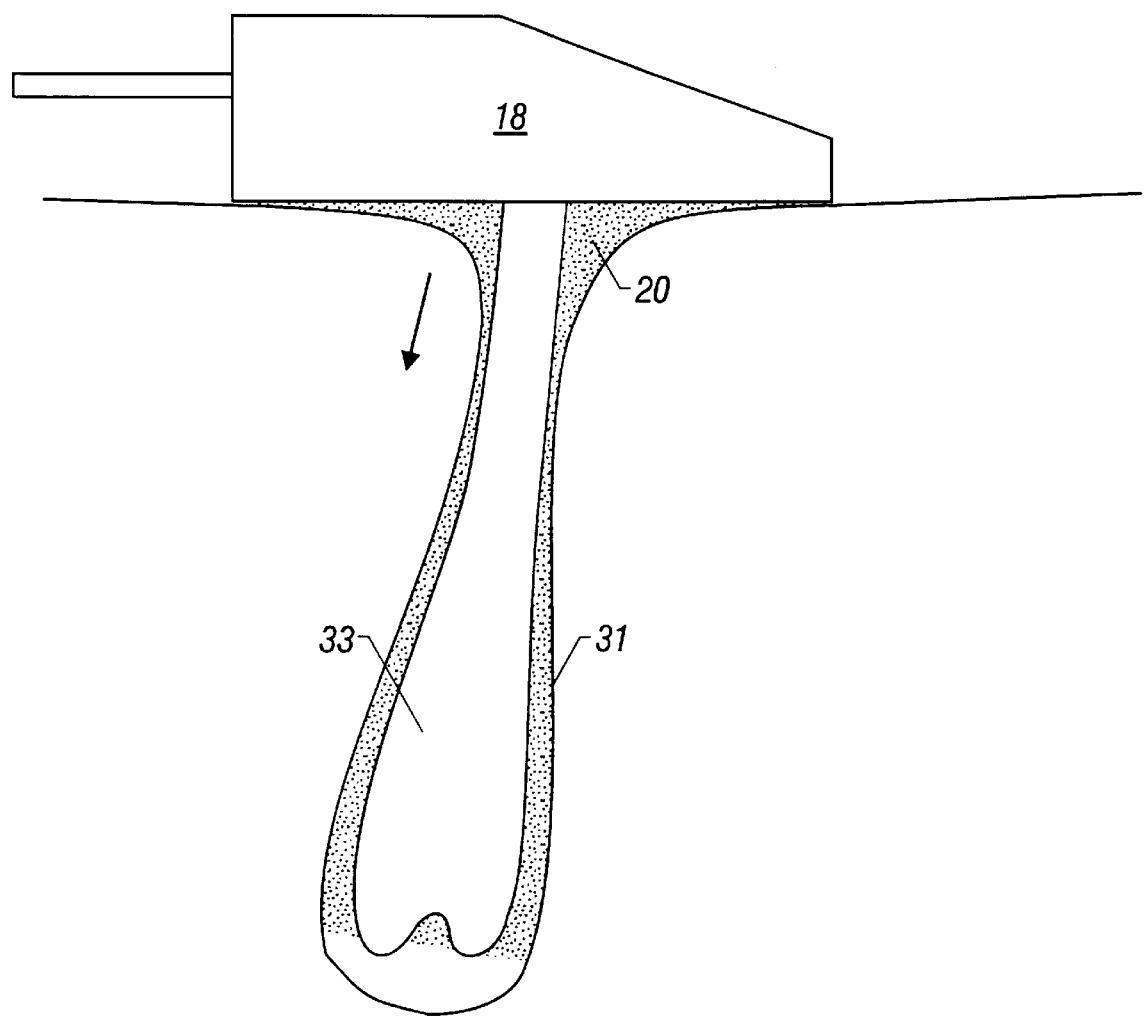
FIG. 23 is a schematic drawing showing use of ultrasound vibration to enhance penetration of the microcarriers into hair ducts.

In another embodiment of the invention, the photochemical is entrapped or encapsulated within microcarrier particles in a formulation suitable for topical administration, such as a formulation of liposomes or coacervate microcapsules. FIGS. 21A–E show different types of microcarriers containing a photochemical. As shown in FIG. 22, the microcarrier particles 20 containing the photochemical are applied topically to the skin surface 12 and induced to penetrate into a hair duct 31 in the spaces around hair shaft 33, for example by gentle massage of the skin surface. An ultrasound vibrator 18 may be applied to the skin surface 12 to force the microcarrier particles 20 into the hair duct 31 as shown in FIG. 23.

The lining of hair ducts does not have an epithelial barrier layer, such as the stratum corneum. Consequently, the lipids in lipid-based particles, such as liposomes, enhance penetration of the prodrug across the cell walls of papilla cells, stem cells, and keratinocytes in the infiltrated hair ducts. Then, irradiation of the skin surface with sunlight as described above activates the photochemical prodrug so as to damage these hair growth cells.

To accommodate this function, the microcarrier particles are sized large enough to avoid absorption across the stratum corneum at the skin surface, but small enough for entry and passage into the hair duct. For application to humans, the diameter of the microcarrier particles is generally less than about 70 $\mu$m, for example about 10 $\mu$m to about 50 $\mu$m because the diameter of hair ducts in humans is in the size range from about 70 $\mu$m to about 1 micron.

Methods are well known for encapsulating an active agent within a microcarrier particle, such as a liposome or a microcapsule. For example, there are at least three types of liposomes. Multivesicular liposomes (MVL) are man-made, microscopic lipid vesicles comprising lipid membranes enclosing multiple non-concentric aqueous chambers. Multilamellar liposomes or vesicles (MLV) have multiple "onion-skin" concentric membranes, in between which are shell-like concentric aqueous compartments. Multilamellar liposomes and multivesicular liposomes characteristically have length-weighted mean diameters in the micrometer range, usually from 0.5 to 25 $\mu$m. Unilamellar liposomes or vesicles (ULV) are liposomal structures having a single aqueous chamber, usually with a mean diameter range from about 20 to 500 nm.

Multilamellar and unilamellar liposomes can be made by several relatively simple methods. The prior art describes a number of techniques for producing ULV and MLV (for example U.S. Pat. Nos. 4,522,803 to Lenk; 4,310,506 to Baldeschweiler; 4,235,871 to Papahadjopoulos; 4,224,179 to Schneider; 4,078,052 to Papahadjopoulos; 4,394,372 to Taylor; 4,308,166 to Marchetti; 4,485,054 to Mezei; and 4,508,703 to Redziniak). Methods for making multivesicular liposomes are disclosed in Kim et al., *Biochem. Biophys. Acta*, 728:339–348, 1983). For a comprehensive review of various methods of ULV and MLV preparation, refer to Szoka, et al. *Ann. Rev. Biophys. Bioeng.* 9:465–508, 1980.

Also contemplated within the scope of this invention is a composition for topical application to a skin surface for inhibiting hair growth on the skin surface. The composition comprises a sunlight-activated prodrug encapsulated in a microcarrier particle, such as a liposome or microsphere. The diameter of the particles is generally less than 70 $\mu$m, for example about 10 $\mu$m to about 50 $\mu$m. In one embodiment, the sunlight activated prodrug is selected from the group consisting of photophrine II, amino levulenic acid, and tetracycline. The composition further comprises a physiologically acceptable carrier suitable for topical application. The carrier may comprise any conventional topical formulation base, such as those described in Remington's "Pharmaceutical Sciences," 17th Edition (Mack Publishing Co., Pa.), the disclosure of which is incorporated by reference. A lotion, suspension in oil, solution, cream, ointment, gel, aerosol, or nebulized formulation are representative of the topical compositions of this invention.

This method for inhibiting the growth of unwanted hair provides the advantage of home treatment because the light source used to activate the photochemical prodrug is sunlight. A topical composition containing the sunlight-activated prodrug can be self-administered, and, after a rest period to allow accumulation of the prodrug in hair-growth cells lining hair ducts, a simple sun bath is all that is required to activate the prodrug and thereby inflict sufficient damage to inhibit hair growth on a long term basis.

No. 9: A Method for Inhibiting Hair Growth Using Anti-Proliferative Agents

It is known to infiltrate photoactivated chemical compounds, such as porphyrin and chlorin derivatives, into hair ducts, and then to illuminate them with light at a wavelength that causes the photochemicals to release species harmful to cells in hair follicles responsible for hair growth. However, the light sources used for illumination, such as lasers, are expensive and usually require trained operators to avoid unwanted damage to skin and eyes.

The present invention provides a method for temporarily inhibiting growth of unwanted hair on a section of skin by topically applying an anti-proliferative agent to the section of skin to be treated. The anti-proliferative agents do not require activation by any type of light source. Normal hair growth will recommence once the treatment is withdrawn.

During application of the anti-proliferative agent, care is taken to assure that at least a portion of the anti-proliferative agent is delivered into hair ducts on the section of skin to be treated to inhibit hair growth. Preferably the anti-proliferative agent is delivered along the full length of the hair duct, which length varies depending upon the bodily location of the skin section to be treated (i.e., on the face, legs, or arms). The depth of the hair duct also varies for an individual hair depending upon the phase of the hair growth cycle in which it is found. During the mature anagen phase, for example anagen V and VI, the hair follicle is fully extended (to a depth of 3.0 to about 5.0 mm), and the distance to the bottom of the follicle from the skin surface is about twice that during the telogen phase of the hair growth cycle. Therefore it is advantageous to synchronize the growth cycle of the hairs to be treated before application of the anti-proliferative agent to the area to be treated for inhibition of hair growth. Methods for synchronizing the hair growth cycle are disclosed above in Section No. 1 herein.

The anti-proliferative agent is applied to the skin surface in any suitable topical formulation, such as a lotion, cream or gel. Suitable formulations preferably are designed to aid in delivery of the anti-proliferative agent into hair ducts, and may therefore, include one or more chemical agents that will reduce surface tension, such as a surfactant.

Anti-proliferative agents useful in the practice of this invention include small molecules as well as macromolecules, such as proteins or enzymes, that interfere with or interrupt in any way the cycle of cell proliferation. Representative examples of anti-proliferative agents useful in the compositions and methods of the present invention include methotrexate, doxorubicin, taxol, tumor necrosis factor, chlorambucil, interleukins, etoposide, cytarabine, fluorouracil, vinblastine. The mechanism of action of the anti-proliferative agent is immaterial other than that it interferes with or interrupts the cycle of cell proliferation. For example, methotrexate, aminopterin and cytosine arabinoside (also known as cytarabine and Ara-C) are cell cycle-specific antimetabolites that kill cells only when they are synthesizing DNA. Fluorouracil inhibits formation of both DNA and RNA. Methioninease is an enzyme that inhibits uptake of methionine by hair papilla cells proliferating at a high rate.

Hair ducts are not lined by an epithelial barrier layer, such as the stratum corneum, but do contain rapidly proliferating hair papilla cells, stem cells, keratinocytes, and endothelial blood vessels, which generate hair growth. These cells in the hair duct responsible for hair growth are the fastest growing cells in the body, aside from tumor cells. Due to the absence of a barrier layer in the hair duct, the anti-proliferative agents are preferentially take up by these hair growth cells, which have a high metabolic rate. Entry of the anti-proliferative agents into other, more slowly growing cells, is at a substantially slower rate. Consequently, the anti-proliferative agents are preferentially absorbed into the target hair growth cells, with the result that hair growth is inhibited.

Application of the anti-proliferative agent to the skin surface is repeated at spaced intervals of hours or days until hair growth is inhibited. Generally, the anti-proliferative agent is applied two times daily for so long as it is desired to inhibit the growth of hairs from the treated portion of the skin. Once treatment is stopped, hairs in the treated section of skin will commence a normal growth pattern.

In one embodiment, the anti-proliferative agents are encapsulated in lipid-based particles, such as liposomes or microcapsules, for application to the skin surface. The lipid-based particles are sized small enough to enter into hair ducts in the section of skin, but large enough not to be absorbed across the stratum corneum. Care is taken during application of the lipid-based particles to assure that at least a portion of the drug-bearing particles enters into the hair ducts. For example, the micro particles can be formulated in a physiologically acceptable carrier containing one or more chemical agents that will aid entry of the particles into hair ducts. It is believed that administration of the anti-proliferative agents encapsulated in lipid-based particles will increase uptake of the anti-proliferative agent. As the lipid-based particles begin to break down in the hair duct, both the encapsulated drug and lipids from the bilayers of the lipid-based particles are released. These lipid byproducts can aid in delivery of the released drug across the cell membranes of the target cells. Methods for obtaining an active agent encapsulated in lipid particles, such as liposomes and microcapsules are well known in the art and are referred to above in Section No. 8 herein.

Lipid-based particles, such as liposomes, deliver the encapsulated agent slowly within the hair duct, so that the cells lining the hair duct are bathed in the anti-proliferative agent over an extended period of time, generally over a period of hours or even days. Slow release of the anti-proliferative agent from the lipid-based particles is particularly advantageous for those agents that interfere with a particular step in the proliferation cycle of the cells, such as formation of DNA and/or RNA, because not all cells enter mitosis at the same time.

The dose of the anti-proliferative agent administered, whether encapsulated or unencapsulated, can vary from about a few picomoles to about several hundred millimoles. The desirable dose of anti-proliferative agent per unit area of skin treated is a hair growth-inhibiting amount, and will vary depending upon such characteristics as the stage of target hairs in the hair growth cycle at the time of administration, the age and condition of the subject, the particular properties of the agent, and the dosage schedule. In general, the dosage range of the anti-proliferative agent appropriate for topical application to humans is in the range of about 0.001 to about 6,000 mg/m$^2$ of body surface area, generally applied in a cream, ointment or solution containing about 10% of the anti-proliferative agent by weight. While doses outside the foregoing dose range may be given, this range encompasses the breadth of use for most anti-proliferative agents useful for inhibiting hair growth. The dose range for a particular anti-proliferative agent can be easily ascertained as previously described.

The present invention provides the advantage over other hair removal procedures that no specialized equipment is required to inhibit growth of unwanted hair. No lasers, razors, depilatory needles, etc., are required for safe and temporary inhibition of hair growth. The anti-proliferative agent is repeatedly applied onto the surface of skin so as to cause the anti-proliferative agent to enter hair ducts therein, and hair growth will recommence upon cessation of the treatment. The embodiment of the invention in which the anti-proliferative agent is administered in a slow release lipid-based formulation provides convenience by reducing the number of times the formulation must be used to accomplish the goal of inhibiting hair growth.

No. 10: Use of Methionine to Stimulate Hair Growth or Regrowth

Among many people, there is great interest in stimulating the growth or regrowth of human hair. For example, alopecia, especially male pattern baldness, is a condition that is common to a large proportion of the male population. The present invention provides a method for stimulating hair growth or regrowth to reduce the symptoms of hair loss.

It is known that the amino acid methionine is required by the body for rapid cell proliferation, such as in the growth of tumors. The inventors herein have discovered that application of methionine to a skin section so that it penetrates into the hair ducts to contact hair growth cells therein can be used to induce growth of hairs from follicles therein. (The anagen stages of the hair growth cycle are characterized by rapid proliferation of hair growth cells). In some cases, even if growth of hairs from the target follicles has ceased for a considerable period of time, the administration of methionine into the hair ducts, so as to contact the hair growth cells, i.e., the hair stem cells, will restore hair growth. In other cases, vellum hairs have been restored to normal pigmented hair growth by the application of methionine to the hair growth cells in hair ducts.

Methionine is administered to hair growth cells in a hair follicle in a hair growth stimulating amount, which may differ depending upon the phase in the hair growth cycle, the anatomical location of the hairs, such factors as the age and general health of the patient, and the dosage schedule. Taking these factors into account, one of skill in the art will be able to determine the appropriate timing and amount of doses appropriate for any individual in need of treatment. In general, however, it is recommended that a dose of about 0.001 to about 6,000 mg per square meter of skin surface to be treated should be rubbed into the skin section twice a day, for instance morning and night. As methionine is non-toxic to all mammals, there is no known overdose effect.

The treatment should be continued until satisfactory hair growth has been restored. In some individuals restored or enhanced hair growth is noticed in as little as about 3 to about 5 weeks, while in others a noticeable difference in hair growth or regrowth is not noticed until the treatment has been continued for a period of several months, for example, 5 months.

To enhance penetration of methionine into hair ducts and enhance uptake of the amino acid by hair growth cells therein, the methionine can be administered in a liposome or other lipid-based microparticle. The properties of liposomes and methods for encapsulating a biologically active agent, such as methionine, into liposomes are described in Section No. 8 herein. The methionine can also be contained in a formulation suitable for topical administration, such as an ointment, cream, suspension or solution.

The present method of stimulating hair growth by contacting hair growth cells with sufficient methionine to stimulate hair growth cells in hair ducts has an advantage over prior art hair stimulation compounds and methods of their use in that methionine is not toxic to mammals. In addition, as it is an amino acid, Methionine is inexpensive to use in comparison with prior art hair growth stimulating drugs, such as Minoxidil.

No. 11: A Method for Treating Herpes with Laser

Seroepidemiologic studies have shown that infections of Herpes viruses are found worldwide. Infections of Herpes Simplex (oral or genital) or Herpes Zoster virus can manifest as skin lesions and/or rash at almost any location on the body. After a primary infection subsides, Herpes virus is reported to reside within the skin at the bulge area of the hair duct during latent phases of the disease. For this reason, mild trauma to the skin, or any treatment of the skin with a topical medication or lotion, may be followed by reactivation of the disease. It is known to treat such manifestations with an anti-viral agent that interferes with the replication of viral DNA, for example, oral administration of acylovir or a topical 5% acylovir ointment or cream.

The present invention provides an alternative method for preventing Herpes outbreaks on the skin of susceptible individuals and/or treating infections of Herpes viruses on skin. During latency, Herpes viruses reside in the bulge area of the hair follicles. FIG. 1 shows a cross-section of a hair duct with a hair shaft 33, sebaceous gland 38, and bulge area 40. The hair growing in the hair duct shown in FIG. 1 is in the anagen phase of the hair cycle, so that the follicle is extended to its full length, and the bulge area 40 of the hair duct is located about one-half way down the follicle, just below the sebaceous gland.

In this invention, reactivation of a Herpes virus infection in the form of skin lesions is prevented or treated. To prevent reactivation, hair ducts in the infected skin section are infiltrated with a light-absorbing contaminant so that at least a portion of the contaminant enters the bulge area of hair ducts containing latent Herpes viruses. Then the contaminated skin section is illuminated with short pulses of light at a wavelength more highly absorbed by the contaminant than by skin. Light energy absorbed in the form of heat or kinetic energy by the infiltrated contaminant in and around the bulge area is transferred to the latent viruses residing in the hair ducts. As a result, the Herpes viruses are denatured or destroyed, rather than suppressed in replication. By taking these steps, an outbreak of a Herpes skin infection is prevented.

A Herpes skin infection can also be treated during an episode of reactivation using the method of this invention. During a reactivation of a Herpes skin infection, latent viral particles in hair ducts become active and multiply, with transmission of viral particles up through the hair duct to the skin surface. By practice of this invention during an episode of reactivation, viral particles throughout the hair duct are heated and destroyed.

The methods of this invention are variations of laser hair removal techniques. It has now been discovered that these methods can be used to destroy or eradicate Herpes viruses sequestered within hair ducts in an infected skin section, whether or not the hair ducts contain viable hairs. U.S. Pat. Nos. 5,226,907 and 5,425,728 to Tankovich, which are incorporated herein in their entireties, disclose methods for hair removal and/or long term inhibition of hair growth utilizing a light absorbing contaminant that is infiltrated into hair ducts and then illuminated with short pulses of light. The contaminant is generally a water or oil-based suspension or solution containing chromophore particles having a good absorption at or near at least one frequency band of light, but any type of contaminant that absorbs light energy can be used. If the contaminant contains chromophore particles, for example carbon or graphite particles, they are generally sized too large to penetrate the barrier layer of the stratum corneum, but small enough to readily infiltrate the treated hair follicles. These techniques are modified in the present invention in that hair ducts containing latent viruses are infiltrated with the contaminant so that at least a portion of the contaminant enters the bulge area of the hair ducts adjacent to the latent viruses. Then the contaminated hair ducts are illuminated with short pulses of a light beam containing at least one wavelength that is well absorbed by the contaminant, but which penetrates skin with a minimum of absorption and scattering therein, such as that produced by a Nd:YAG laser. The short pulses of light can be used to cause explosions in the particles so as to drive the contaminant deep into the bulge area of hair follicles. The short pulses of light also cause heating of the contaminant.

Heat generated in irradiated contaminant in and around the bulge area of hair ducts is transferred to viral particles either by conduction or by transfer of kinetic energy from explosion of particles in the contaminant. The short pulses of light may also destroy viral particles on a skin surface if the viral particles absorb the frequency of light used during the illumination, or if there is sufficient contaminant on the skin surface to absorb heat from the pulses of light. Generally, to destroy viruses in hair ducts, i.e., in the bulge area, the viral particles contained therein should be raised to a temperature of about 70° C. to about 80° C. for about 0.1 to 1.0 second. The size and material of the light absorbing chromophore particles in the contaminant should be matched to the properties of the light source so as to deliver sufficient heat to the bulge area of the infected skin section to provide the necessary heat to destroy the viral particles without substantial damage to the skin section treated. In general, the particles are sized large enough to avoid penetration of the particles through the stratum corneum, but small enough to enter into the opening of hair ducts. As the diameter of hair ducts in humans is generally in the range from about 70 $\mu$m to about 1 micron in size, the particles are generally in the range from about 0.01 micron to about 1 micron.

To avoid overheating of surface skin tissue, the light source should be absorbed by the contaminant, but should penetrate skin with a minimum of absorption and scattering therein. If a laser is the light source, any of the lasers useful in treatments to inhibit hair growth by infiltrating a contaminant into hair ducts can also be used in the practice of this invention. In one embodiment, the contaminant contains carbon particles, and the light source is a Nd:YAG laser providing short pulses of light having the following properties:

Wavelength about 1064 nm

Beam Shape: circle or square

Beam Size: about 8 mm (circular) of 7×7 mm (square)

Fluence 1–2 J/cm$^2$

Pulse energy 0.5 J/pulse

The clinical manifestations and course of a Herpes episode depend on the anatomic site of the infection, the age and immune status of the host, and the antigenic type of the virus, i.e., whether HSV-1 or HSV-2. The spread of virus to the skin from peripheral sensory nerves helps explain the large surface area that may be affected, and the high frequency of new lesions distant from the initial crop of vesicles.

Individuals who are particularly susceptible to Herpes infections in skin are those who are immunocompromised and those who manifest other types of skin conditions indicative of immunocompromise. For example, individuals with psoriasis, Darier's disease, eczema herpeticum, or atopic eczema are thought to be susceptible to cutaneous HSV infections due to reduced numbers of circulating NK cells and a decrease in IL-2 receptors in the diseased tissue (H. M. Goodyear, Br. J Dermatol 134: 85–93, 1996). In such individuals, the method of this invention is particularly useful either prophylactically to prevent reactivation of the virus in skin lesions, or as a treatment of an existing viral activation or reactivation.

The mechanisms by which various stimuli cause reactivation of HSV infection are not known. Ultraviolet light, immunosuppression, and trauma to the skin or ganglia are associated with reactivation. Some hair removal techniques that cause trauma to the skin, such as waxing, use of contaminants in hair ducts, or use of chemical depilatories, may trigger an outbreak of Herpes in the skin section involved. The method of this invention is also effective for treating skin to prevent such outbreaks or eradicate Herpes virus throughout hair ducts when a manifestation of a viral infection has been triggered by hair removal techniques that cause trauma to the skin, even if the hair ducts involved no longer contain hairs.

By the methods of this invention, Herpes outbreaks on skin can either be prevented or treated without reliance upon systemic administration or topical application of an antiviral agent. Thus, patients with low tolerance for such agents, or who choose to avoid exposure to drugs, can be treated using a relatively inert contaminant, e.g., carbon particles and light.

No. 12: A Method for Reduction of Sweat and Body Odor

Human bodies produce sweat to reduce overheating and in response to emotional stimulae. Sweat is produced by glands (sudorific or sweat glands) situated at a depth of about 1 to 2 mm below the surface of the skin on almost all of the body surface. Bacterial action causes decay of proteinaceous compounds in sweat, creating undesirable body odors. Prior art methods for reducing production of sweat and/or treating body odor include various creams, gels and powders that block production of sweat or combat growth of bacteria.

Laser treatment can be used to reduce human odor and/or the production of sweat. In this invention, known laser hair removal methods are modified for use in inhibiting production of sweat from sweat glands.

Sweat glands are distributed widely over the surface of the skin and are found in almost all locations of the body. In the present invention, a section of skin containing sweat glands is infiltrated with a contaminant, for example one containing carbon particles. The particles are infiltrated into spaces in or adjacent to sweat glands via hair ducts. Then the skin surface is illuminated with short pulses of laser light that is preferentially absorbed in the particles, but is minimally absorbed in skin. As the blood vessels that supply blood to sweat glands are located at a depth of about 1 to about 2 mm below the surface of the skin, during illumination of the skin surface with the short pulses of light, a lens with a short focal length is used to focus the light at a depth of about 1 to about 2 mm below the skin surface to destroy the sweat glands. In one embodiment, a light with a wavelength in the range from about 532 nm to about 600 nm is used to destroy blood vessels supplying blood to sweat glands. Once the skin surface has been illuminated so as to denature the sweat glands and/or the blood vessels feeding the sweat glands, the production of sweat and/or body odor in the section of skin so treated is reduced or eliminated.

Alternatively, production of sweat can be inhibited by orally administering sodium fluorescein to a subject, waiting for the sodium fluorescein to accumulate in sweat glands, and then illuminating a skin section in which inhibition of sweat is desired with light having a wavelength that is well absorbed by the contaminant sodium fluorescein, but is not well absorbed in skin tissue. Sodium fluorescein is a biocompatible photosensitizer, and when administered orally is preferentially delivered to sweat glands by metabolic processes within about one hour in sufficient concentration to serve as a light-absorbing chromophore. Metabolic processes will eventually deliver the photosensitizer to other skin tissue, so it is important to time the illumination of skin tissue for destruction of sweat glands during the window of time when a tissue destroying amount of the photosensitizer has accumulated in the sweat glands, but before a tissue destroying amount of the photosensitizer has accumulated generally in skin tissue.

A tissue-destroying amount of a solution of disodium fluorescein generally contains a concentration of about 2% to about 10% by weight, with the total amount varying depending on such factors as the weight and metabolism of the subject.

Although any light can be used that produces a wavelength of about 441 nm, a preferred light source is a He:Cd laser or a Nd:YAG doubled frequency laser. Upon activation by light at a wavelength of about 441 nm, sodium fluorescein emits energy in the form of a green light that is well absorbed by blood in capillaries that feed the sweat glands, causing the chromophores in the blood to become heated. By this means of energy transfer, the blood in the capillaries is heated sufficiently to damage the blood supply to the sweat glands, e.g., by coagulation of the capillaries. Thus, the blood supply to the sweat glands is cut off or diminished sufficiently to cause the sweat glands to wither, inhibiting production of sweat and consequent odor.

The methods for reducing human sweat and body odor of this invention offer the advantage that inhibition of sweat production is long term; whereas prior art methods in which a cream or ointment is applied to skin inhibit sweat production only for a few hours, at most.

No. 13: Tailored Laser Assisted Hair Removal

Current methods of laser assisted hair removal utilize a set of laser parameters that are selected to fit the absorption characteristics of a particular exogenous chromophore applied to the hair ducts or a particular naturally occurring chromophore, such as water, blood or melanin. If the laser parameters are adjusted at all to fit individual patients, they are commonly adjusted by hand to accommodate such factors as individual differences in skin or hair coloring, differences in follicle depth at different anatomical locations, and the like. It would be advantageous to have a more systematic method for optimizing laser parameters to fit individual requirements, or an automated system whereby upon input of information regarding an individual's coloring, etc., the system would set a laser apparatus to provide optimal laser parameters corresponding to the input information.

A method is provided for tailoring laser-assisted hair removal to the needs of an individual patient. The treatment regimen and selection of treatment parameters is based on consideration of answers to a set of predetermined questions regarding various aspects of a patient's characteristics and treatment history that will affect selection of laser parameters and scheduling of treatments. The set of questions should comprise at least the following: (a) what is the patient's skin coloration, e.g., whether dark or fair; (b) what is the anatomic site of treatment, and what is the average depth of hair follicles at the site; (c) what is the current status of the hair growth cycle for the preponderance of hairs at the site; (4) what is the individual hair physiology of the patient at the treatment site, e.g. the diameter of the hairs or whether the hairs are vellum; and (5) what previous laser treatment for hair removal has the patient undergone.

In one embodiment of the invention, a system is provided for pre-programming a laser to select optimal laser parameters based on input to the system by an operator regarding the answers to these questions, which are specific to an individual patient. However, the same result can be accomplished by the operator manually adjusting the laser parameters that control the energy level produced by the laser in accordance with the answers to the above set of questions provided by the individual to be treated.

The optimal laser characteristic in terms of wavelength, fluence, pulse repetition rate, and pulse duration generally will vary depending upon the hair coloration of the individual undergoing treatment as well as skin color, extent of sunburn, etc. Dark hair, for example, may be more susceptible to a Nd:YAG laser at a wavelength of 532 nm compared to light hair, which is more susceptible to a wavelength of 1064 nm. In general, dark hair absorbs light energy more readily at any wavelength, so less laser energy is needed in treatment of dark hair than in treatment of light colored hair.

The optimal laser characteristics for specific anatomic sites also differ due to differences in the average depth of hair follicles at various anatomical sites. For example, the energy levels utilized in the upper lip region may be less due to the shorter depth of the follicles (1.8 mm) compared to the lower leg region where the follicles may extend to 4.0 mm deep. As described in detail in Section No. 1, herein, the depth of an individual hair follicle also varies depending upon its current phase in the hair growth cycle. In general, the bottom of a hair follicle is at a depth in the range from about 1 mm to about 2 mm during the telogen phase of the hair growth cycle; whereas the bottom of the hair follicle is at a depth of about 4 mm to about 6 mm during the anagen phase of the hair growth cycle. Although, in some cases it may be desirable to omit consideration of the hair growth cycle completely in determining the average depth of hairs at the anatomic site to be treated, if it is to be considered at all, the phase in the hair growth cycle of a preponderance of hairs at the anatomic site generally will be considered together with the location of the anatomic site in determining the average depth of hair follicles at the site to be lased.

It is preferred that the hairs in the section of skin to be treated will be synchronized in a common phase of the hair growth cycle, for example, the late telogen/early anagen phase, prior to lasing for hair removal, as disclosed in Section No. 1 herein. Assessment of the hair growth cycle for an individual may include a direct measurement of the extent of anagen versus catagen hair. This can be done by shaving or cutting the hair from a specific anatomic area and counting the hairs which are present. After one to eight weeks, the hairs in the same area are recounted using the same procedure. The difference between the initial count and the second count gives the number of hairs which are in anagen. Further description of procedures for assessing the current phase of the hair growth cycle in a section of skin and for synchronizing hairs in the hair growth cycle is in Section No. 1 herein.

The hair physiology of the patient will also influence the selection of laser parameters. For instance, if the patient has undergone previous laser treatment for hair removal, the hairs at the site to be treated may already have undergone a substantial weakening in their general vitality, which is generally characterized by a decrease in diameter and less deeply colored appearance. Another factor relating to hair physiology that may influence the selection of laser parameters or treatment regimen is the patient's nutritional status or disease state. For example, use of steroids or biotin deficiency, which cause temporary hair loss, generally indicate that treatments for hair removal should be delayed until normal health has been restored.

The scheduling of hair removal treatments, i.e., the treatment regimen, is also an important aspect of tailoring the hair removal treatment to the individual patient. In particular, the spacing between hair removal treatments should be closely coordinated with the patient's individual response to the previous treatment. For some patients, hairs do not fall out at a treatment site for about 2 to 3 weeks following a laser hair removal treatment, while for other patients the hairs at a treatment site do not fall out for about 6 or 7 weeks following a laser hair removal treatment. Therefore, if the patient has previously undergone laser hair removal treatment, the treatment site should be closely monitored to detect the loss of hair attributable to the laser treatment. New hairs will emerge from the hair ducts in the treatment site within about 2 to 3 weeks following hair loss. Therefore, a subsequent treatment should be scheduled to take place within about 2 to 3 weeks following hair loss due to a previous hair removal treatment and when less than about 30% of the hairs at the former treatment site are visible above the skin surface in regrowth. If this pattern is followed, hair regrowth will be effectively curtailed at the treatment site.

The spacing of hair treatments is also affected somewhat by seasonal and circadian rhythms in light. For example, in the Northern hemisphere, the largest percent of hairs in telogen phase occurs in the months of August and September, with onset of an increase in the percentage of hairs in anagen phase occurring about three months thereafter.

The treatment regimen and the laser parameters for use in hair removal treatments are selected based upon the information obtained by answering the full set of questions, except that any question is omitted that does not apply to a particular individual in the judgment of a skilled operator.

This process ensures that all relevant factors are properly evaluated and weighed against one another in selecting the spacing between hair removal treatments and the wavelength of light, fluence, pulse repetition rate, and pulse duration to optimize any type of laser hair removal technique.

In one embodiment, the laser energy, i.e., combination of the wavelength, fluence, pulse repetition rate, and pulse duration of the laser, is selected to deliver a fluence of about 1.5 to about 5 J/cm$^2$, for example about 2.5 J/cm$^2$, at a depth corresponding to the depth of the majority of the hair follicles in the skin section to be treated, with the wavelength being selected based upon the individual's hair and/or skin color, as described above.

As discussed above, the depth to which the energy must penetrate to damage hair follicles will differ depending upon the predominant phase of the hair growth cycle. In addition, hair follicles in the anagen phase are more susceptible to damage by lasing than at any other phase of the hair growth cycle. Therefore, the optimal laser parameters utilized in treating a site predominantly in anagen phase will include a lower laser energy than is required for a site predominantly in telogen phase.

For example, treatment of each patient may be tailored by performing the following series of steps with regard to an individual patient. For some patients it will be apparent that not all of the steps will be appropriate, in which case an inappropriate step is omitted, and the operator passes to the next step in the series. However, it is important for the operator to at least consider whether each step is appropriate for each individual to be treated.

In one embodiment the series of questions to be considered in determining the optimal laser parameters comprises the following:

Does the patient exhibit any symptoms, such as a skin rash or bad sunburn, that are contraindications for laser hair removal? If yes, terminate the treatment and reschedule at a later date. Contraindications include, but are not limited to, existing pregnancy; a history of metastatic skin tumors, such as basal cell, squamous cell, or melanoma; an HIV positive condition; or a mole containing a hair growing in the treatment area.

Has the patient undergone a previous treatment for hair removal? If yes, schedule the next treatment to occur when hair regrowth is visible from about 30% of the hair ducts at the previously lased site.

What is the color of the patient's hair and skin at the anatomic site to be treated? Where is the anatomic site to be treated? Preferably the anatomic site to be treated will be photographed to document hair and skin coloration. Select a wavelength of light to be used based on skin color and hair color.

Optional: What is the predominant phase in the hair growth cycle of hairs in the site to be treated? It may be desirable to avoid this question to save the costs involved with obtaining an answer to this question.

The site may optionally be pretreated to synchronize the growth of hairs in the hair growth cycle to fix the average depth of the hair ducts (or follicle) at a common depth at the anatomical site. Preferably the hairs are synchronized in the late telogen/early anagen phase.

Select optimum laser operating characteristics, such as wavelength, fluence and pulse duration based on the foregoing information. The correlation between patient characteristics and laser parameters is empirically determined.

Initiate laser injury of the follicles to induce hair growth inhibition.

One of skill in the art will be able to determine whether additional questions need to be answered in arriving at a set of laser parameters that are tailored to an individual patient.

Figure 24:
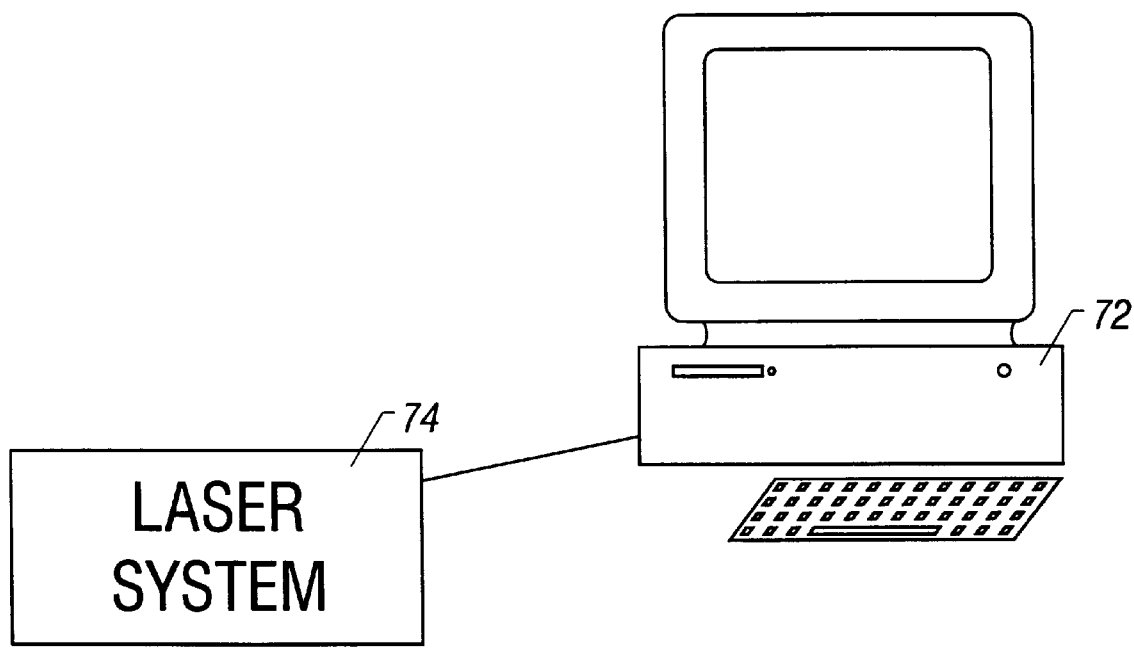
FIG. 24 is a drawing showing a computer system connected to a laser.

This invention provides the advantage that the laser parameters used in treatments to inhibit hair growth and the treatment regimen are tailored to fit individual characteristics of the patient, rather than using a fixed set of parameters for all individuals that is selected to fit the absorption characteristics of a particular exogenous or endogenous chromophore to be irradiated. In addition, as shown in FIG. 24, the method can be used in connection with a computerized system 72 in communication with a laser 74 so that the laser operator can key in responses to a set of predetermined questions regarding the patient's hair, skin, physical condition, and anatomical location to be lased with the result that a preprogramed selection of individually tailored laser parameters is transmitted to the laser before lasing is initiated.

No. 14: Improved Laser Operating Characteristics for Hair Follicle Damage

A number of methods are known for using lasers to inhibit hair growth and/or cause damage to hair follicles in a section of skin, including a method for infiltrating into hair ducts a contaminant containing carbon particles suspended in an oil, and irradiating the section of skin with pulses of laser light.

The optimal laser operating characteristics have now been discovered for inducing targeted hair follicle damage when a contaminant containing carbon particles suspended in a liquid, such as an oil, is infiltrated into hair ducts, and the section of skin containing the hair ducts is irradiated with pulses of laser light. These improved parameters are as follows:

Laser Type: Nd:YAG
Wavelength 1064 nm
Beam Shape: Circle or Square
Beam Size: $\leq 8.0$ mm
Fluence: >2 J/cm$^2$
Pulse Duration: Depends upon many factors, including:
 1. The size of carbon particles or other chromophores in the contaminant.
 2. The concentration of the chromophore in the lotion or solution applied to the skin prior to lasing.
 3. The depth of hair follicle (which is dependent on the anatomical site and the phase in the hair growth cycle).
 4. The thermal properties of the chromophore.

The effect of pulse duration on heating and/or explosion of chromophore particles is described in full detail in Section 4 herein.

For a 10 ns pulse of about 2 to about 3 J/cm$^2$ fluence, a carbon particle size much less than 1 micron is needed for the photothermal effect to be greater than the photomechanical effect. Longer pulse durations are preferred with larger particles. However, when larger particles are used, surface cooling of the skin, for example, as disclosed herein in Sections 3 and 20, may be needed to avoid over heating and damage to surrounding skin.

No. 16: In Situ Formation of a Photoreceptor for Use in Laser Hair Removal or Skin Rejuvenation Treatments Widespread use of lasers to remove tattoos has demonstrated that residual carbon in skin structures is not permanent. However, the mechanism used by the human body to clear residual carbon particles introduced into hair follicles and other skin structures during treatments for laser hair removal or skin rejuvenation is an open question. Additional exogenous chromophores useful in performing laser hair removal or skin rejuvenation treatments would be desirable.

It is known that elemental iron is readily taken up by the body and used to replenish the approximately 1 mg of the element that is lost daily from shedding of senescent cells along the gastrointestinal and genitourinary tracts, and from desquamation of skin. This minimum daily requirement is increased by growth spurts, pregnancy, and pathologic hemorrhage (*Harrison's Principles of Internal Medicine,* 13th Edition, Ed. Isselbacher et al., Vol. 2, 1994, page 1722). Because of these factors, iron oxide has been safely applied to human skin and hair in cosmetics for centuries. Iron oxide is also an especially safe exogenous chromophore for use in any of the hair removal or skin treatments wherein an exogenous chromophore applied to the skin is irradiated, as it is highly unlikely that harmful effects would result from any iron that might remain in hair ducts or embedded in the layers of the stratum corneum. Other benign metals that can be substituted for iron in the practice of this invention are those, such as cobalt and copper, for which the human body has a dietary requirement.

Iron oxide and the oxides of other benign metals can be easily formed within hair ducts or within other structures of the stratum corneum that have an opening to the skin surface. For example, iron oxide in the from of limonite, the trihydrate of ferric oxide, is readily formed by applying to skin a solution of ferric chloride e.g., in water. Upon application to skin, and within such skin structures such as hair ducts and sebaceous glands, a double replacement reaction with natural electrolytes in or on skin surfaces forms ferric oxide trihydrate.

Iron oxide absorbs one or more wavelengths of light produced by infrared lasers. For example, limonite broadly absorbs light having a wavelength from about 0.1 micron to several microns, as do many inorganic compounds, which generally lack the sharp absorption bands characteristic of organic molecules. Thus, such inorganic compounds are useful for visible light lasers as well. Limonite appears brownish orange in color in part because it absorbs green light.

The technique for loading spaces in hair ducts or surface layers of the stratum corneum with an oxide of a benign metal formed in situ is illustrated with respect to iron, but one skilled in the art can readily adapt the procedure for in situ formation of alternative metal oxides that absorb light at a frequency not readily absorbed in skin, for example in the infrared range. First, a skin section to be treated is coated with a water-based lotion or suspension comprising the metal species as a chloride. For iron, the lotion or suspension comprises an acid iron salt solution, such as ferric ammonium sulfate, ferric citrate or ferric chloride in water, with ferric ammonium sulfate being less harsh to the skin than the strongly acid chloride. The water-based suspension or solution optionally further comprises a suitable nonionic surfactant, such as Tween 20™ (polyoxyethylene sorbitan monolaurate), or any other mildly detergent compound, to overcome surface tension and thereby facilitate transport, i.e., "wicking," of the ferric compound into hair ducts. Examples of suitable surfactants for use in the invention include, but are not limited to, polyoxyethylene sorbitan monolaurate, Tween® 20–50, sodium laurel sulfate, and lauric acid.

The lotion is applied to the skin surface and allowed to stand for a few minutes, for example about 5 to about 20 minutes. During this rest period, at least a portion of the ferric salt in the lotion or suspension is transformed to ferric oxide trihydrate within hair ducts, within sebaceous glands, as well as in and around loose cells on the surface of the skin. However, the metal salts can be irritating in high concentrations or after long exposures. To avoid irritation, the metal salt can be wiped from the surface of the skin, and, rather than waiting for the oxide to develop by exposure to natural electrolytes in skin, the iron oxide is formed in situ by application to the skin of a basic solution, such as ammonia water or sodium bicarbonate.

An exogenous chromophore produced in situ will behave similarly to prior art exogenous chromophores in hair removal and skin rejuvenation techniques. For example, such a chromophore will absorb light energy in the form of heat, which is then released by conduction to adjacent tissue, whether the chromophore is on the surface of the skin or deep within hair ducts. Accordingly, when surface skin cells are to be removed to accomplish a "peel" for the purposes of skin rejuvenation, the metal chloride is applied to the section of skin to be treated so that it infiltrates the topmost few layers of skin cells in the epidermis, and is allowed a period of time for the light-absorbing chromophore to spontaneously form. Finally the section of skin is illuminated with a light beam that is well absorbed by the exogenous chromophore, but which passes through skin with minimal absorption. In this case, the section of skin is generally not cleaned or wiped beyond the removal of grossly excessive quantities of the applied material or the in situ formed chromophore before application of the light beam.

However, when the in situ-formed chromophore is to be illuminated within skin structures, the in situ-formed chromophore is generally cleaned from the skin surface prior to application of the light beam. A formulation containing a sufficient amount of a chelating agent for ferric oxide to sequester the chromophore is used for this purpose. For example, a solution of citric acid or ethylene diamine tetraacetic acid tetrasodium salt will chelate iron oxide. The chelated chromophore can be cleaned from the skin, for example, with a clear water rinse, prior to illumination of the area to be treated. Upon illumination of the cleaned skin surface with a light beam having at least one wavelength of light well absorbed by the chromophore in the hair ducts, sufficient heat can be generated to cause long term inhibition of hair growth, using any of the known methods described in the Tankovich patents incorporated by reference herein.

For use in hair removal, formation of the exogenous chromophore within hair ducts of a section of skin to be treated for hair removal eliminates the need to mechanically force the exogenous chromophore into hair ducts by massage, explosion of confined particles, etc. In addition, since humans have a known daily requirement for certain metals such as iron and zinc, there is minimal risk of residual chromophore causing a problem to an individual treated by the method of this invention.

No. 17: Methods for Improving a Hair Removal Process

Figures 25A, 25B, 25C:
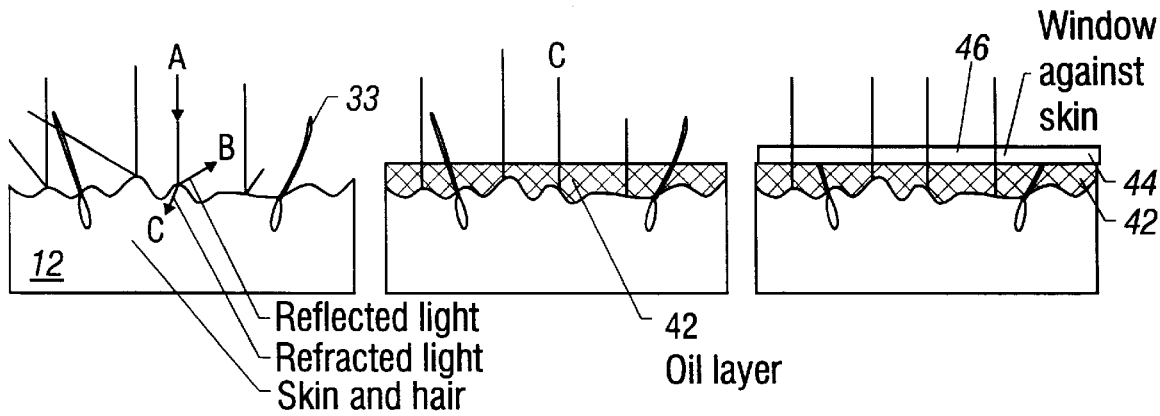
FIG. 25A shows an uneven skin surface with incident light beam C refracted.
FIG. 25B shows the skin surface of FIG. 25A covered with an index-matched liquid coating with light beam C penetrating the liquid coating and the skin surface without reflection or refraction.
FIG. 25C shows a contact plate placed atop a skin surface covered with an index-matched liquid of FIG. 25B.

Under magnification, an apparently smooth skin surface is revealed as an uneven terrain with fissures, holes, indentations or irregularities. The indentations may contain minute particles of lint, dead cells, etc. These imperfections in the skin surface result in scattering of incident light. In addition, due to the change in the index of refraction between air and skin, photons in a light beam incident on skin, such as provided by a laser, tend to be reflected, refracted or scattered. As a result, a large portion of the light energy directed to a skin surface is lost. FIG. 25A shows a cross-section of a skin surface 12 with incident light beam A partially reflected in beam B and partially refracted in beam C.

In this invention a method is provided for reducing light loss by scattering and reflection at a skin surface during skin lasing techniques. To reduce light loss, the skin surface is covered with a liquid coating or device, i.e., a window, that is transparent to incident light. The covering presents a smooth upper surface to incident light, and is made of a material having a refractive index slightly greater than, or equal to, the index of refraction for skin.

It has been discovered by the inventors herein that loss of light incident upon a skin surface, for example during skin lasing techniques, can be reduced by covering the skin surface with a cover having a smooth surface. The covering can be provided by any material, either liquid or solid, that can rest atop a skin surface to be illuminated, but which will present a smooth surface to receive an incident light beam and transmit the beam without substantial attenuation to the skin surface beneath the covering. To accomplish this without substantial loss of light energy, the covering is substantially transparent to incident light, and has a refractive index slightly greater than or about equal to the index of refraction of skin, which is about 1.37. In use, the covering is placed atop the skin surface to be illuminated so that the incident light strikes the smooth surface and is transmitted to the skin through the covering.

In one embodiment shown in FIG. 25C, the covering is a contact plate 44 having at least one smooth planar surface 46, such as a thin plate of an inert and substantially transparent material. In use, the contact plate 44 rests atop a skin surface 12. Transparent plastic, glass, quartz, fused silica, or a polymeric material can be used to make the contact plate 44. Table 5 below shows the index of refraction for representative materials that can be used for the contact plate.

TABLE 5

| Material | Index of Refract |
| --- | --- |
| Corning glass 7913 | 1.45 @1.0 μm |
| Glass (Bk-7) | 1.51 @ 1.0 μm |
| Quartz | 1.53 @ 1.0 μm |
| Fused silica | 1.45 @ 1.0 μm |
| Styrene/vinyl benzene | 1.55 approx. |
| Skin | 1.37 approx. |
| Mineral oil | 1.47 approx. |

An antireflective coating (not shown) on the side of the covering that faces the laser (i.e., planar surface 46) will minimize loss of light energy during transfer all the way through to the skin. The contact plate may take a variety of shapes. For example, the shape of the contact plate may be circular, trapezoidal, square, etc. The skin surface to be irradiated may be somewhat concave or convex, depending upon its anatomical location. Therefore, for convenience in use, the surface area of the contact plate that contacts a skin surface generally covers an area of from a few square millimeters to a few square centimeters, and it may be curved rather than planar to accommodate concave or convex skin surfaces.

The surface of contact plate 44 that contacts a skin surface preferably is sufficiently smooth to permit the device to move over a skin surface without abrading it, even when the device is applied to the skin with pressure. The contact plate may further comprise handles (not shown) to be grasped by an operator while applying pressure when moving the device across the skin, or an attachment (not shown) for directly connecting the plate 44 to a laser apparatus.

In another embodiment shown in FIG. 25B, the covering is a coating 42 of a transparent index-matched liquid having sufficient viscosity that, when applied to the skin surface 12, will present a smooth surface to incident light beam C. When light is incident upon a smooth liquid coating applied over the surface of the skin, reflection losses are minimized. More light reaches the hair follicles beneath the coating than in the absence of the coating because the light is directed to the follicles in the path of the laser without redirection at the skin boundary. If light is directed perpendicularly to the smooth surface of the liquid covering, the light beam will pass directly into the skin without being redirected by refraction or scattering at the boundary of the skin as shown in FIG. 25B. However, scattering will occur once the light enters the skin.

Selection of the index of refraction of the liquid controls the transmission of light to the skin under laser treatment. For example, the liquid can be a transparent oil, such as mineral oil, which has an index of refraction of about 1.47 as compared with 1.37 for skin. The hydrating effect of the oil on the skin surface also improves the smoothness of the skin itself. In the case where the index of refraction of the oil is matched as closely as possible to that of skin, the liquid coating will form a smooth optical boundary between the incident light and the skin to be illuminated. Alternatively, if the index is between that of air and of skin, the liquid will act as an antireflective coating to minimize reflection of incident light. The coating of a transparent liquid may need to be reapplied during the illumination phase if surface heating occurs.

In certain prior art hair removal procedures, the skin is pretreated with particles of an exogenous chromophore forced into hair ducts to provide a heat absorbing medium around the hair follicles. When the index-matched liquid covering is used in conjunction with this method of hair removal, once the chromophore particles are worked into the hair ducts, the carbon particles should be cleaned off the surface of the skin, e.g., with a surfactant. A surfactant helps to work the carbon into the hair follicles. Once cleaned, the area can be covered with a clear index matching coating of liquid and treated with the laser light. Optionally, the skin surface can be coated with the liquid covering of the invention and then the contact plate can be applied atop the smooth liquid coating, as shown in FIG. 25C. By this method, loss of light energy is minimized during transfer all the way through to the skin. This sequence of steps will aid in concentrating the effects of the laser light on the hair follicle, thereby enhancing the treatment process.

Figure 26:
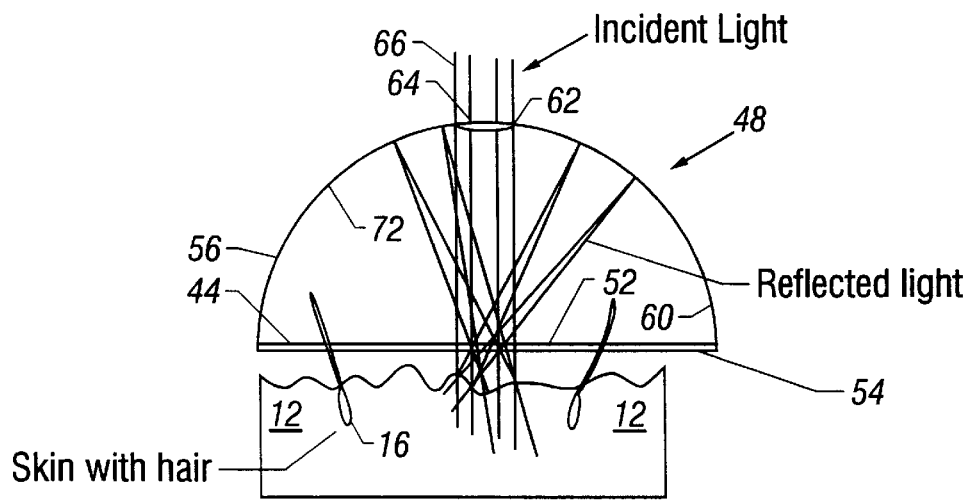
FIG. 26 is a cross-section showing a domed reflector covering a section of hair and skin.
Figure 27:
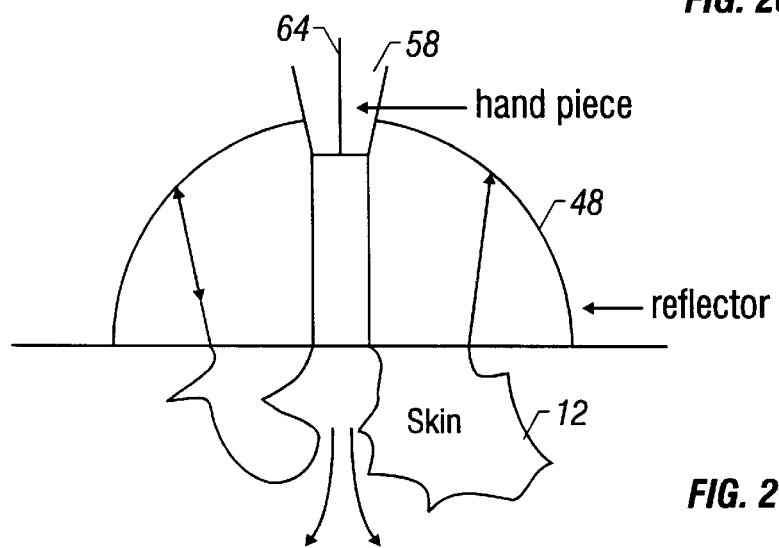
FIG. 27 shows a domed reflector with an attached handpiece.

In yet another embodiment, the contact plate is incorporated within a domed reflector 48 as shown in FIGS. 26 and 27. In this embodiment, transparent contact plate 44 is a flat plate with smooth parallel sides, a light receiving side 52 and a skin-contacting side 54. The skin-contacting side is smooth enough to move freely over a skin surface without abrading it.

The domed reflector further comprises a thin transparent dome 56 joined to the transparent contact plate along the periphery of its light receiving side 52. The dome is a shell, and when attached to the contact plate, encloses or partially encloses, an interior void space. Preferably the contact plate is circular and the dome is hemispherical. A handpiece 58 can be attached to the dome to facilitate handling as shown in FIG. 27.

The rounded interior surface 60 of the dome (e.g., hemisphere) is covered with a coating 72 highly reflective to light at the wavelength of the laser. An opening is provided in the reflective coating at the apex 62 of the dome 56 through which incident light can pass. Alternatively, the dome has an aperture 64 located at its apex through which incident light passes, and the interior surface of the dome is coated with the reflective coating. If the contact plate is circular and the dome is hemespherical, the aperture is generally circular as well. The reflective coating can be made of any reflective substance, such as silver, depending on the laser to be used.

In use, as shown in FIGS. 26 and 27, the domed reflector 48 is placed atop a skin surface 12 to be irradiated, and light is directed to the skin through the domed reflector. The light enters the opening in the reflective coating of the dome, or through the aperture 64 at the apex of the dome, passes through the interior void space within the dome, and passes through the transparent, index-matched contact plate 44 to the skin surface 12. Any of the incident light photons 66 reflected or refracted away from a skin surface contacted by the skin-contacting side of the contact plate will be returned to the skin by the reflective coating on the interior surface of the dome. If the dome is hemispherically shaped, light reflected from the interior reflective surface of the dome will be reflected back to the skin near its point of origination. Thus the amount of light lost is decreased, and the efficiency of any laser skin treatment is increased.

The contact plate protects the reflective interior surface of the dome from contamination by particles of skin, etc., that would be created by action of the laser upon an uncovered skin surface. In addition, the contact plate incorporated within the domed reflector will prevent laser action from exploding a chromophore off the skin surface during lasing. Further, the contact plate assists in forcing the chromophore particles into hair ducts or other skin structures during lasing.

Figure 28:
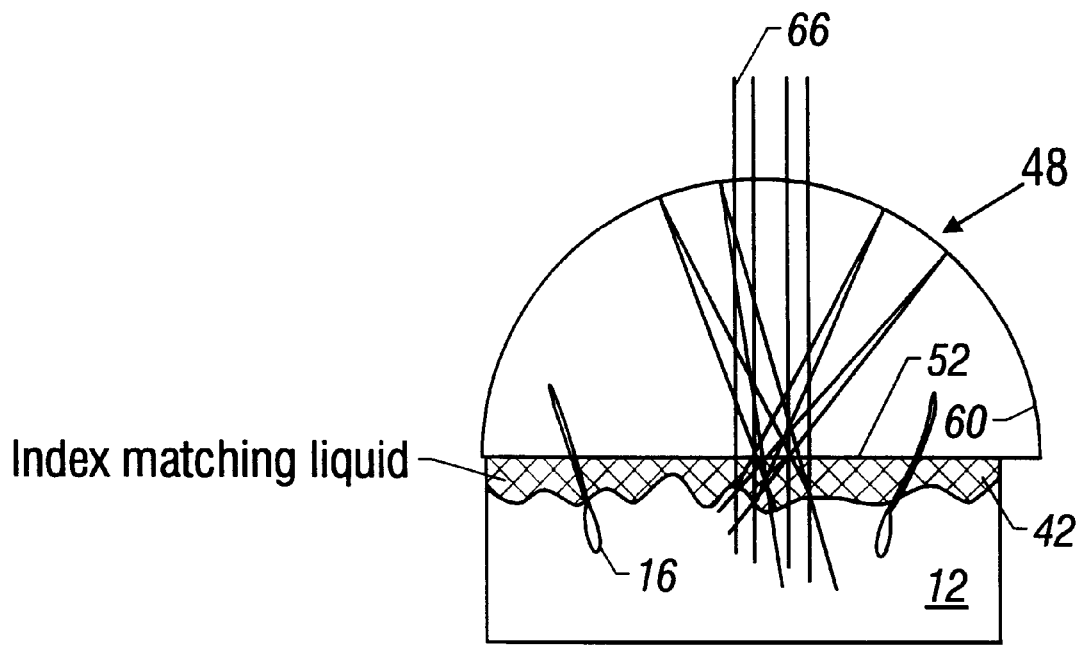
FIG. 28 shows a domed reflector on top of a liquid covering a cross section of skin and hair.

In another embodiment, the scatter-reducing liquid coating is applied to the skin surface and the domed reflector is placed atop the liquid to direct any reflected light back to the skin (FIG. 28). As in other embodiments of this invention, the liquid coating is index-matched to the skin so as to make a smooth optical boundary between the skin and the skin-contacting surface of the domed reflector. Alternatively, the skin surface is covered by an index-matched liquid and a contact plate with an antireflective coating on its smooth light receiving side is placed over the liquid on the skin surface for lasing (FIG. 25C).

The methods and devices of this invention provide the advantage of reducing loss of incident light at a skin surface, such as during the period of laser illumination for skin resurfacing, hair removal, or inhibition of hair growth. Use of a solid covering, i.e., a contact plate or a domed reflector, during such procedures offers further advantages. For example, pressure applied to the covering (i.e., in a direction parallel to the direction of the laser beam path) and transferred to the underlying skin has a number of beneficial effects which aid in hair removal. The pressure compresses skin in contact with the covering device, thereby effectively shortening the hair duct and/or the distance from the skin surface to the bottom of the hair follicle because the solid covering compresses the upper layers of the skin. Furthermore, shortening the distance the light must travel to reach the bottom of the hair duct decreases the attenuation of light traveling to the target cells. As a result, milder lasing conditions are required than when the covering is not used. A third effect of using the covering devices during hair removal is that blood flow into the section of skin being illuminated can be restricted by compression of the capillary bed if pressure applied by the overlying device is greater than the patient's blood pressure. The restricted blood flow results in more effective delivery of laser light to the follicle and surrounding cellular targets, since blood can absorb a small fraction of the laser light. In addition, compression of the skin surface by the device reduces scattering of light within the skin. All of these factors aid in accomplishing the goal of inhibition of hair growth while minimizing damage to the skin surface.

No. 18: Hair Regrowth Method Using Grafting of Papilla and Bulge Area Stem Cells It is known that papilla and mid-derm bulge area stem cells play an important role in the hair growth cycle. Several groups of researchers have reported on the key role in regulation of hair growth found in bulge area stem cells. In electrolysis, for example, particular attention is directed to destruction of hair stem cells. New ways of exploiting the key role of bulge area stem cells in stimulating hair growth are needed to combat alopecia, particularly male pattern baldness.

The present invention provides a method for utilizing an individual's undifferentiated papilla and/or bulge area stem cells to stimulate hair growth. The inventors have discovered that bulge area stem cells can be harvested, isolated, cloned, and successfully transplanted into an area of the donor's skin where increased growth of hair is desired to increase hair growth therein.

In the first step of the method, a donor section of skin is identified having growth of the type of hair for which increased growth at the recipient site is sought. Since hair types differ according to their anatomical site, it is generally desirable to match the hair produced by the donor stem cells to the type of hair that is desired at the recipient site. For example, in treatment of male pattern baldness, tissue samples are harvested from an area of the scalp that still exhibits vigorous growth. Once the donor site is identified, it is anesthetized locally using any convenient means and a plurality of tissue samples are obtained from the donor site. The tissue samples must contain hair follicles with intact undifferentiated papilla and/or dermal stem cells, as well as immediately surrounding tissues. Any method of tissue sampling can be employed, for example, punch biopsy, so long as viable stem cells can be obtained.

Undifferentiated stem cells are separated out from the mid derm bulge area of hair papilla in the tissue samples. For example, the tissue samples can be microsurgically dissected to locate and separate out the stem cells. The separated stem cells are then cloned by culturing them in an appropriate growth medium, such as Dulbecco's modified Eagle's medium (DMEM) with fetal calf serum, for a sufficient time to allow proliferation and differentiation of the cells.

Generally, the cells are cloned to a cell density of about 40 cells per cubic centimeter. A single growth cycle will require approximately 21 to 28 days. During culture, the medium is kept at about body temperature, or 37° C. One skilled in the art will understand that any one of a number of alternative growth media can be used to foster proliferation and differentiation of the stem cells. Once the desired cell density is achieved, for instance after about 2 to 3 passages, the cloned ells can be examined microscopically to detect the vital cells. Healthy differentiated stem cells are generally identified by applying a vital dye, such as Hoehst 33258 or Hoehst 33342 fluorescent dyes, incubating the cells for about 30 minutes, and then determining which of the cells fluoresce.

A sterile suspension of the cells in a biologically acceptable carrier medium, such as normal saline, is then prepared for inoculation or transplant into one or more recipient sites of the same individual from which the stem cells were harvested. Suitable carrier media include aqueous or non-aqueous solutions, suspensions, and emulsions. Examples of non-aqueous solutions are propylene glycol, polyethylene glycol, and injectable organic esters, such as ethyl oleate. Aqueous carriers include water, alcoholic-aqueous solutions, and suspensions, including saline and buffered media. For interdermal grafting, the suspension of differentiated stem cells should be at a density of about 3 to about 10 percent by volume.

For grafting of the differentiated stem cells, the recipient site is prepared by scraping the skin surface and making superficial incisions of about 200 microns in depth. The solution of stem cells is delivered to the recipient site, generally by pipette, and the site is covered with a sterile bandage, such as Tegaderm™.

In an alternative embodiment, the solution delivered to the recipient site additionally contains polypeptides that trigger initiation of angiogenesis and neurogenesis, which are expressed into the media by the stem cells during the cell culture mitotic process.

If desired, a portion of the cloned stem cells can be frozen and reserved for future inoculation into the individual undergoing hair growth treatment. If frozen to a temperature of about $-70°$ C., a bank of auto stem cells can be kept for several months, allowing for fast expansion in culture when required.

The method of the invention is illustrated in the following example:

1. Stem cells were collected by punch biopsy from 102 healthy hair root canal bulge areas of an individual to be treated, and the samples were micro-surgically dissected to separate out and collect the undifferentrated stem cells from the mid-derm bulge area of hair papilla.
2. The collected stem cells were placed for cloning into Dulbecco's modified Eagle's medium (DMEM) with fetal calf serum as a culture medium.
3. When cells had proliferated and differentiated (approximately 21–28 days per one cycle) to about 40 cells per 1 $cm^3$, the healthiest were selected and separated into three groups.
4. One group was frozen to $-70°$ C. to create a bank of auto stem cells for fast reproduction when required. The second group was cloned in order for the secondary population to reach the cumulative population doublings (CDP) required, usually 2 to 10 times.
5. The third group was used for the preparation of a sterile suspension of stem cells in a carrier medium. The suspension was inoculated interdermally by pipette into recipient sites prepared on the scalp of the donor individual. Alternatively, the suspension was applied topically to the area being treated for hair regrowth, along with polypeptides expressed into the media by the stem cells during the cell culture mitotic process.
6. The areas inoculated with hair stem cells experienced increased hair growth and hair regrowth after about 21 to 28 days.

The method of hair growth via cell transplant of this invention provides the advantage that cloned stem cells can be expanded in culture so that the amount of donor material to be transplanted is not limited by the number of cells that can be harvested. Thus an individual with relatively few donor sites can provide enough stem cells to stimulate hair growth in a large area of skin, if so desired. In addition, the cloned cells can be implanted into the recipient sites without making more than superficial surgical incisions in the recipient sites. In contrast, many prior art hair grafting procedures require use of more extensive surgical techniques to implant the donor tissue.

No. 19: Method for Laser Removal of Hypertrophic and Keloid Scars

The majority of scars heal normally over time, presenting no additional difficulties. However, in certain instances healing proceeds abnormally, generating excessive or hypertrophic scar formation. Hypertrophic scars remain as raised, red, "angry-looking" tissue that does not fade over time. Keloids are scars that continue to enlarge, forming smooth, hard growths, often presenting a bulging, tumorous appearance. Keloids may develop on any part of the body, although the upper chest and back are especially prone to keloid formation. Keloids occur more frequently in heavily pigmented individuals.

Recently, it has been reported that postoperative low megavolt electron beam irradiation is effective in the prevention or recurrence of hypertrophic scars and keloids (*Radiotherapy and Oncology*, 19 (1990) 267–272). Keloid and hypertrophic scar treatment using a carbon dioxide laser has also recently been described (Stem and Lucente, *Arch Otolaryngol Head Neck Surg* Sep 11, 5:9:1107–11, 1989); however, a recurrence rate of approximately 70% following $CO_2$ laser therapy was reported. Accordingly, it would be advantageous to have new and better methods of laser treatment for the removal of keloids or hypertrophic scars.

The present invention provides a method for removing keloid and hypertrophic scars by applying a light-absorbing contaminant to scar tissue to be removed so as to cause the contaminant to infiltrate the surface layers of the scar, and then illuminating the contaminated scar tissue with short pulses of light well absorbed by the contaminant, but which pass through normal skin tissue with minimal absorption. The inventors herein have discovered that repeated treatment of a scar with laser light will cause growth of normal epithelial cells in the area where the scar appeared. The method used is as follows: a contaminant is applied to keloid or hypertrophic scar tissue, and the area is irradiated by laser energy for about 5 or 6 passes, or until erythema or minor inflammation is detected in the scarred area. Then a period of about 4 to about 6 weeks is allowed to pass before the treatment is repeated. A total of from about 2 to about 8 treatments, for example about 4 to about 6 treatments, is generally sufficient to cause reorganization of the epithelial layer and removal of the scar. A new layer of skin with the appearance and elasticity of normal skin will form. By a mechanism yet unknown, the combination of the photochemical and photothermal effects caused by absorption of laser energy in the contaminant and/or the scar tissue and underlying tissue results in (1) disappearance of the scar and (2) formation of new spindle-type collagen fibers in the underlying dermis at the place where the scar had been.

The contaminant preferably comprises a light-absorbing chromophore of the type known to be useful in laser hair removal procedures, such as a suspension of carbon particles in an oil- or water-based medium. The short pulses of light are provided by a light beam with a wavelength that is well absorbed by the contaminant, but which has minimal absorbence in skin. For example, a Nd:YAG laser with a wavelength of 1064 nm can be used in the practice of this invention. The contaminant is applied to the scar tissue so as to cause penetration of the contaminant around and between the cells in the upper layer of the scar tissue. Brisk massage or ultrasound can be used to force the contaminant under and between cells on the surface of the scar tissue.

The laser parameters and size of the particles in the contaminant should be selected so as to assure that the particles in the contaminant will explode upon illumination with short pulses of light. Some of the particles on the surface of the skin will be forced into the skin as a result of the shockwaves resulting from the explosion of other particles. In addition, the pulses of light interact with the skin and the particles below the skin. The particles below the skin surface that explode or vaporize upon illumination will rip off the layers of the hypertrophic scar or keloid which lay above the exploding particles. The pulses are continued until essentially all of the chromophore particles are exploded. This procedure should be repeated until sufficient layers of hypertrophic scar or keloid have been removed to remove the appearance of the scar.

Laser energy not absorbed in the contaminant is harmlessly dissipated in the skin and surrounding tissue. There is generally minimal pain or feeling of heat, and no significant injury to the skin tissue. It is preferable to provide a slight diverging beam to assure that the beam spreads before it hits the skin. For example, in one embodiment, the spot size of the light beam at the skin surface is about 0.5 cm in diameter and, before interacting with the skin, the beam spreads at an angle from the vertical of about 10 degrees. Post-operative treatment of the targeted area includes any commonly accepted methods known to those in the medical arts.

While the invention is illustrated with reference to the combination of a Nd:YAG laser and a contaminant containing carbon or graphite particles, persons skilled in the laser-medical arts will recognize that many other laser-contaminant combinations can be used to practice this invention. The important attributes of the combinations are:

The contaminant must absorb light energy well at the wavelength of the laser beam.
  The laser beam must be a pulsed beam with very short pulses (pulse durations of less than 1 microsecond.
  The contaminant must be capable of being infiltrated into the upper layers of the scar tissue.
  The contaminant must explode with sufficient energy to tear off cells of the scar tissue upon absorption of the laser energy.
  The treated area must have about 2 to 8 treatments spaced at intervals of about 4 to 6 weeks wherein during each treatment the area is irradiated by laser energy for about 5 or 6 passes, or until erythema or minor inflammation is detected in the scarred area Upon laser treatment as described herein, treated scars are substantially removed, and new spindle-type collagen fibers are formed in the underlying dermis of the targeted area It is also notable that turgor of the skin is restored at the location where the scar had been prior to the laser treatment. Such results suggest that laser treatment of the afflicted area stimulates reorganization of tissue. According to Goslen (*Physiology of wound healing and scar formation.* In: Thomas, J. R. et al., eds. *Facial Scars—Incision, Revision, arid Camouflage.* St. Louis: C V Mosby, 1989), wound repair progresses normally through the following five stages: a vascular phase, an inflammatory phase, a re-epithelialization, formulation of granulation tissue, and remodeling of matrix and collagen. The final phase of wound healing, matrix and collagen remodeling, begins as water is resorbed from the scar due to the replacement of hyaluronic acid by proteoglycans. Cross-linking of collagen fibers proceeds by lysyl oxidase. Type III collagen is catabolized and replaced by type I, and the collagen bundles are reoriented to lie parallel to the skin surface. The metabolic aberration which leads to keloid formation is believed to occur in this late phase of scarring when keloids fail to mature and become compacted. Apparently, by some presently unknown mechanism, the present method of laser treatment returns the afflicted area to a state of wound healing such that in the final phase of wound repair appropriate collagen formation occurs, substantially avoiding formation of subsequent scars.

This invention provides a method of laser-assisted scar removal without surgery. Because the treatment stimulates reorganization of tissue to promote proper healing, the likelihood that hypertrophic or keloid scars will reform is substantially reduced over the prior art methods of removing scar tissue. Since the majority of the laser energy is absorbed by the contaminant, rather than skin tissue, the risk of damaging healthy tissue is reduced over methods which use a laser beam that is well absorbed in tissue.

No. 21: Hair Removal Using Hair Blood Supply Coagulated by Photons Guided by a Light-Guiding Fluid in Hair Ducts Hemoglobin in blood is a naturally occurring chromophore useful in hair removal techniques. Hair follicles are fed by a network of fine capillaries and blood vessels concentrated at the base of the follicles. U.S. Pat. No. 4,388,924 issued Jun. 21, 1983 to Weissman et al. discloses a method of depilation comprising directing laser energy with a wavelength of approximately 4800 to 5200 angstroms via a laser transmitting probe through the skin to terminate at the base of a hair follicle so as to devitalize the hair by coagulating the blood vessels at the hair root. However, in the Weissman method the depilation is performed one hair follicle at a time, rather than by applying the laser to a skin section containing a multiplicity of hairs for simultaneous treatment. More efficient ways of utilizing the natural chromophore in blood for inhibiting hair growth are needed.

In this invention the combination of absorption coefficient and photon wavelength used for laser hair removal is selected so as to accomplish selective photocoagulation of the blood vessels at the end of hair follicles that have been filled with a light guiding medium, such as mineral oil, to guide photons to the hair roots. In this embodiment of the invention, an external chromophore is not infiltrated into hair ducts to absorb the energy of the laser light. Instead, the naturally occurring chromophores in blood are the target to which a laser is tuned. A combination of absorption coefficient and photon wavelength is selected to assure absorption of sufficient energy by blood chromophores in capillaries at the bottom of the hair follicle to heat the blood in the capillaries and surrounding epithelial tissue to a temperature of about 70° C. to about 80° C. for 0.1 to 1.0 second, with the shorter time corresponding to the higher temperature.

The wavelength of the laser is selected to be well absorbed in blood chromophores, but with a minimum of absorption in skin tissues. Blood absorbs photons strongly at about 400 nm with an absorption coefficient of about 2000 $cm^{-1}$, and blood vessels can be easily coagulated by photons having a wavelength of about 400 nm to about 1300 nm, for example 400 nm to about 650 nm. Moreover, photons within this wavelength range cannot penetrate deep into the dermis. Therefore, use of laser light within this range of wavelengths will coagulate the blood vessels at the base of the hair root, but will not destroy blood vessels below the epidermal layer of the skin.

However, a large proportion of light at the above wavelengths will not penetrate directly through skin to the capillaries at the base of hair roots. To overcome this problem, a portion of the light incident on the skin surface is delivered to hair roots via hair ducts filled with a light-guiding liquid. Preferably hairs are removed from hair ducts in the skin section to be treated before the hair ducts are filled with a light guiding liquid.

Figure 29:
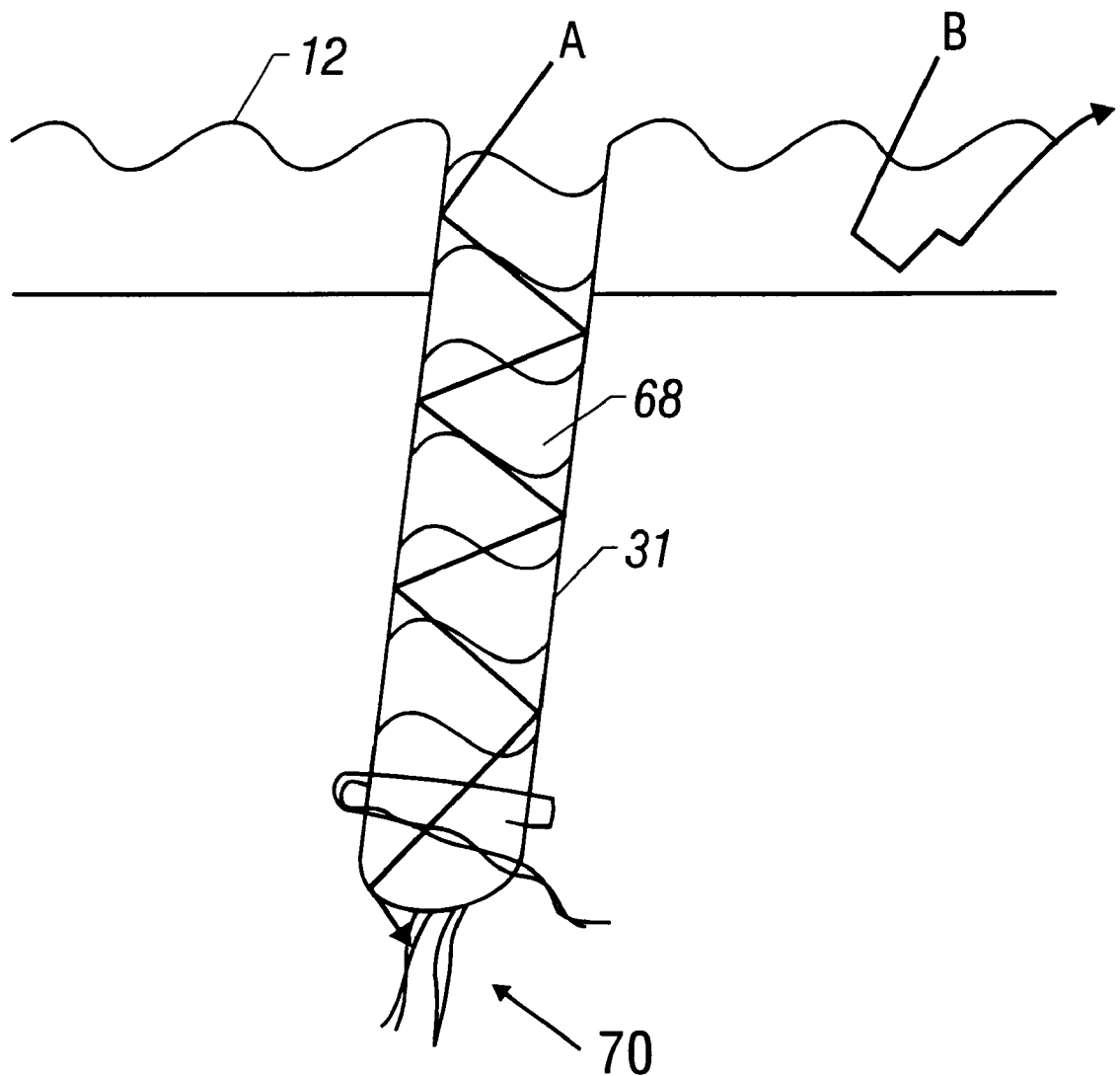
FIG. 29 is a schematic drawing showing a cross-section of a hair duct filled with a light guiding liquid. A photon of light 2 that enters the hair duct is guided to the base of the hair duct by internal reflection and absorbed there in blood vessels in the bottom of the hair duct. Photon 1 incident upon the epidermis is absorbed, while photon 3 is scattered by epidermis.

The preferred light guiding liquid is relatively transparent to light and has an index of refraction greater than that of skin so that a photon entering the light guiding liquid in the hair duct is transmitted there through by continuous internal reflection. For example, experiments have been conducted using mineral oil (index of refraction of about 1.47) as a light guiding liquid. These studies indicate that mineral oil is relatively transparent to light having a wavelength in the range from about 400 nm to about 650 nm. In addition, because the index of refraction of mineral oil is substantially greater than that for skin (index of refraction of about 1.37), an oil-filled hair duct will conduct light beams down the hair duct to the papilla area by continuous internal reflection, operating much the same as a fiber optic. This effect is illustrated in FIG. 29, which shows the path of a typical photon 1 traveling down the hair duct 31 through the light guiding fluid 68, similar to photons in an optical fiber, and being absorbed in blood vessels 70 at the bottom of the hair duct. Other photons that do not strike the light guiding fluid will be absorbed (photon 1) or scattered by epidermis 12.

The chromophores in the blood vessels that feed hair follicles thus receive illumination both from photons that penetrate and are scattered by the dermis, and from photons traveling down through the light guiding liquid in the hair duct. The laser is preferably operated in the continuous wave (CW) mode, and the power is set such that the temperature rise of blood at the hair root is high enough to denature the capillaries, but below the threshold for vaporization of the tissue, so that the light guiding liquid will not be boiled or blown out of the follicles.

The preferred steps to be followed in practicing this invention generally comprise the following:

1. Hairs are optionally extracted from the follicles to be treated using any known method, such as tweezing, waxing, etc.
2. A light-guiding liquid having an index of refraction higher than that of skin, such as mineral oil, is applied to the skin surface and worked into hair ducts in the region to be treated for inhibition of hair growth. If possible, the hair follicles should be filled throughout with the light guiding liquid. However, partially oil-filled follicles are also effective to deliver the light into hair ducts.
3. The surface of the skin is optionally precooled prior to application of the laser using any of the methods disclosed herein or known in the art.
4. A skin section containing a multiplicity of oil-filled hair ducts is illuminated with short pulses of laser light that is well absorbed by naturally occurring chromophores in blood.

It has also been discovered that inhibition of hair growth can be performed without aid from an exogenous chromophore by illuminating a section of skin containing hair ducts with short pulses of light at low fluence having a wavelength of about 1064 nm, such as is provided by a Nd:YAG laser. Using a light-guiding liquid in the hair duct is optional in this embodiment of the invention. It has been discovered that the skin contains naturally occurring chromophores and/or skin structures other than melanin that absorb light from a Nd:YAG laser at a wavelength of about 1064 nm.

A skin section containing hair ducts is illuminated with short pulses of low fluence light in a beam spot size of from about 7 to 10 mm in cross-sectional dimension from a Nd:YAG laser at about 1064 nm wavelength. The fluence of the light is in the range from 0.1 to about 10 J/cm$^2$ and pulse duration is about 900 $\mu$s to about 8 ns, for example, less than 1 $\mu$s. Tissue associated with hair growth cells is affected (e.g., ablated) such that hair growth is inhibited without unwanted damage to skin tissue. The preferred fluence range is less than about 7 J/cm$^2$, for example about 1 to about 3 J/cm$^2$. When parameters in these ranges are used to illuminate the surface of a section of skin containing hair ducts, naturally occurring chromophores in proximity to hair growth cells in hair ducts absorb the short pulses of light and transfer energy to the hair growth cells so as to inhibit hair growth. Regrowth of hairs from skin sections treated according to this embodiment of the invention is substantially impaired.

Low fluence Nd:YAG illumination can also be used to perform laser-assisted skin rejuvenation without use of an exogenous chromophore. The laser parameters are the same as for hair removal except that the beam spot size is smaller to target the beam more shallowly, for example to a depth of about 100 to 200 microns.

The following examples illustrate the manner in which the invention can be practiced. It is understood, however, that the examples are for the purpose of illustration, and the invention is not to be regarded as limited to any of the specific materials or conditions therein.

EXAMPLE 6

Blood coagulation is accomplished using a laser with a wavelength of 415 nm, a pulse duration of about 1 ms, and energy density of about 0.6 J/cm$^2$. This laser can be a dye laser.

EXAMPLE 7

Figure 30A:
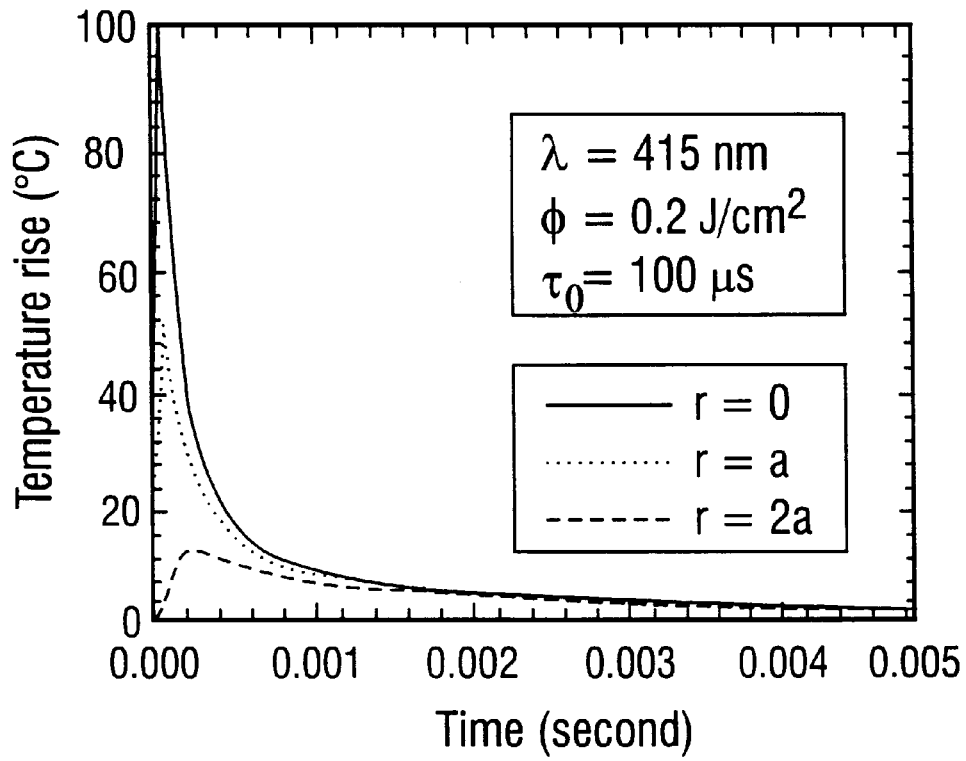
FIG. 30A is a graph showing the calculated temperature rise at the center and wall of a 5 $\mu$m diameter blood vessel as well as in the surrounding tissue when illuminated by photons at 415 nm wavelength with 0.2 J/cm² fluence and pulse duration of 100 $\mu$s. Solid line=T at center of blood vessel; dotted line=T at distance one radius away from wall of blood vessel; dashed line=T at distance two radii away from wall of blood vessel.
Figure 30B:
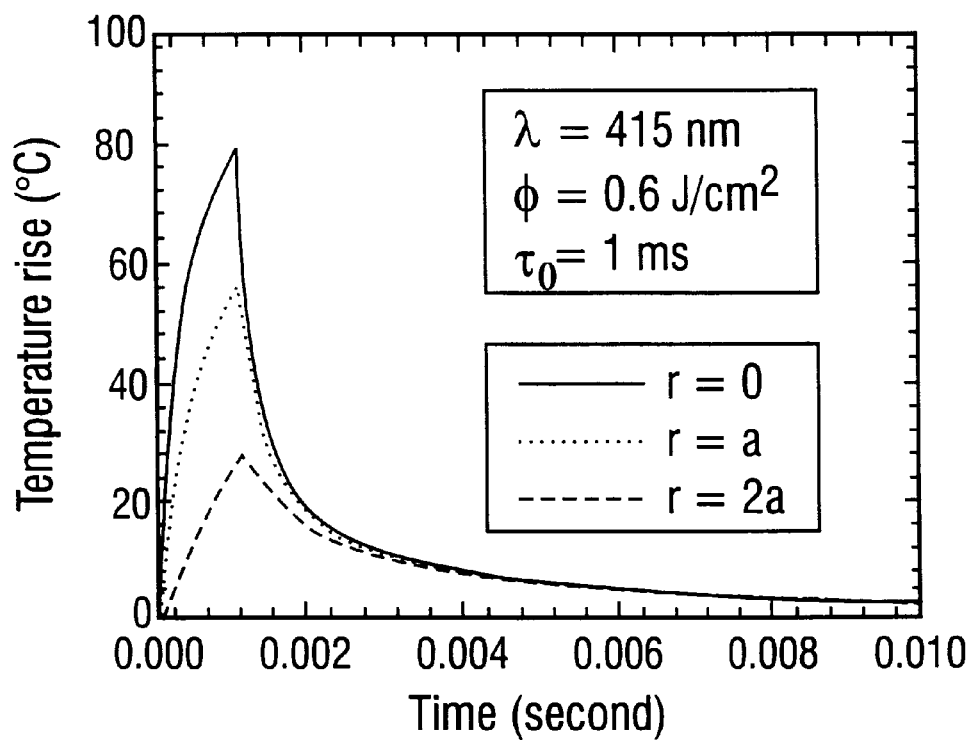
FIG. 30B is a graph showing the calculated temperature rise at the center and wall of a 5 $\mu$m diameter blood vessel as well as in the surrounding tissue when illuminated by photons at 415 nm wavelength with 0.6 J/cm² fluence and pulse duration of 1 ms. Solid line=T at center of blood vessel; dotted line=T at distance one radius away from wall of blood vessel; dashed line=T at distance two radii away from wall of blood vessel.
Figure 31:
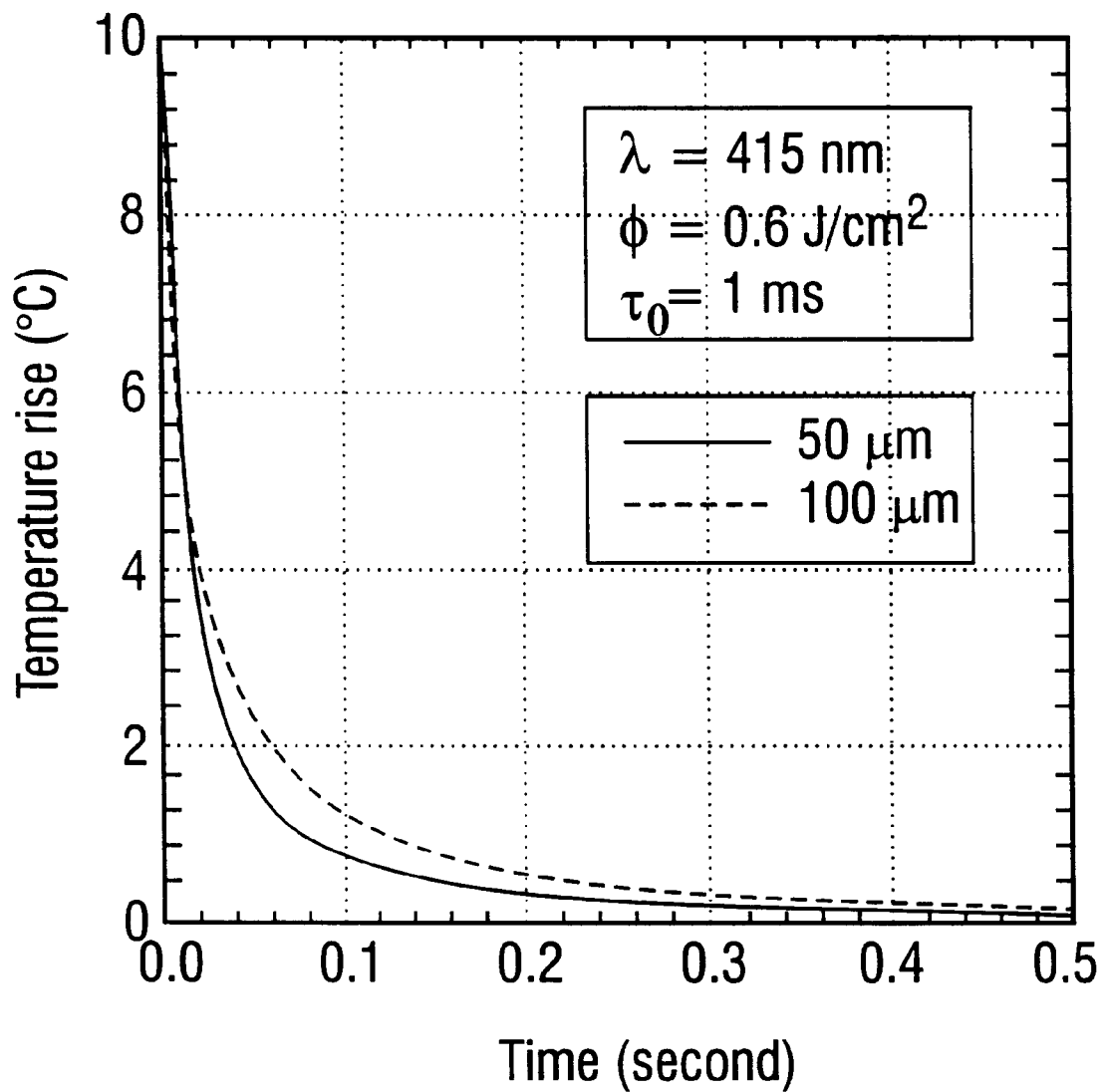
FIG. 31 shows the corresponding increase in skin temperature beneath the skin surface when the skin surface is maintained at 0° C. by cooling. Solid line=T increase at 50 $\mu$m beneath the skin; dashed line=T increase at 100 $\mu$m beneath the skin. With pulse durations longer than 100 $\mu$s, the temperature rise at the interface of the epidermis and dermis, where skin melanosomes are located, is very small so there is little risk of their destruction.

Blood coagulation is accomplished using a laser at about 532 nm with a pulse duration of about 100 $\mu$s, and energy density of about 5 J/cm$^2$. This laser can be a KTP solid state laser with a wavelength of 532 nm The calculated increase in temperature in blood in a 5 $\mu$m blood vessel and surrounding tissue one blood vessel radius away from the wall corresponding to irradiation of a skin surface with a short pulse laser is shown in FIGS. 30A and 30B. FIG. 30A shows the calculated temperature rise at the center and wall of a blood vessel as well as in the surrounding tissue when illuminated by photons at 415 nm wavelength with 0.2 J/cm$^2$ fluence and pulse duration of 100 $\mu$s. FIG. 30B shows the similar values for 0.6 J/cm$^2$ fluence and a pulse duration of 1 ms. This calculated data shows the instantaneous temperature rise in blood. At both fluences, the increase in temperature over normal body temperature is of sufficient duration to cause permanent damage to epithelial cells. FIG. 31 shows the corresponding increase in skin temperature beneath the skin surface when the skin surface is maintained at 0° C. by cooling. With pulse durations longer than 100 $\mu$s, the temperature rise at the interface of the epidermis and dermis, where skin melanosomes are located, is very small so there is little risk of their destruction.

The present invention affords several advantages over prior art methods of laser assisted inhibition of hair growth. First, a naturally occurring chromophore is irradiated by the laser and used to selectively denature the blood vessels that feed hair follicles. In the method of this invention, the laser fluence needed to coagulate the blood vessels that feed hair ducts is very low. In addition, since blood absorbs light waves at a frequency that is poorly absorbed in skin, there is reduced risk of unwanted damage to skin tissue or pigmentation.

No. 22: Hair Removal by Combination of Long Pulse Laser With Skin Cooling

There can be some disadvantages of using short pulse lasers for hair removal. Because the energy is transmitted so quickly into light absorbers, the light absorbing medium can be vaporized. The heat of vaporization consumes a large portion of the energy, with little energy remaining for transfer by thermal conduction to the target tissue. Even if the surface of the skin is precooled, short pulse lasers can burn the skin. In addition, short pulses of laser light may cause pinpoint bleeding from the blood vessels in the upper dermis, or these blood vessels may be coagulated. Another danger is that short pulse lasers can vaporize the melanosomes at the interface of the epidermis and dermis, resulting in unsightly destruction of normal pigmentation of the skin. These problems are overcome in the present invention by using long pulse lasers in combination with dynamic cooling of skin.

Selection of pulse duration for laser skin treatment is important for controlling the amount of unwanted damage that is suffered in order to attain a desired goal. Laser hair removal techniques in which an exogenous chromophore is infiltrated into hair follicles present unique problems in the selection of pulse duration because of the difficulty of driving exogenous chromophore particles throughout hair ducts.

The present invention provides an improved method for inhibiting the growth of unwanted hair using an exogenous chromophore, such as carbon particles, infiltrated into hair ducts. The method combines the use of a long laser pulse with dynamic cooling of the skin surface. The pulse of light used to heat the contaminant is long enough to avoid exploding and/or vaporizing the particles. The laser parameters are selected to provide a long pulse of light at sufficient power to heat the tissue surrounding the base of the hair follicle so as to cause tissue damage. To avoid concurrent damage to other skin tissue, the surface of the skin, which is at or near body temperature at the beginning of the process, is precooled. Cooling is continued throughout the illumination of the skin with a single long pulse of laser light. Then the skin surface is allowed to return to normal temperature before the three step process of precooling, heating while cooling, and return to starting temperature is repeated.

Precooling of the skin surface establishes a steep temperature gradient within the skin, with temperature increasing at increasing skin depth. Preferably the precooling flux is sufficient to equilibrate the temperature of the skin surface to that of the cooling flux while allowing the temperature at the depth of the hair root to remain at body temperature. For example, a 1 second exposure of the skin surface using a coolant at 0° C. should have sufficient flux to drop the surface temperature to about 0° C. If the same cooling flux is continued during the long laser pulse, the surface of the skin will remain at about 0° C., but the skin temperature with depth will increase over that established during the precooling step. At the depth of the hair roots, the temperature should increase to about 70° C. to 80° C. for about 0.1 second. At about 50 to 100 microns depth, the level at which the melanosomes are found, the temperature should not rise to more than about 50° C. to avoid damage to skin pigmentation.

A "long" laser pulse, as used herein, is defined with reference to the type and size of the chromophore particles illuminated and the wavelength of light used. Functionally, a long pulse is a pulse long enough to substantially avoid exploding or vaporizing chromophore particles infiltrated into hair ducts. The invention is illustrated with reference to light at a wavelength in the range of from about 600 nm to about 1100 nm and carbon or graphite particles in the size range of about 10 nm to about 1 $\mu$m. At this wavelength and particle size, a long pulse has a duration of from about 100 $\mu$s to about 100 ms. Alternatively, as used herein a long laser pulse can be a train of shorter pulses in such rapid succession that the interval between the end of one pulse and the beginning of the next pulse is less than the average thermal relaxation time of the chromophore particles. Such a train of short rapid pulses approximates the characteristics of a single long pulse. For example, at the above wavelength and carbon particle size, a train of shorter pulses having a pulse duration of about 1 ms to about 10 ms separated by about 1 ms can be substituted for a single pulse having a duration longer than the pulse width of a single pulse in the pulse train. A chopped CW laser is also considered a "long" pulse laser as the term is used herein.

A "long" pulse laser is one which releases its energy over a sufficient period of time that a light-absorbing chromophore surrounded by skin tissue, for example in a hair duct, has time to transfer energy from the chromophore to the surrounding tissue during the pulse. Because heat flows out of the chromophore into surrounding tissue, explosion of the chromophore particle is avoided. Generally, to denature the immediately surrounding tissue, the transfer of heat should be sufficient to raise the temperature of tissue immediately surrounding the base of the hair duct to about 70° C. to about 80° C. for a period of from 0.1 to 1 second for a radial distance of no more than about 60 microns from the wall of the hair duct. It should be particularly noted that as the pulse duration increases, the laser energy required to accomplish the requisite heating and the distance to which the target temperature extends is increased. Therefore, for carbon particles having an average diameter from about 10 nm to about 1 $\mu$m, a fluence of about 15 J/cm$^2$ is used with a pulse duration of about 100 $\mu$s, while a fluence of about 30 J/cm$^2$ is used with a pulse duration of about 100 ms. At a fluence of about 30 J/cm$^2$ and pulse duration of about 100 ms, tissue will be denatured for a radial distance of about 60 microns from the wall of the hair duct. Further increase in the distance to which tissue is denatured is generally not necessary or desirable for the purposes of inhibiting hair growth.

Due to the steep temperature gradient established by precooling the skin surface and the continued application of the cooling flux during a long pulse illumination, the temperature of the epidermis and upper dermis is kept cool enough during the laser pulse to avoid damage, while the temperature of the tissue surrounding a hair duct at the depth of the hair root increases sufficiently to inhibit future hair growth. Thus, selective damage of hair follicles can be achieved during laser hair removal without undesirable damage to other skin structures.

Figure 32:
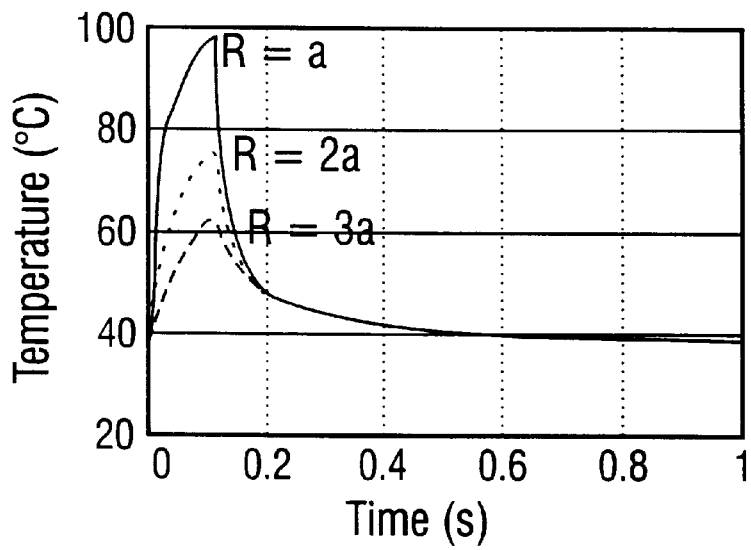

FIG. 32 shows the calculated temperature rise in tissue surrounding a hair follicle that is filled with carbon/oil lotion and illuminated with a 60 W/cm² Nd:YAG laser (1064 nm) for 0.1 second. The hair follicle is considered as an infinitely long cylinder with a radius of a=25 μm. It is assumed in the calculation that the follicle is filled with enough carbon particles so that essentially all photons striking the follicle are absorbed. As seen from FIG. 32, the temperature of the tissue between the wall of the follicle and one radius away from the wall is over 70° C. for a period of about 0.1 second, which is enough to thermally kill the cells in the tissue. The goal of long term inhibition of hair growth is achieved when tissue up to one radius length away from the wall of the hair duct is thermally damaged.

Because of absorption and scattering of photons by tissue, the photon flux distribution in skin decays approximately exponentially with depth. The light intensity at 3 mm depth may be only 25% of the incident flux. It has been discovered that the power density of incident light should be 240 W/cm² in order to have 60 W/cm² at 3 mm depth, the average depth of hair follicles in an average section skin. However, a skin surface illuminated with 240 W/cm² fluence of 1064 nm wavelength laser for 0.1 second will be burned unless cooled. To succeed in providing sufficient power to the chromophores at the base of the hair follicle without burning skin tissue, other than that immediately surrounding a hair duct, dynamic cooling is applied to the surface of the skin section that is being illuminated. For example, in one embodiment the contaminant contains carbon particles in a size range from about 10 nm to about 1 μm, the laser wavelength is in the range of 600 nm–1100 nm, the pulse duration varies from 100 μs to 100 ms, and the laser energy range is from 3 J/cm² to 30 J/cm² depending on the pulse duration. The longer the pulse duration, the higher the laser energy required. A pulse duration of about 100 ms is preferred.

Figure 33:
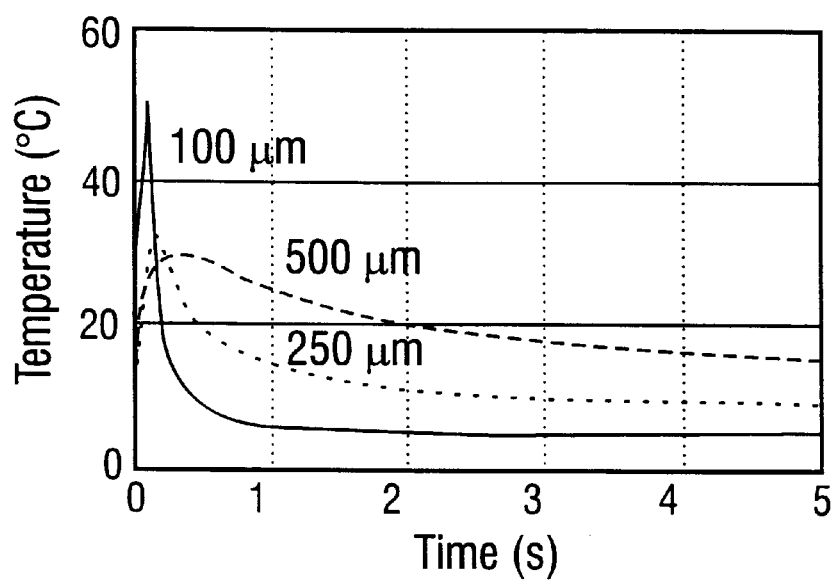
FIG. 33 is a graph showing the temperature (T) profile with depth of skin when the skin surface is cooled prior to long pulse laser irradiation according to the method of the invention. Solid line=T at 100 μm; dashed line=T at 500 μm; dotted line=T at 250 μm.
Figure 34:
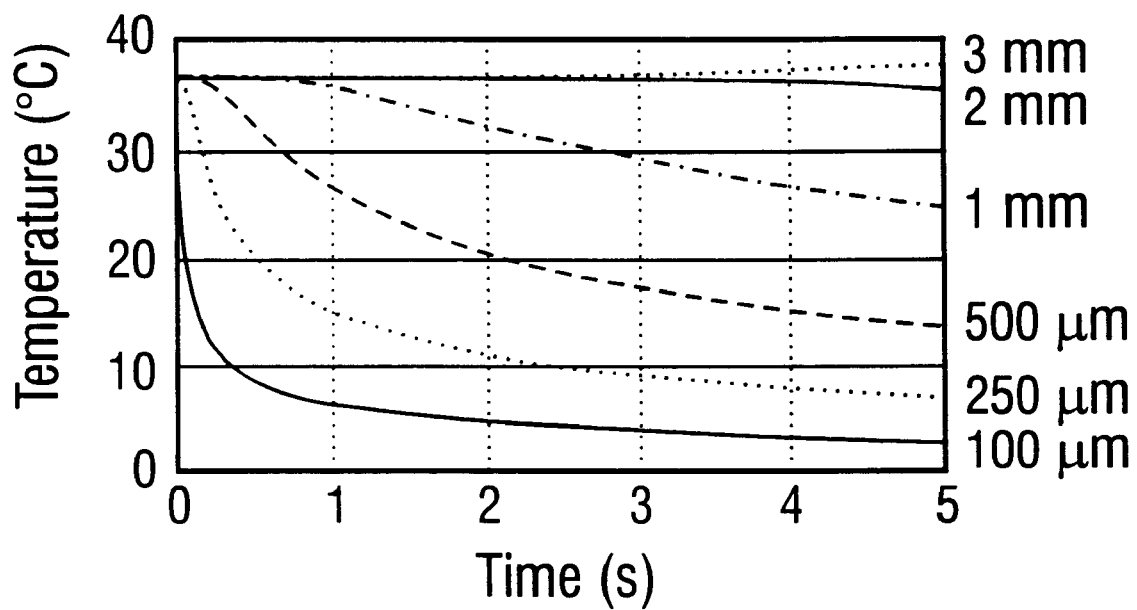
FIG. 34 is a graph showing the temperature (T) profile in skin tissue with depth after the skin surface has been exposed to cooling at 0° C. for 2 seconds. Lower solid line=T at 100 μm; lower dotted line=T at 250 μm; lower dashed line=T at 500 μm; line of alternating dots and dashes=T at 1 mm; upper solid line=T at 2 mm; and upper dotted line=T at 3 mm.

The area of skin surface that needs to be cooled is the area that is being illuminated. Therefore, the cooling medium can be applied directly onto the skin surface where the treatment for hair removal is sought. For example, the cooling effect can be accomplished by applying to the skin surface a continuous spray of ice water or other coolant that will be capable of bringing the surface of the skin to a temperature in the range from about 0° C. to about 10° C. when the cooling medium is applied for from about 1 to about 5 seconds. FIG. 33 above shows skin temperature at three different depths from the surface when the skin surface is cooled to 0° C. for 2 seconds. After exposure of the skin surface to 0° C. for 2 seconds, temperature in the epidermis and upper dermis is lowered significantly from body temperature, but the lower dermis remains at a temperature almost equivalent to body temperature, as shown in FIG. 34.

An environmentally compatible Freon™ substitute, such as tetrafluroethene, is also suitable for this purpose. Alternatively, a cooling device designed to cool the surface of the skin during lasing can be used to administer a comparable cooling flux to the section of skin during lasing. Such a device is disclosed in co-pending U.S. application Ser. No. 60/067,460, filed on even date with this application, which is incorporated herein by reference in its entirety.

Further methods of skin cooling are disclosed in Section No. 2 above.

In summary, the method of the invention is a three step process as follows:

1. A cooling flux is applied to section of skin sufficient to precool its surface to about 10° C. to −10° C. prior to illumination. Generally, the precooling period is from 1 to 5 seconds, for example one second.

2. A cooling flux is maintained on the surface of the skin section throughout a single laser pulse. Generally the cooling flux used during the precooling step is continued during a single long pulse of the laser. The duration and energy of the long pulse is sufficient that energy absorbed by the contaminant and transferred to tissue immediately surrounding the base of a hair follicle in the section of skin destroys hair growth cells therein despite the temperature gradient in the skin established by the precooling and cooling maintained during the laser pulse. Generally, tissue within about 1 to 2 follicle widths from the wall of the hair duct (or about 30 to about 60 microns) is heated to a temperature from about 70° C. to 80° C. for a period of about 0.1 second by heat transferred from the contaminant during a single laser pulse, which is about 0.1 second in duration. The cooling flux on the skin surface is maintained throughout the laser pulse to protect tissue further than about 1 to 2 follicle radii from the wall of the hair follicle from damage.

3. At the conclusion of the pulse, the cooling flux is terminated and the surface of the section of skin is allowed a rest period to return to body temperature before the three-step process is repeated.

A total of 1 to 3 treatments is generally sufficient to cause long term inhibition of hair growth in a section of skin treated using the above method. Rather than ceasing the laser treatment during the rest period, it is generally convenient to use the three-step cycle in treatment of a different section of skin during the rest period, so long as the new section of skin is about body temperature at the start of the three-step process. If the circumference of the cooling zone is substantially the same size as the spot size of the laser beam, an adjacent skin section may be at body temperature within less than a second following the conclusion of the laser pulse. In any event, it may be convenient to program a laser to move automatically from skin section to skin section in a predetermined pattern so that an area of skin containing several skin sections (each one of which may be no larger in area than the beam spot size) is scanned in an orderly pattern, moving through the pattern from one to about three times as needed to accomplish the goal of inhibiting hair growth without undesirable damage to skin tissue.

The present invention advantageously avoids production of kinetic energy generated by exploding or volatilizing exogenous chromophore particles in a hair duct, which can damage the natural chromophores at the meeting point of the epidermal and dermal layers, thereby disrupting the pigmentation of the skin surface. In addition, pinpoint bleeding in the skin is avoided. The present invention provides the advantage that these risks are completely avoided by utilizing a long laser pulse in combination with dynamic skin cooling.

This aspect of the invention having been fully described, it is further illustrated by the examples below.

EXAMPLE 8

Sample calculations were performed utilizing a precooling flux applied to the surface of the skin section sufficient to attain a temperature of about 20° C. at a depth of about 500 μm below the surface of the section of skin within two seconds. If this cooling flux was maintained during a long pulse of laser light (60 W/cm², Nd:YAG laser at wavelength of 1064 nm, pulse duration of 0.1 second), the temperature of the tissue surrounding the contaminant filled hair duct increased to a temperature of about 70° C. to about 80° C. for a period of about 0.1 second. This temperature increase is sufficient to destroy the cells, but higher fluence is need for damage to follicular tissue at a depth of 3 to 4 mm, as discussed above.

EXAMPLE 9

For comparison, similar calculations were made using the same laser cooling regimen and parameters (60 W/cm$^2$, Nd:YAG laser at wavelength of 1064 nm, pulse duration of 0.1 second) to determine the temperature rise of blood vessels in the upper dermis and in melanosomes at the interface of the epidermis and dermis. These calculations showed that the temperature rise of blood vessels with a diameter smaller that 50 μm is less than 20° C. under the above laser conditions. Further calculations showed that under the same conditions the heat generated in an individual melanosome of 1 μm diameter located at the interface of the dermis and epidermis by a laser pulse with a duration of 0.1 second is dissipated into the surrounding tissue without substantial increase of temperature over that of the surrounding skin tissue. Hence with continuous cooling of the skin surface during each laser pulse, as described above, the tissue in and surrounding a contaminant-filled hair duct can be selectively coagulated without unwanted burning of skin, or damage to blood vessels and skin pigmentation.

No. 21: Use of Radio Waves to Control Hair Growth

It is known to use various wavelengths of light in skin treatments and to cause inhibition of hair growth. Use of other types of electromagnetic radiation would enhance the choices, allowing the practitioner to select the type of radiation best suited to a particular task.

Figure 36:
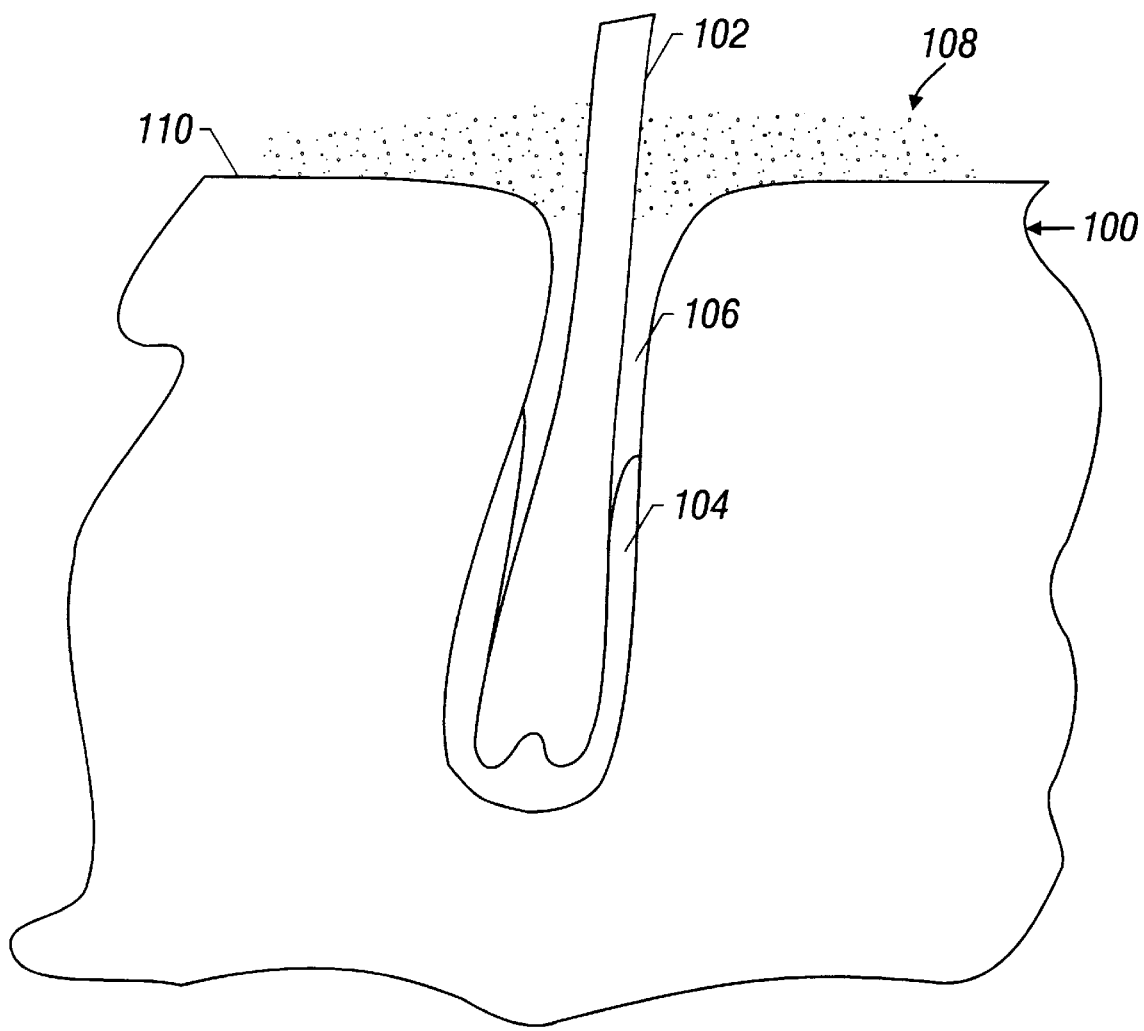
FIG. 36 is diagrammatic section view of a hair in a section of skin, with metallic particles applied to the skin surface according to a feature of the invention.

This aspect of the invention provides a system for encouraging or retarding hair growth. Referring now to FIG. 36, a section of skin 100 includes one or more hairs 102 growing from follicles 104 in hair ducts 106. Metallic particles 108, for example, nanophase iron particles, are applied to the skin surface 110. Particles 108 may be applied as a powder, in a solution or in a lotion formulated for topical application.

Figure 37:
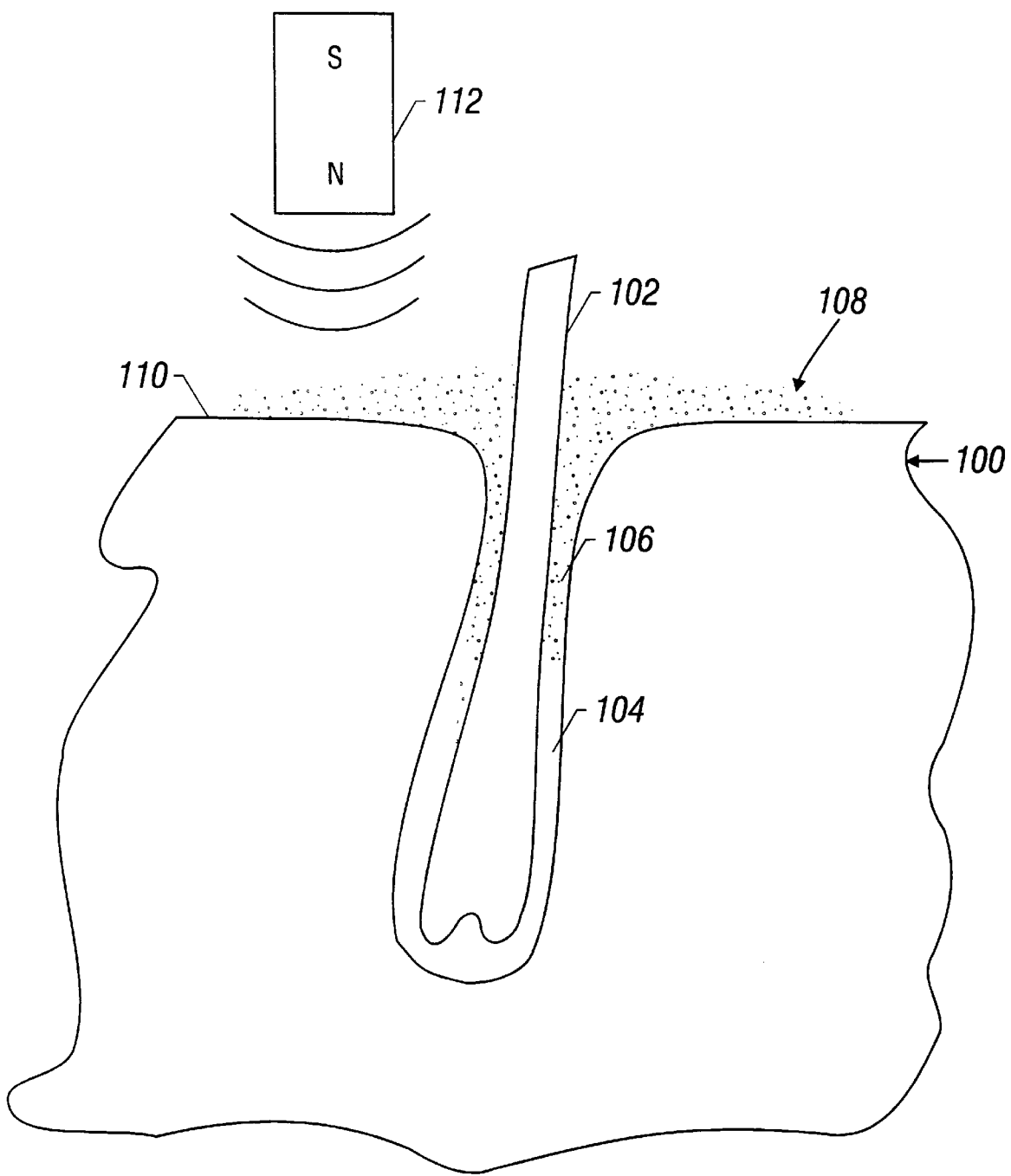
FIG. 37 is a view of the hair and skin section of FIG. 36, illustrating the use of magnetic repulsion to encourage the metallic particles to move down the hair duct.

Referring now to FIG. 37, particles 108 are urged to enter hair ducts 106 and move down to follicles 104. In the illustrated embodiment, particles 108 are iron particles, which are ferromagnetic. A magnet 112 is used to apply magnetic repulsion to encourage at least some of particles 108 to enter hair ducts 106 and move down towards follicles 104. Alternatively, skin section 100 can be gently massaged to encourage particles 108 to move toward follicles 104 at the bottoms of hair ducts 106. After particles 108 have been worked into hair ducts 106, skin section 100 can be wiped and gently washed clean to remove excess particles from surface 110.

Figure 38:
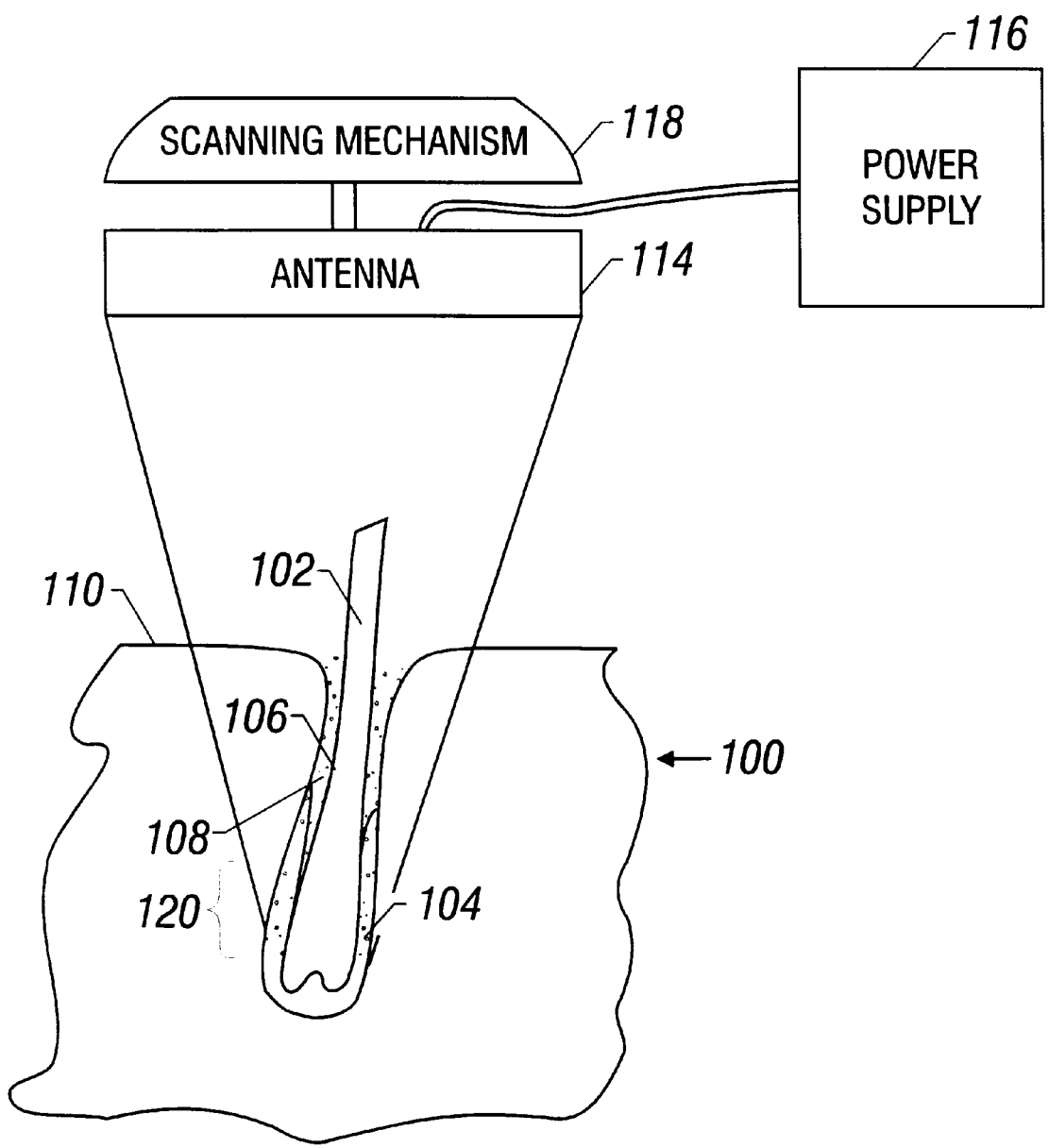
FIG. 38 is another view of the hair and skin section of FIGS. 36 and 37, to which RF radiation is being applied.

Referring to FIG. 38, a system for heating particles 108 in ducts 106 includes a radio frequency (RF) antenna array 114, an associated power supply 116, and a scanning mechanism 118 for scanning RF emissions from antenna over skin section 100. Scanning mechanism 118 can be a mechanical system that moves antenna array 114, or an electronic system that oscillates power applied from supply 116 to antenna array 114.

The RF radiation from antenna array 114 is absorbed by particles 108, which heats them. Particles 108 conduct heat to surrounding tissue in follicle 104. The radiation can be tuned and scanned across skin section 100 in a manner that converges the radiation at a carefully selected depth in skin section 100, generally from 1 mm to about 4 mm below the surface of the skin. This enables the system to target damage to follicular cells in predetermined regions 120 of follicles 104. Depending on the phase of growth, thermal damage to follicle cells may activate or retard hair growth.

Any metallic material or organometallic compound that absorbs RF radiation can be used in practice of the invention, including those in solution or as a free compound. Although RF radiation is well suited for heating nanophase iron particles, other types of radiation, such as microwave, and other frequencies that are matched to a particular metallic material or organometallic compound may also be employed. Particle sizes are not restricted to nanometer sizes. Particle sizes can include all sizes that can infiltrate the follicle and that, when combined with a suitable electromagnetic radiation, can provide focused heat in hair follicles 104.

A number of embodiments of the present invention have been described. Nevertheless, it will be understood that various modifications may be made without departing from the spirit and scope of the invention. Accordingly, other embodiments are within the scope of the following claims.

What is claimed is:

1. A method for hair removal, comprising:
    inducing hairs into synchronized hair growth in a region of skin prior to hair removal including applying a shocking agent or action to the skin region to shift the phase of hair into the anagen phase; and
    illuminating the region of skin while the hairs are in the anagen phase.

2. The method of claim 1, wherein the shocking agent is selected from the group consisting of minoxidil or methionine.

3. The method of claim 1, wherein the hairs are induced into synchronized hair growth by irradiation, plucking, waxing or electrolysis.

4. The method of claim 1, wherein the region of skin is illuminated while the hairs are in early anagen phase.

5. The method of claim 1, wherein the hair growth is synchronized between 3 to 25 days prior to illumination.

6. The method of claim 5, wherein the hair growth is synchronized between 7 and 21 days prior to illumination.

7. The method of claim 1, further comprising applying an external contaminant.

8. The method of claim 7, wherein the external contaminant is applied prior to illumination.

9. The method of claim 8, wherein the external contaminant is selected from the group consisting of a chromophore particle, a light-absorbing dye and a photosensitizer chemical.

* * * * *